United States Patent [19]
Kriesel et al.

[11] Patent Number: 6,105,442
[45] Date of Patent: Aug. 22, 2000

[54] FLUID DELIVERY APPARATUS WITH RESERVOIR FILL ASSEMBLY

[75] Inventors: Marshall S. Kriesel, St. Paul; Steven M. Arnold, Minnetanka; James Garrison, Minneapolis; Farhad Kazemzadeh, Bloomington, all of Minn.

[73] Assignee: Science Incorporated, Bloomington, Minn.

[21] Appl. No.: 09/363,288

[22] Filed: Jul. 28, 1999

Related U.S. Application Data

[60] Division of application No. 09/017,047, Feb. 2, 1998, which is a continuation-in-part of application No. 08/718,686, Sep. 24, 1996, Pat. No. 5,721,382, which is a continuation-in-part of application No. 08/432,220, May 1, 1995, abandoned.

[51] Int. Cl.[7] ....................................................... B01L 3/00
[52] U.S. Cl. .......................................... 73/864.91; 73/864
[58] Field of Search ................................. 73/861.47, 863, 73/864, 864.91

[56] References Cited

U.S. PATENT DOCUMENTS

| | | | |
|---|---|---|---|
| 5,840,071 | 11/1998 | Kriesel et al. | 604/132 |
| 5,962,794 | 10/1999 | Kriesel et al. | 73/861.47 |
| 5,993,425 | 11/1999 | Kriesel | 604/191 |

*Primary Examiner*—Max Noori
*Attorney, Agent, or Firm*—James E. Brunton, Esq.

[57] ABSTRACT

An apparatus for delivering fluids at a precisely controlled rate which comprises a fluid dispensing component having a fluid reservoir for containing the fluids to be delivered and a reservoir fill component which can be removably interconnected with the fluid dispensing component. The dispensing component can be used for the precise infusion of pharmaceutical fluids to an ambulatory patient at controlled rates. The reservoir fill assembly is uniquely designed to accept a vial component of conventional construction which is partially received within a novel adapter subassembly that can readily be removably interconnected with the fluid dispensing component.

15 Claims, 39 Drawing Sheets

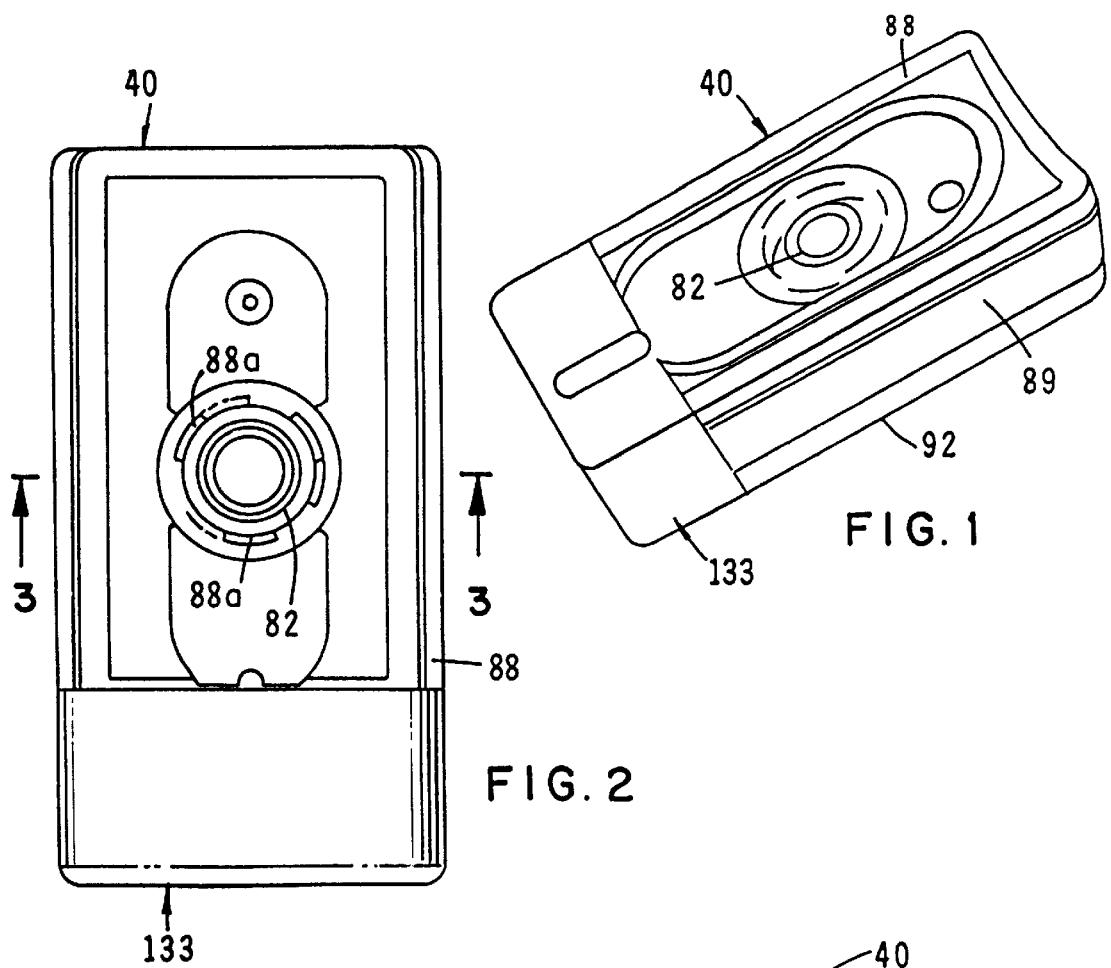
FIG. 1
FIG. 2
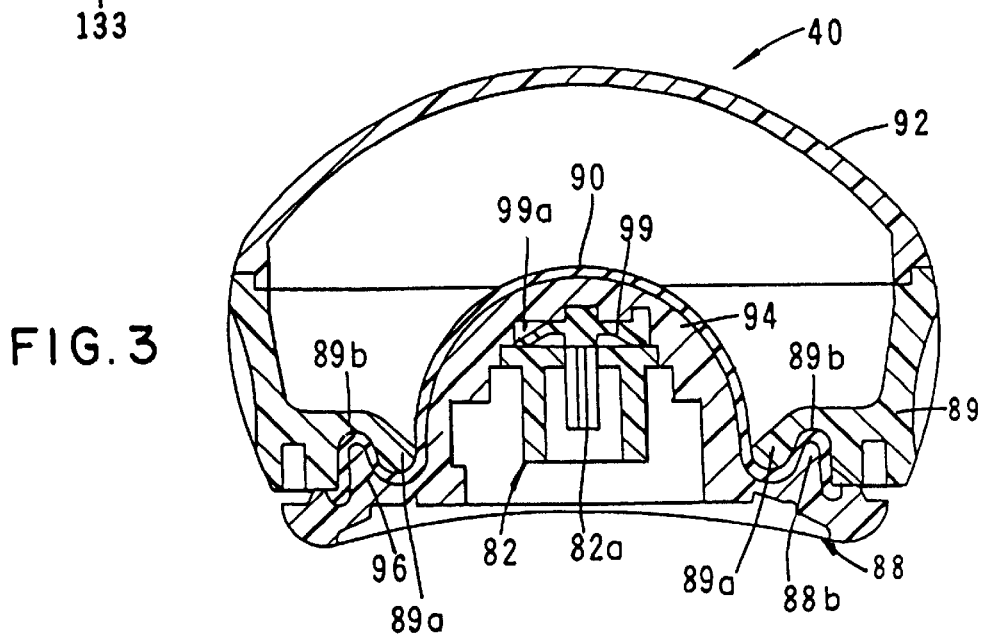
FIG. 3

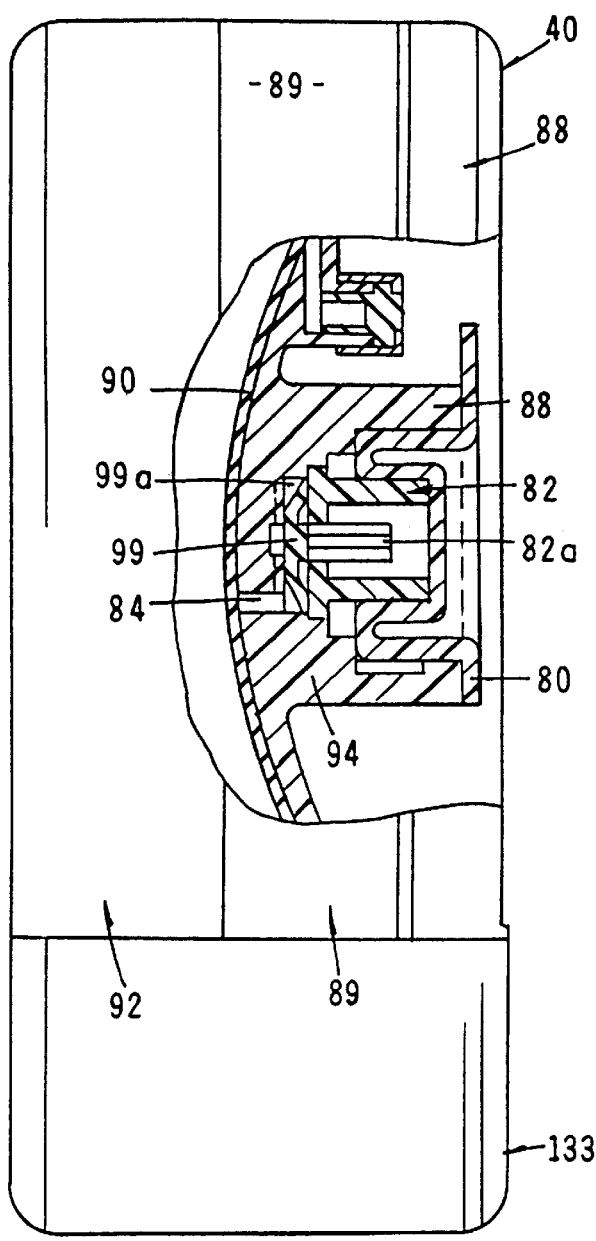
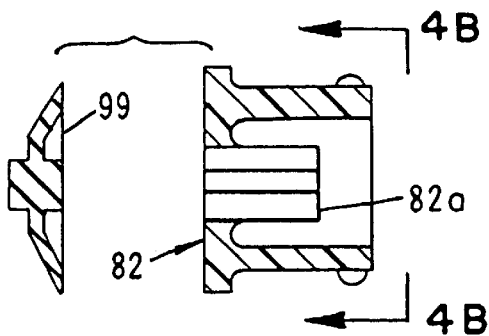
FIG.4A
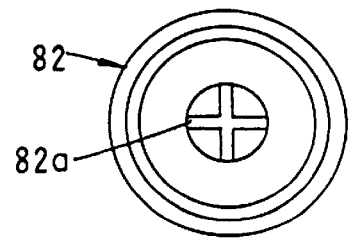
FIG.4B
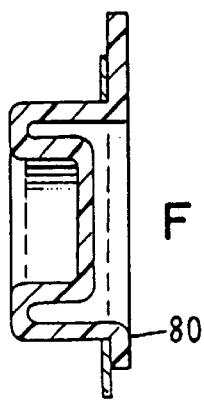
FIG.5
FIG.4
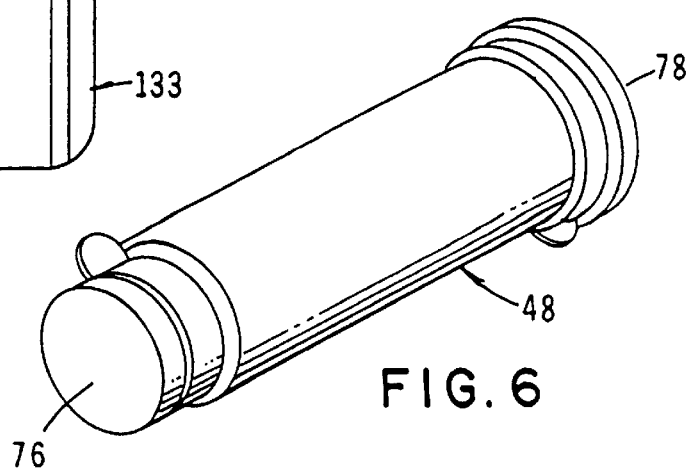
FIG.6

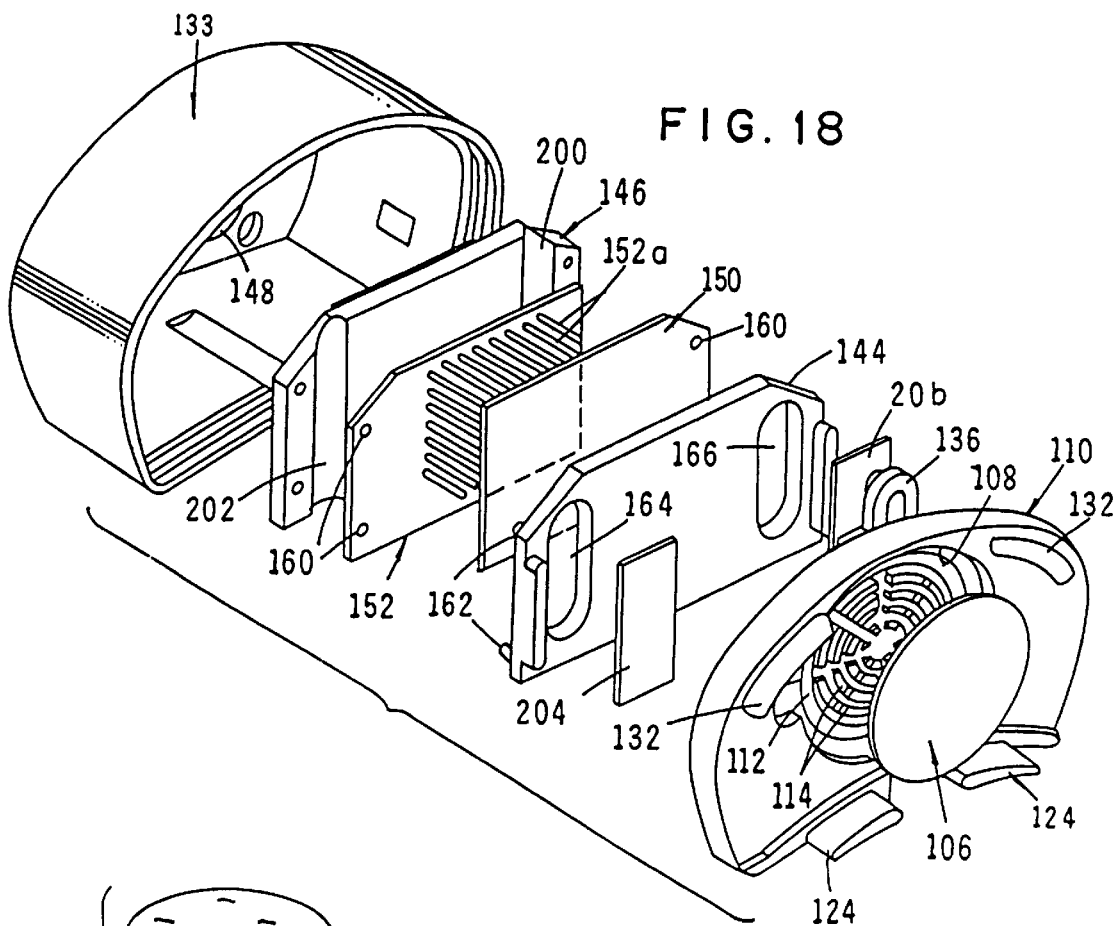
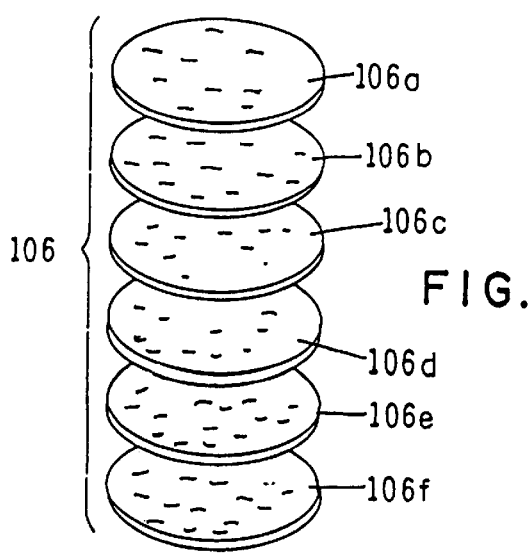
FIG. 18
FIG. 19

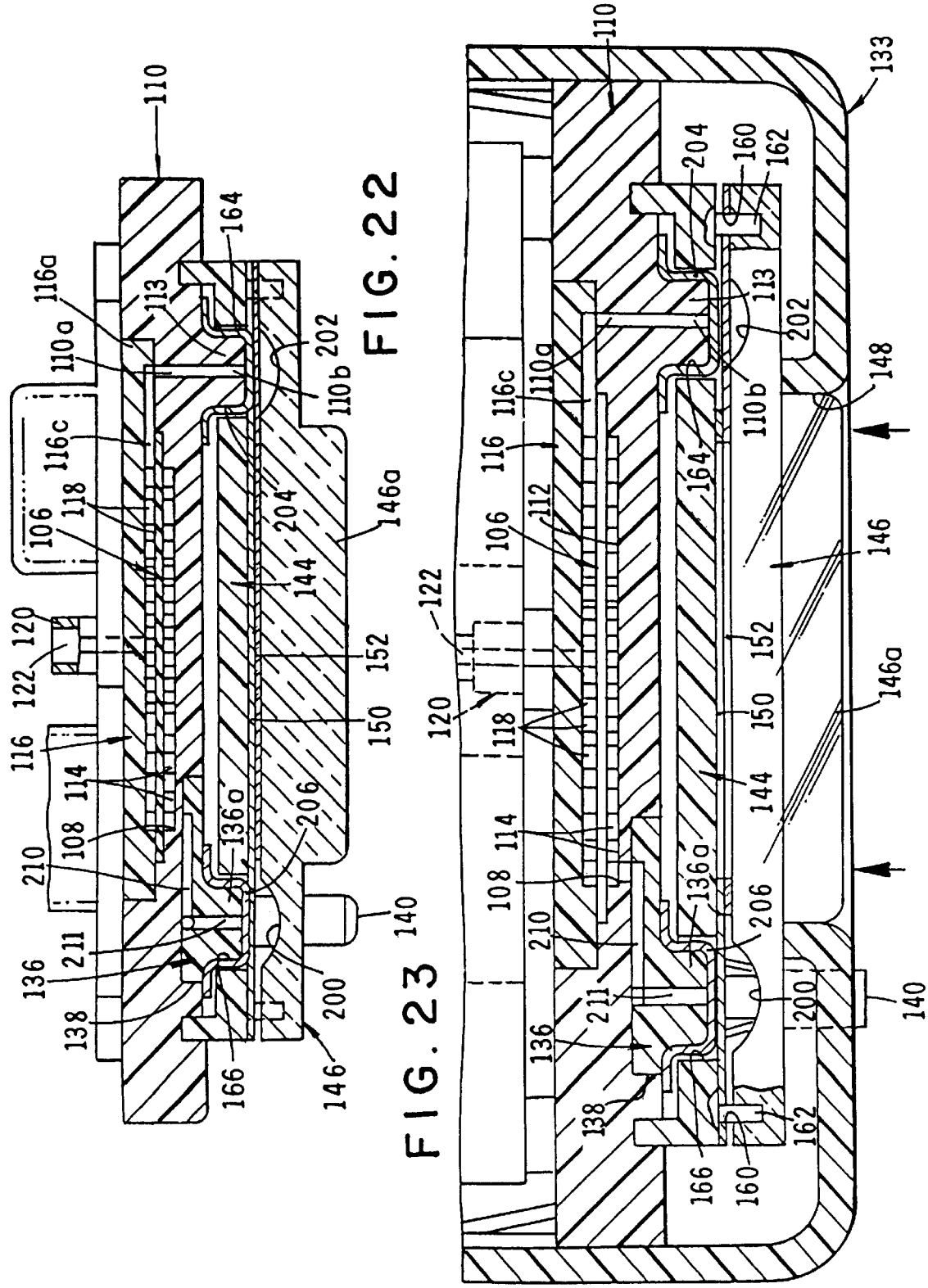

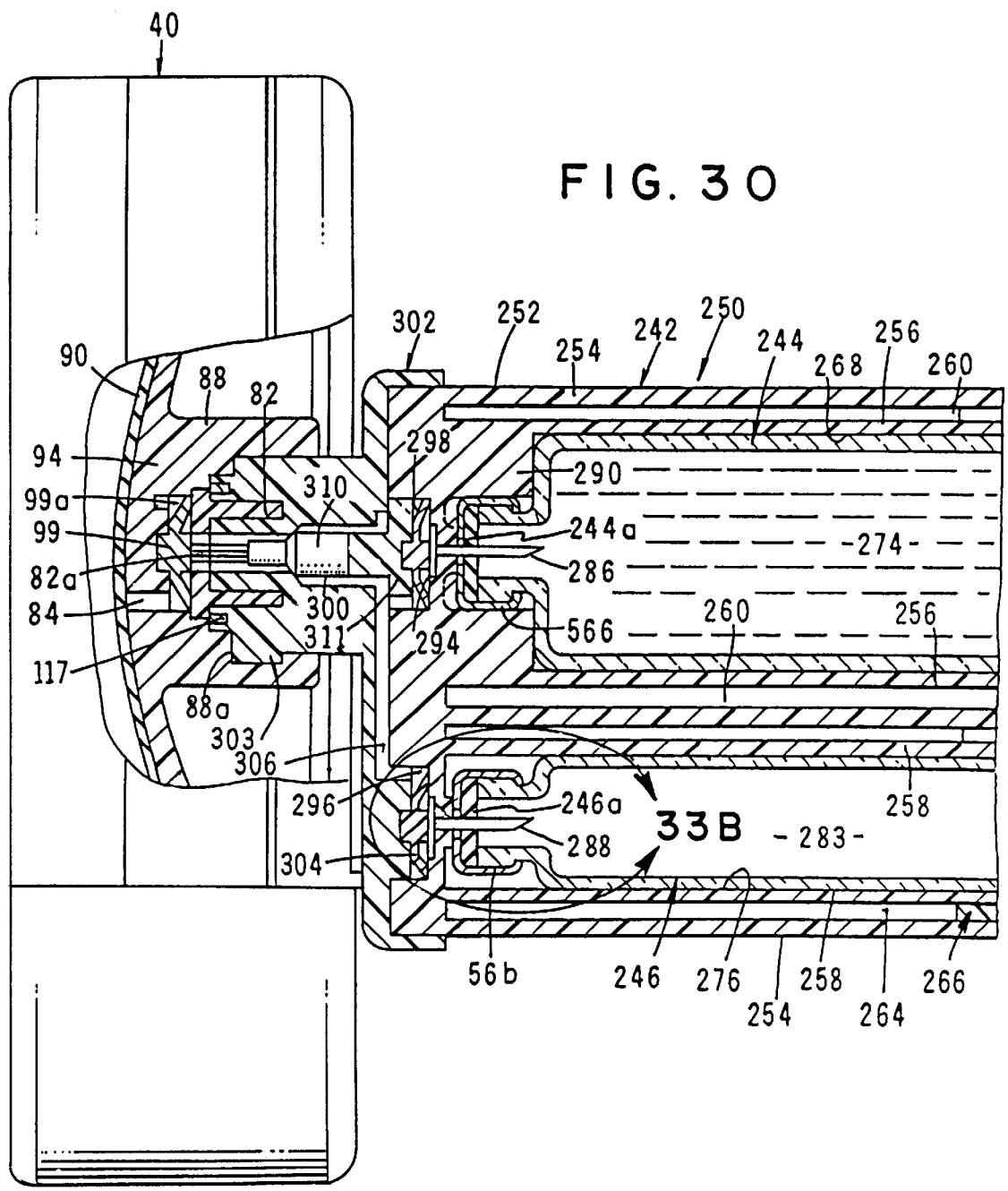

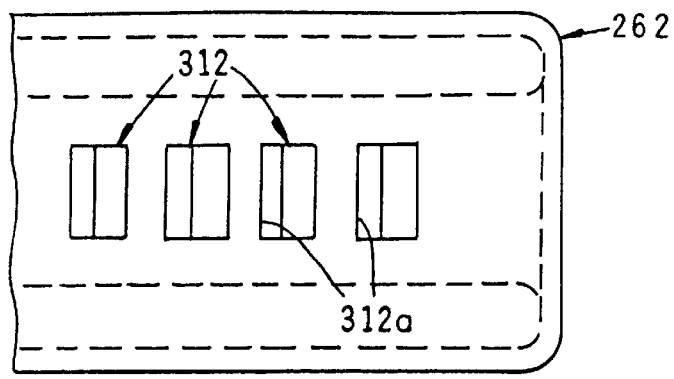
FIG. 31A
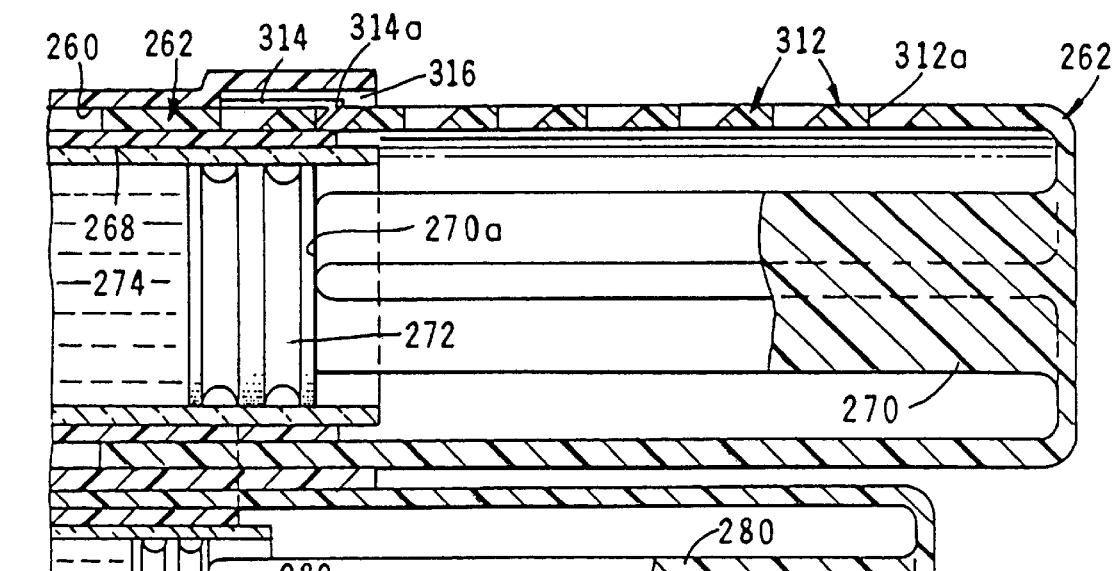
FIG. 30A
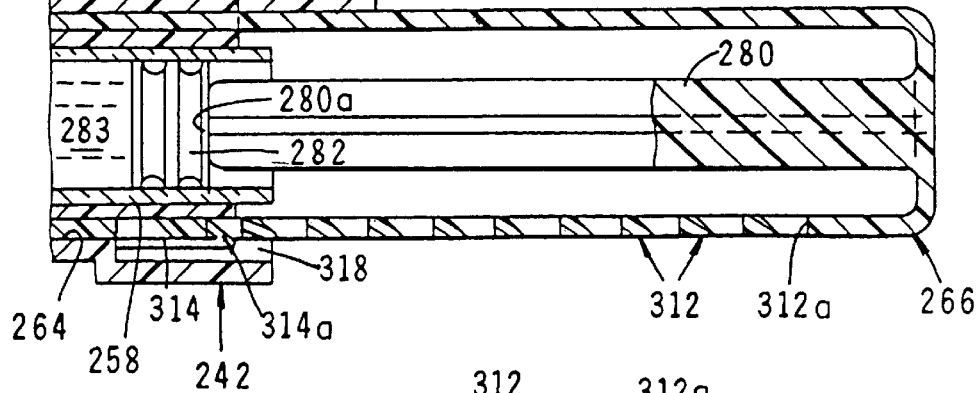
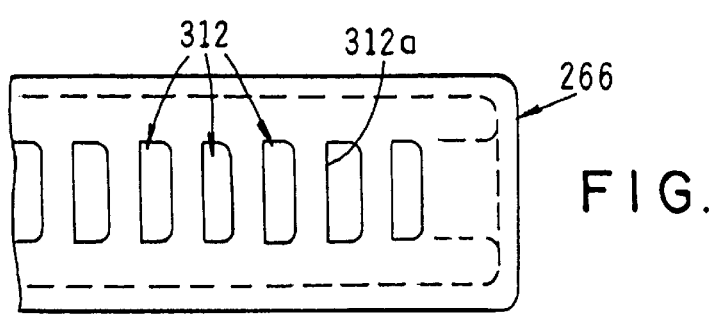
FIG. 31B

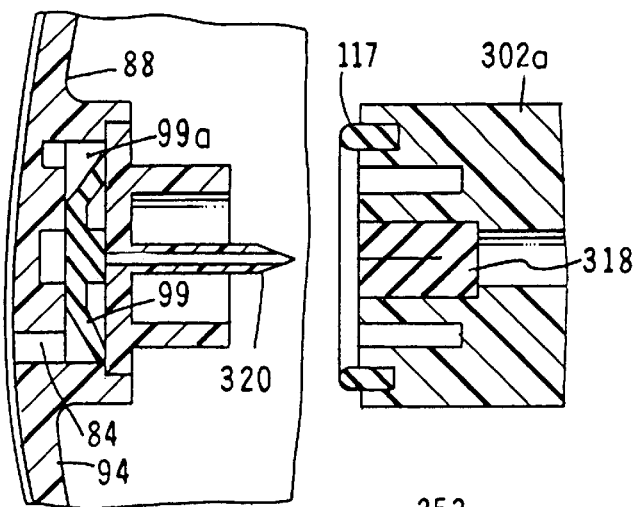
FIG. 32
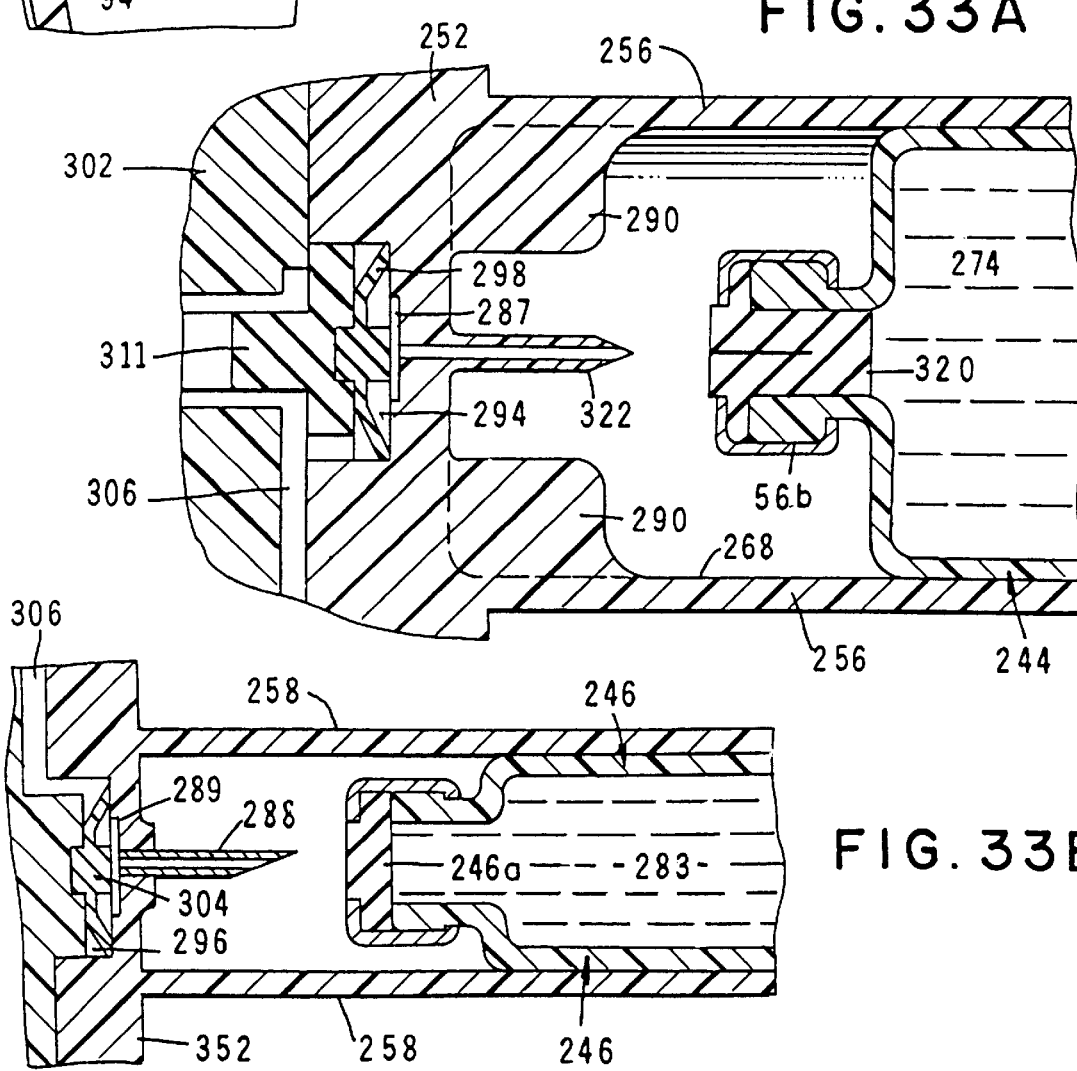
FIG. 33A
FIG. 33B

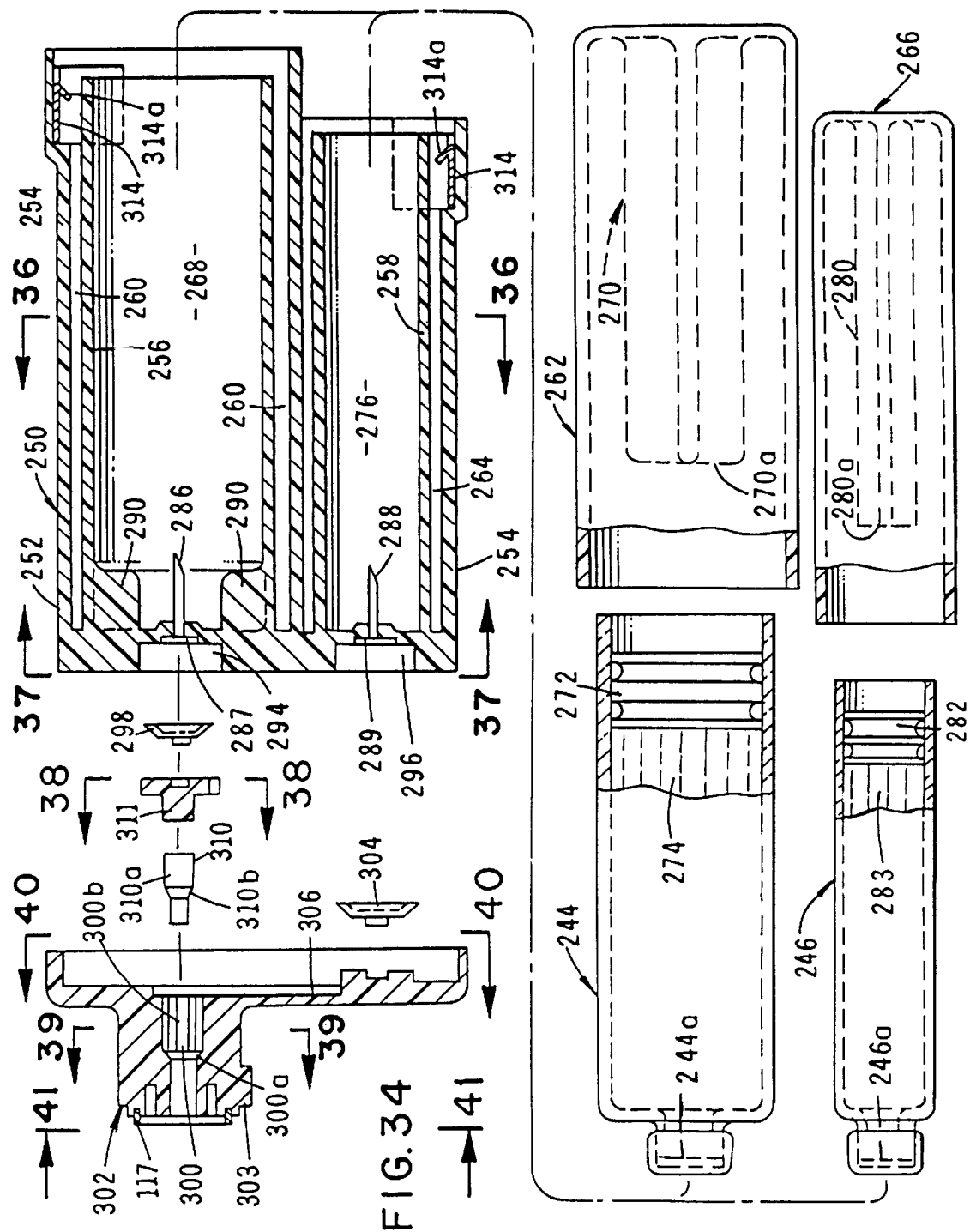

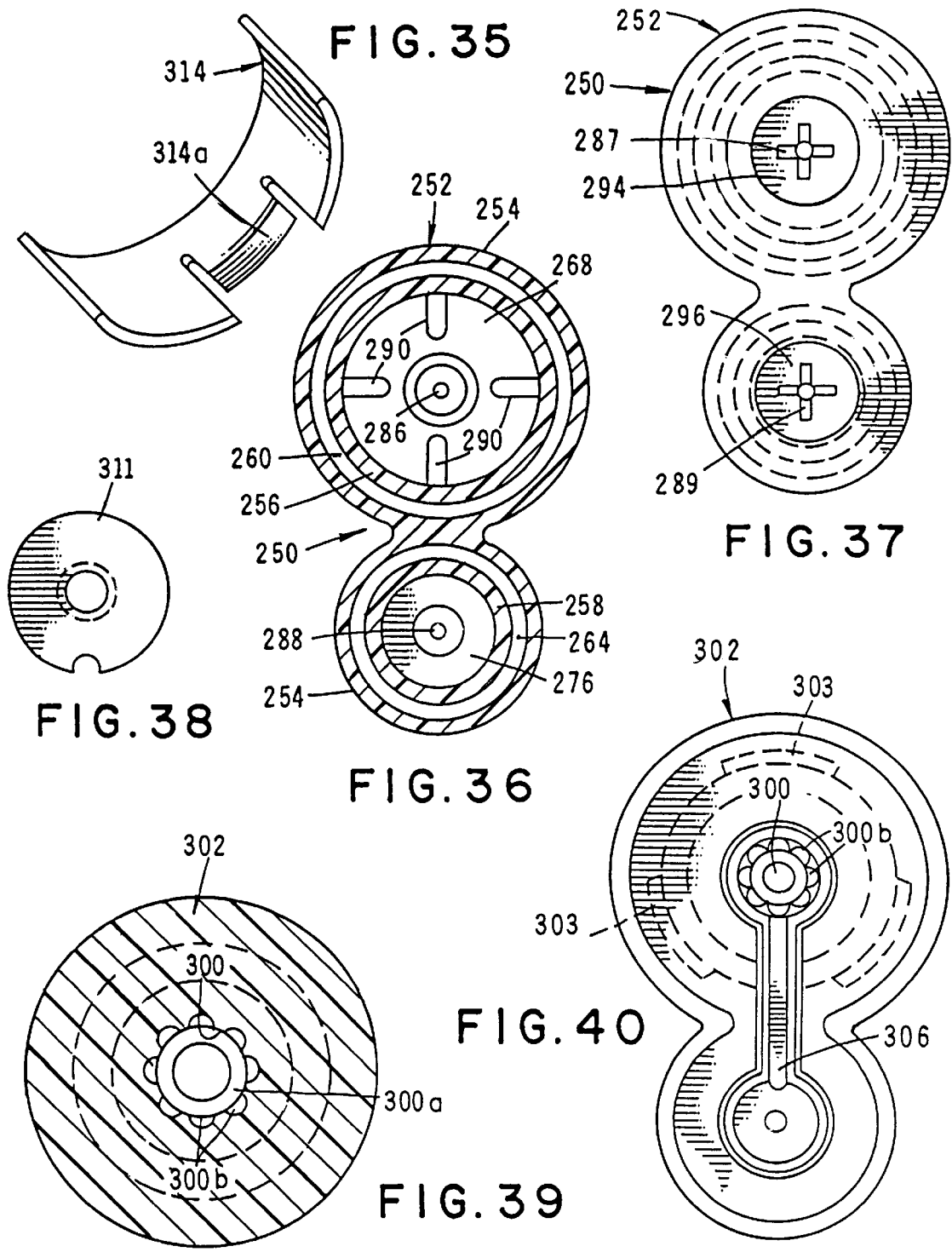

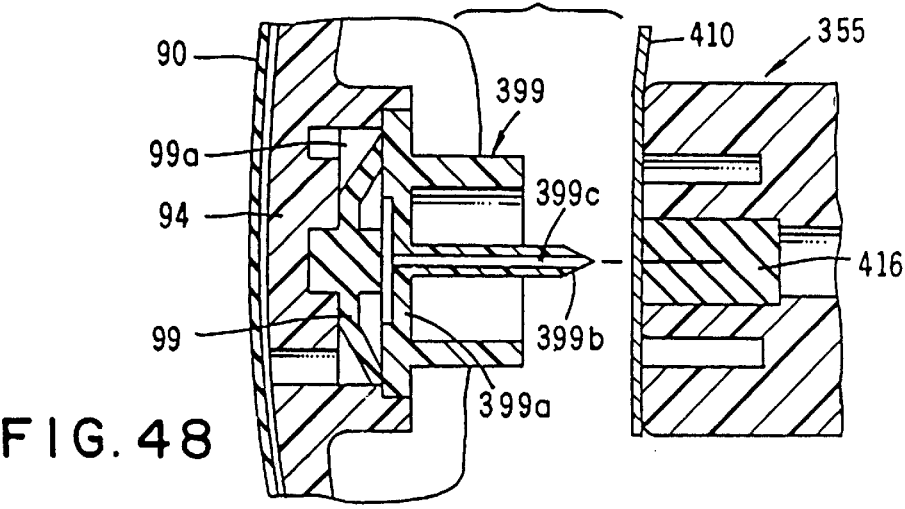
FIG. 48
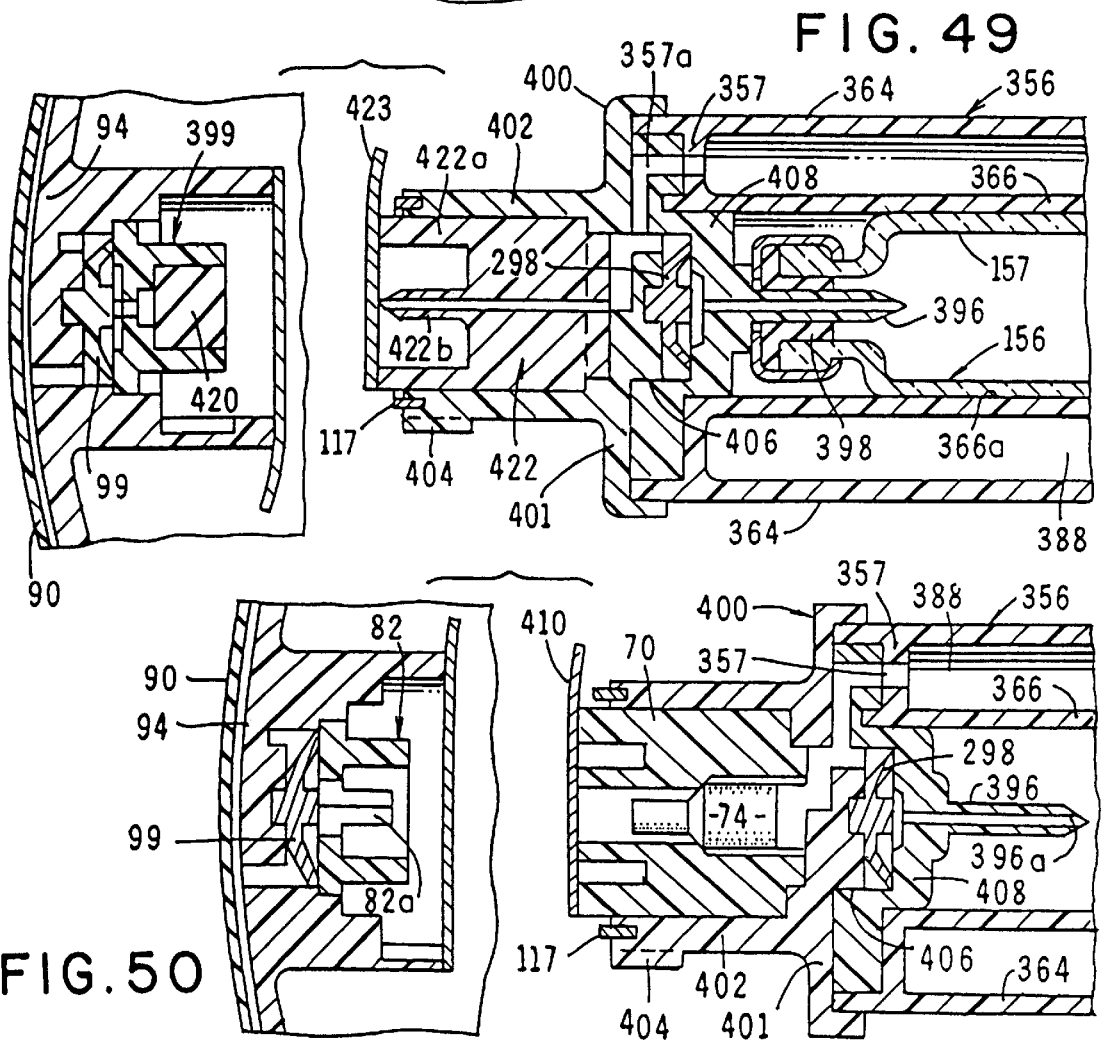
FIG. 49
FIG. 50

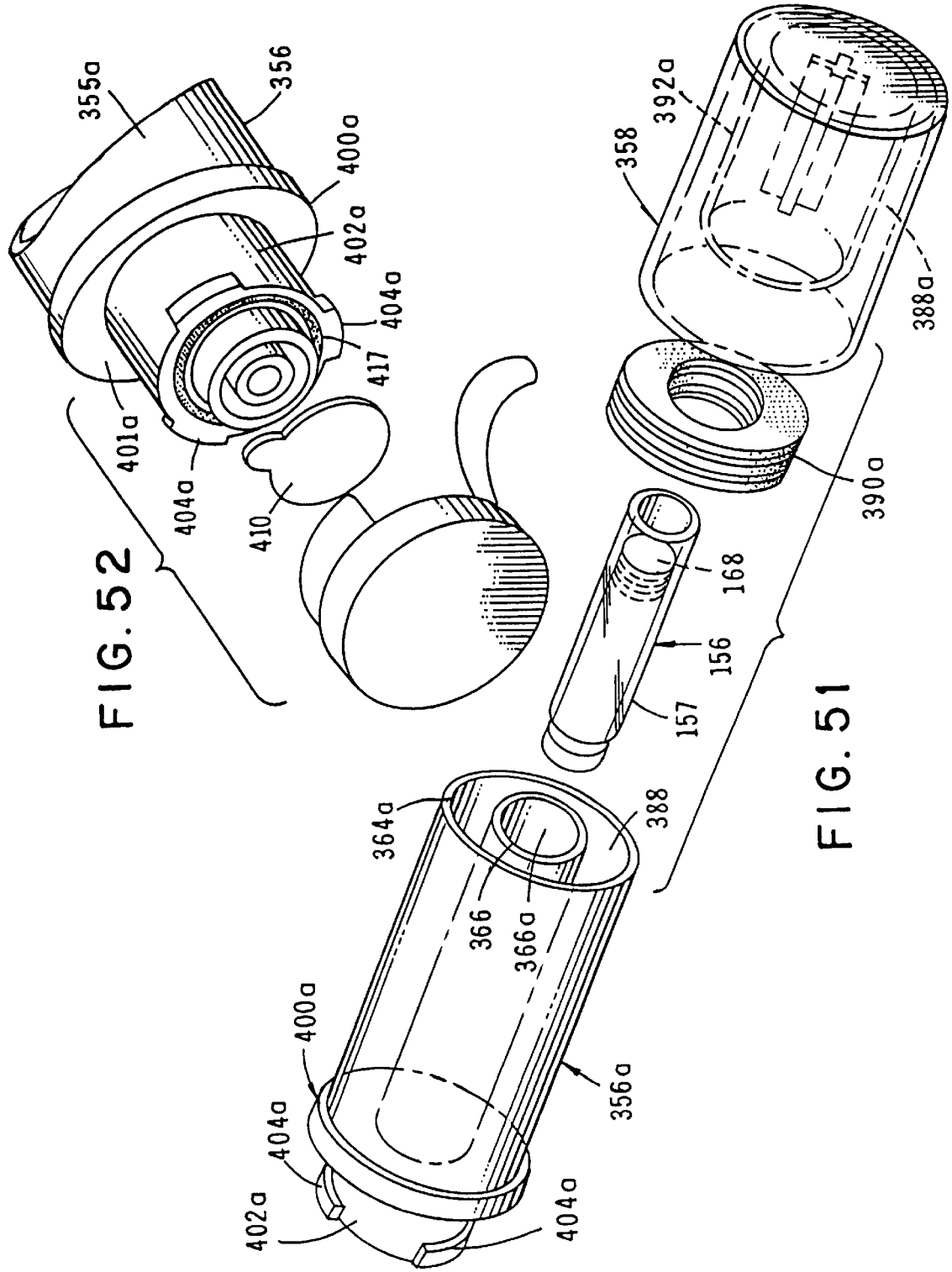

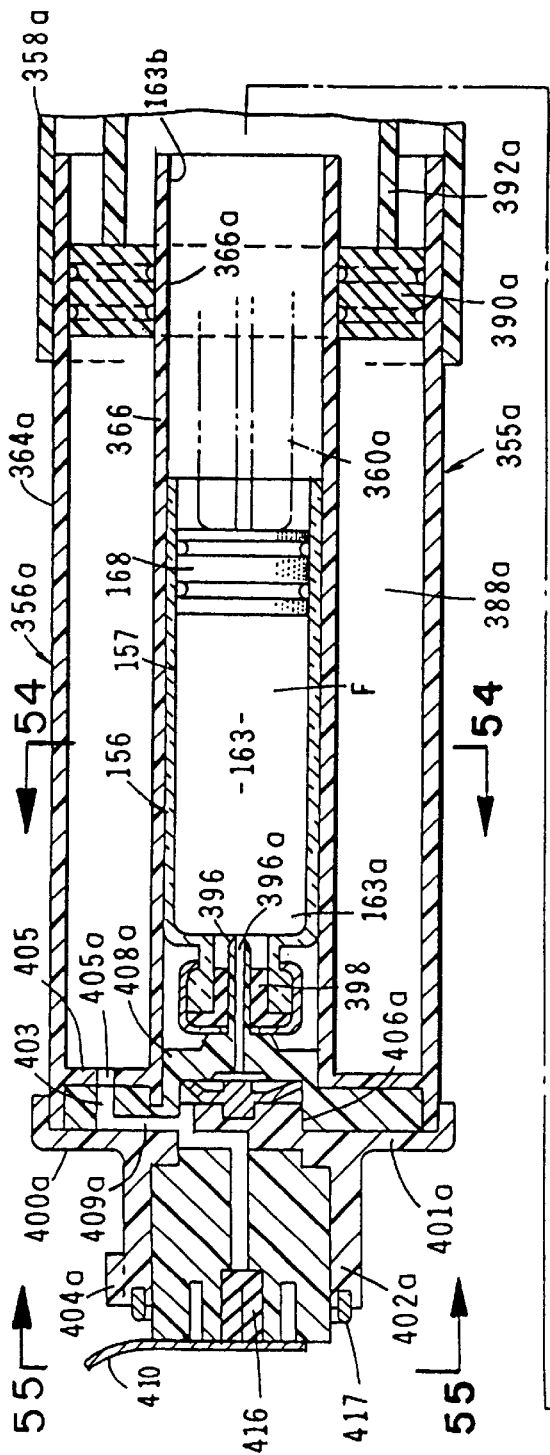
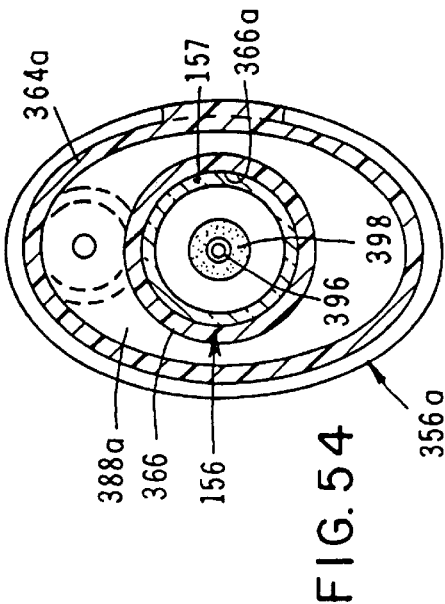
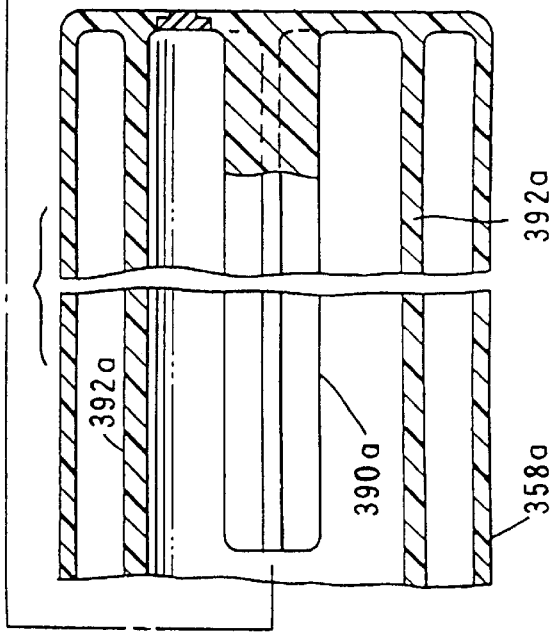
FIG. 53
FIG. 54

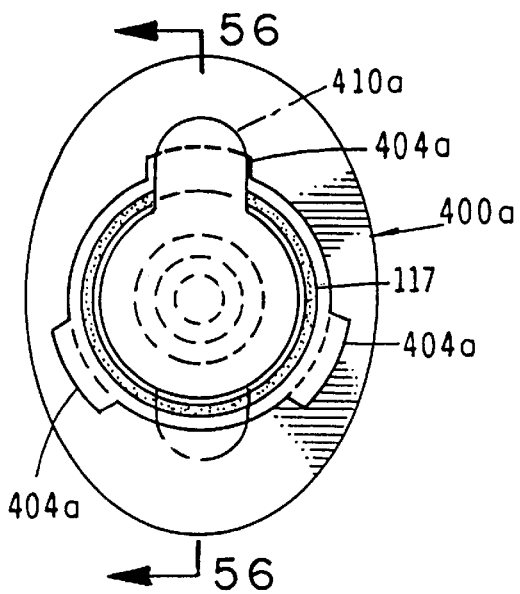
FIG. 55
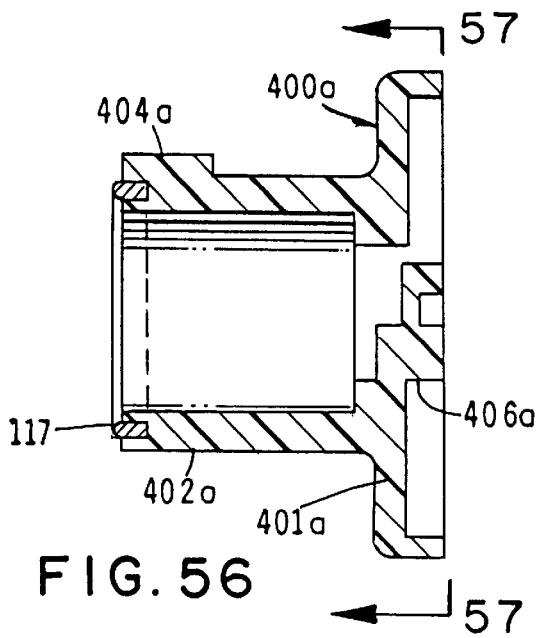
FIG. 56
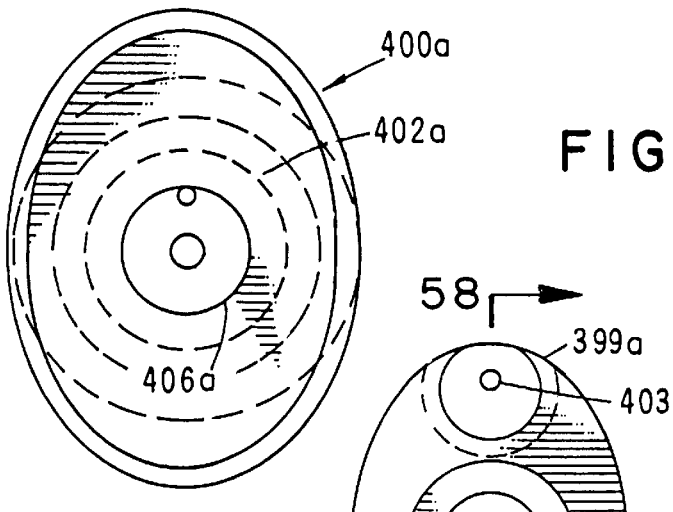
FIG. 57
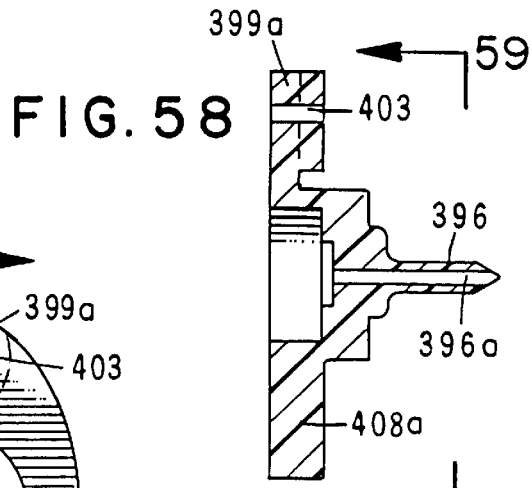
FIG. 58
FIG. 59

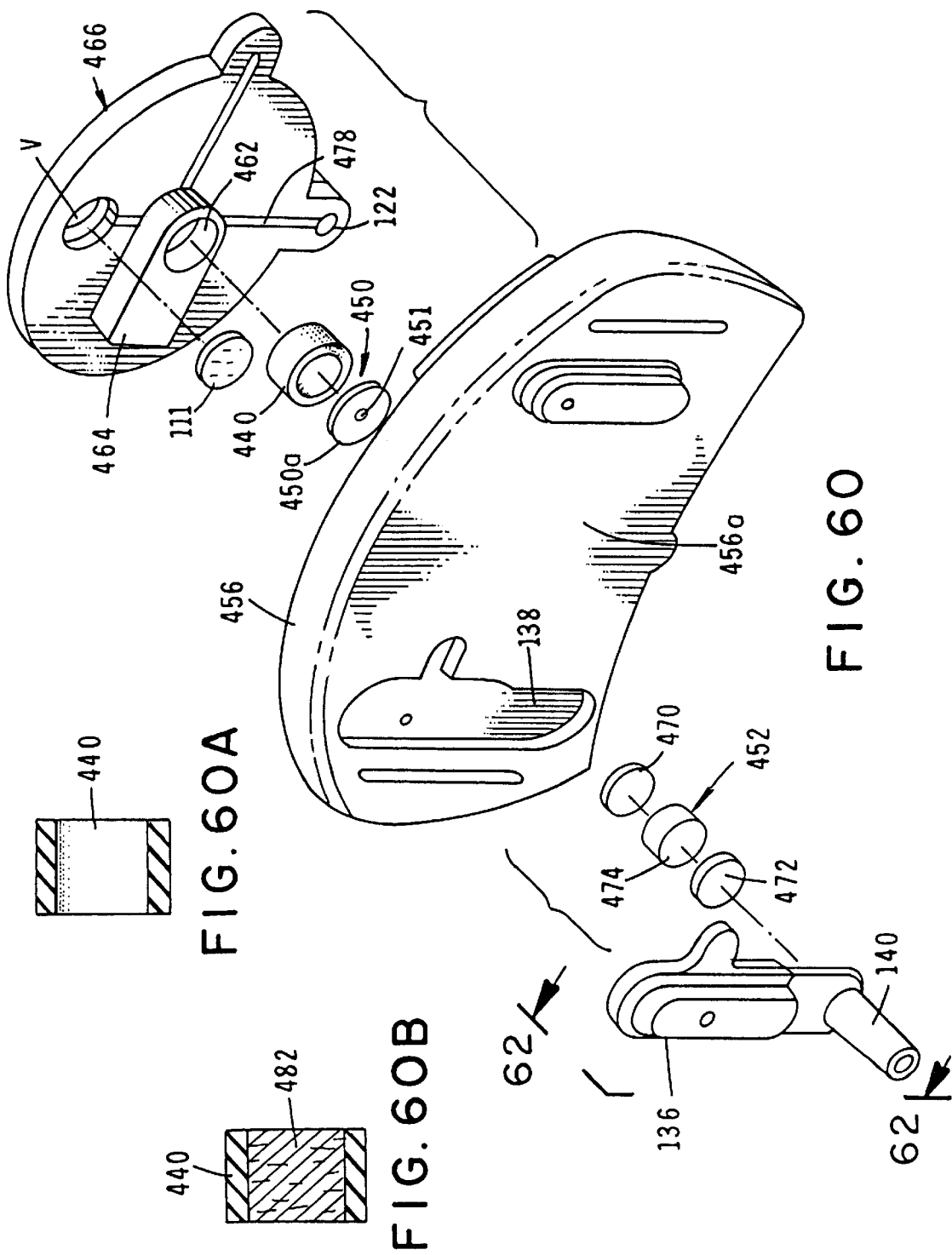

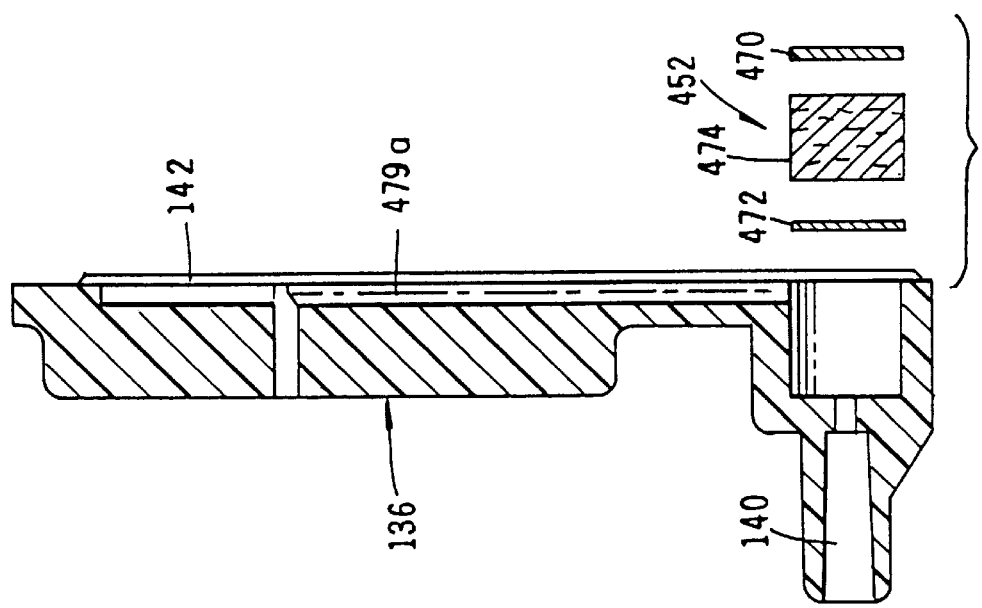
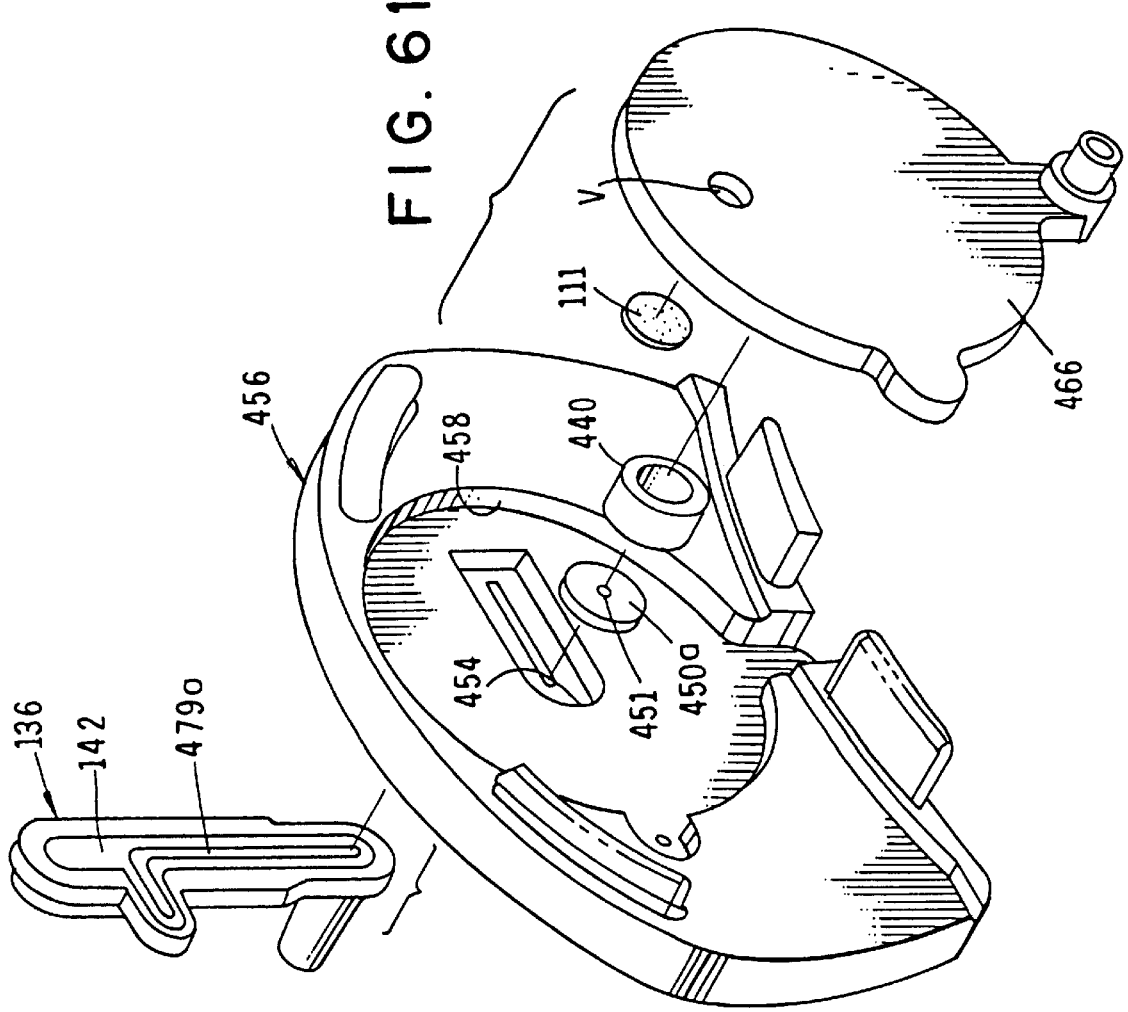

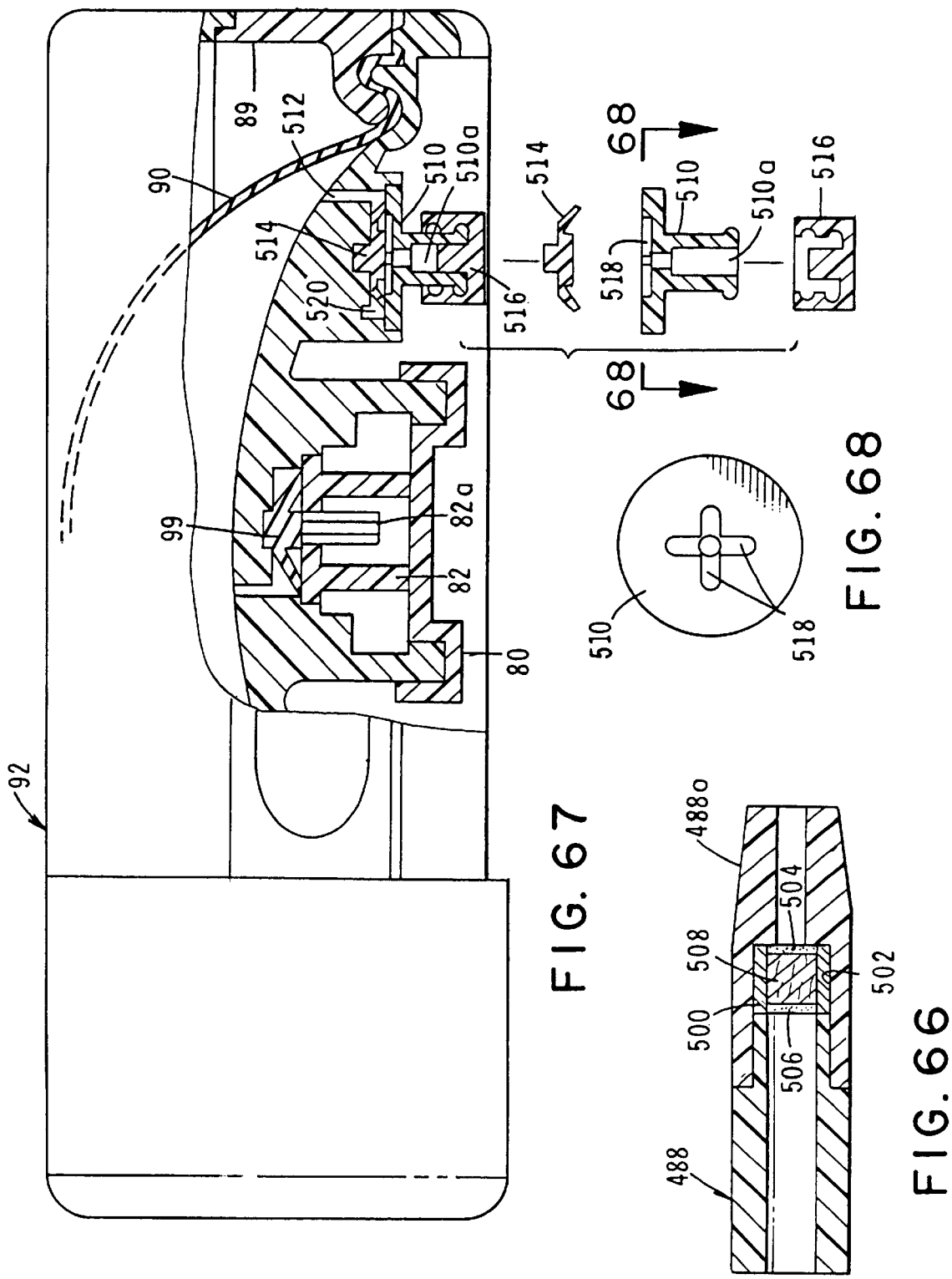

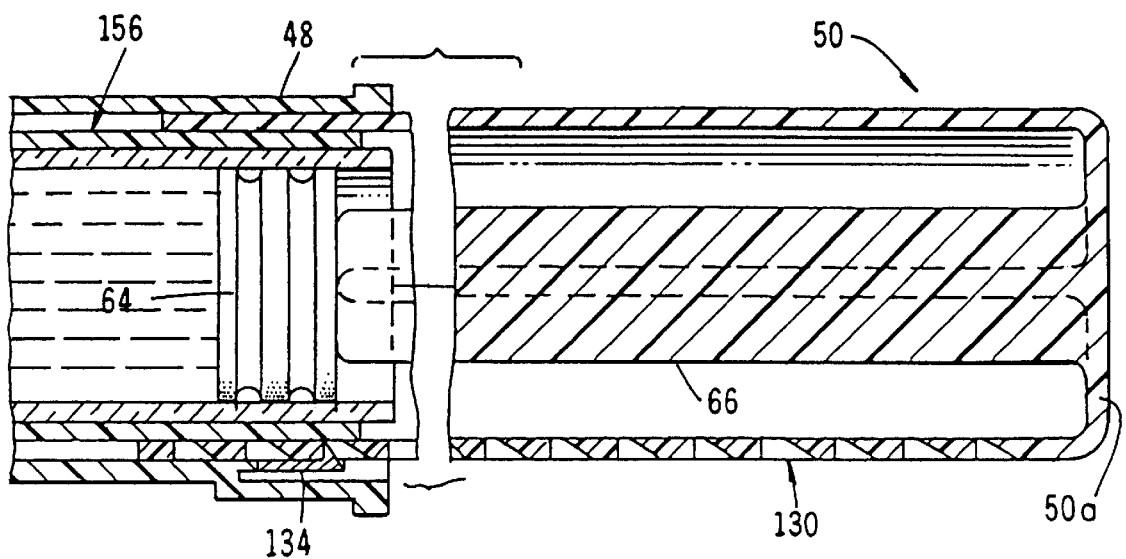
F I G. 71A

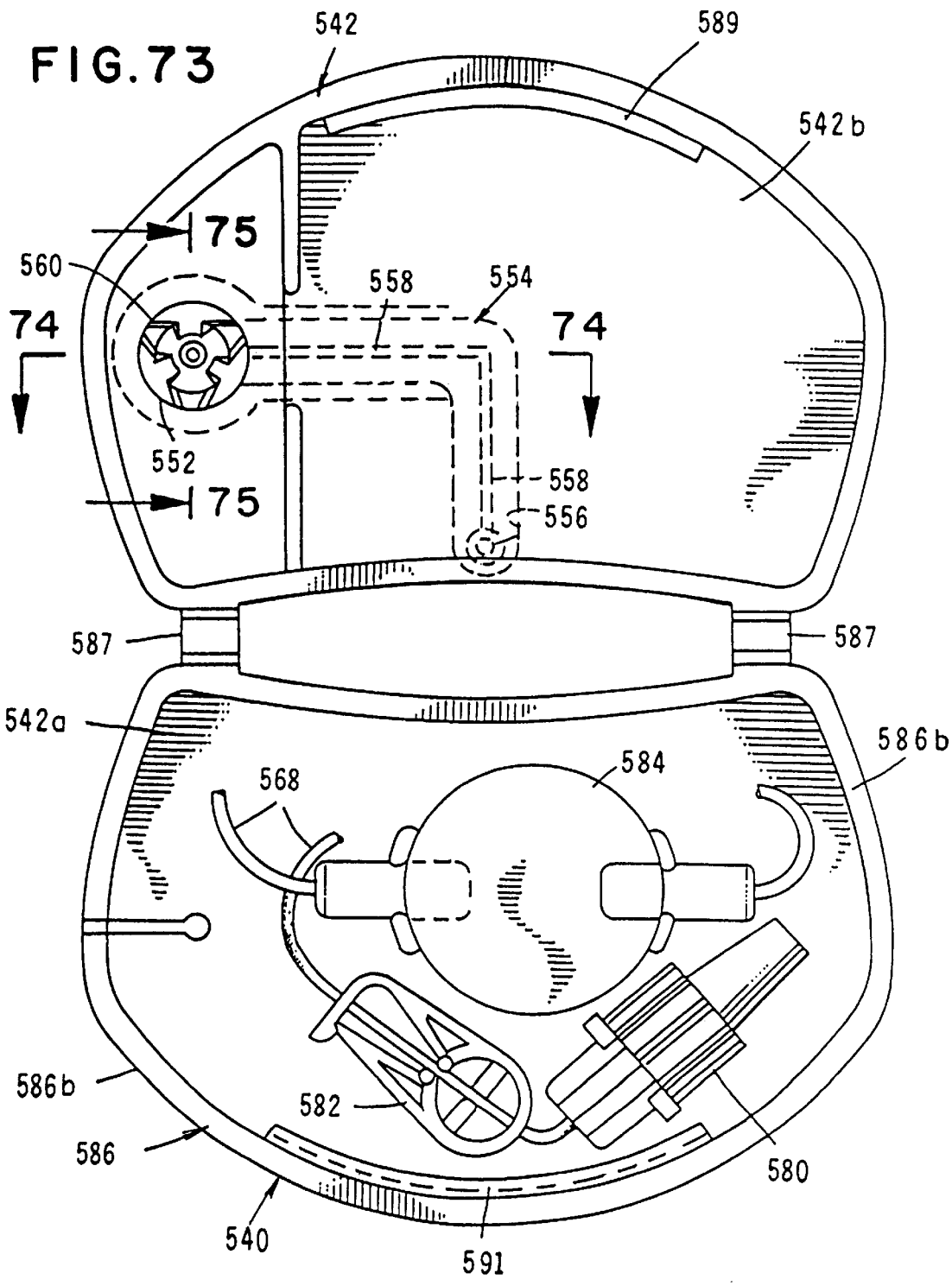

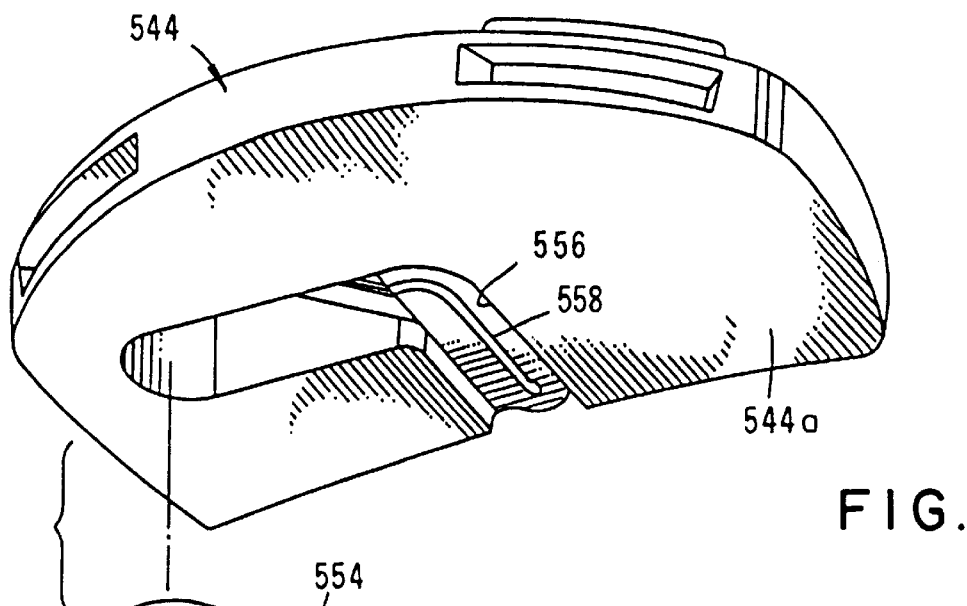
FIG. 78
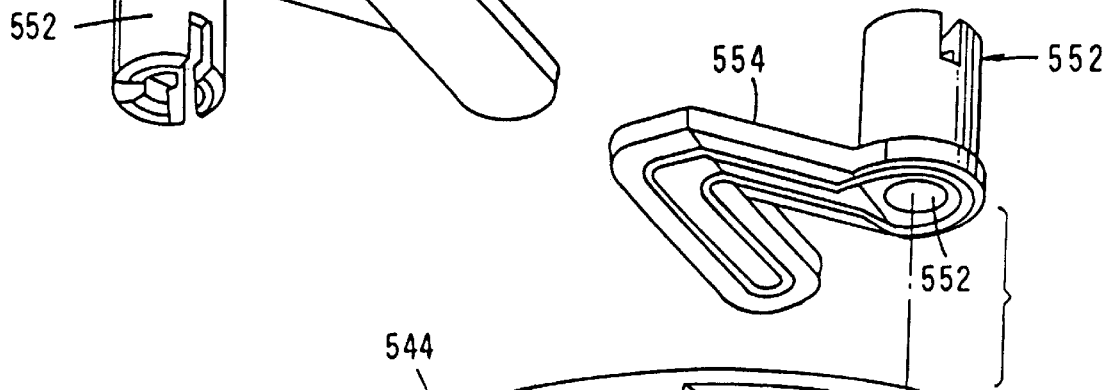
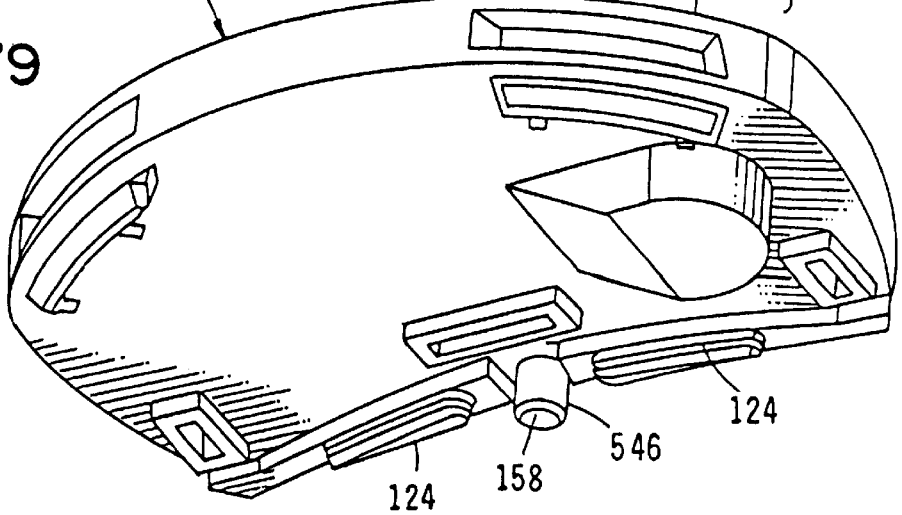
FIG. 79

FLUID DELIVERY APPARATUS WITH RESERVOIR FILL ASSEMBLY

This is a Divisional application of co-pending application Ser. No. 09/017,047 filed Feb. 2, 1998 which is a Continuation-In-Part Application of Application, Ser. No. 08/718,686 filed Sep. 24, 1996, now U.S. Pat. No. 5,721,382 which is a Continuation-In-Part of co-pending application, Ser. No. 08/432,220, filed May 1, 1995.

BACKGROUND OF THE INVENTION

1. Field of the Invention

The present invention relates generally to fluid delivery devices. More particularly, the invention concerns an improved apparatus, including a fluid dispenser having visual flow indicator means, for infusing medicinal agents into an ambulatory patient at specific rates over extended periods of time and a novel reservoir fill assembly for controllably filling the reservoir of the fluid dispenser.

2. Discussion of the Invention

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films and similar materials, which, in cooperation with a base define a fluid chamber that contains the fluid which is to be dispensed. The elastomeric film membrane controllably forces fluid within the chamber into fluid flow channels provided in the base.

The elastomeric film materials used in the apparatus of the present invention, as well as various alternate constructions of the apparatus, are described in detail in U.S. Pat. No. 5,205,820 issued to the present inventor. Therefore, U.S. Pat. No. 5,205,820 is hereby incorporated by reference in its entirety as though fully set forth herein. Co-pending U.S. Ser. No. 08/718,686 filed by the present inventors on Sep. 24, 1996 also describes various alternate constructions and modified physical embodiments of the invention including the provision of a novel fluid actuated indicator means for visually indicating fluid flow from the device. This co-pending application is also hereby incorporated by reference in its entirety as though fully set forth herein.

The apparatus of the present invention can be used with minimal professional assistance in an alternate health care environment, such as the home. By way of example, devices of the invention can be comfortably and conveniently removably affixed to the patient's clothing or to the patient's body and can be used for the continuous infusion of antibiotics, hormones, steroids, blood clotting agents, analgesics including morphine, and like medicinal agents. Similarly, the devices can be used for I–V chemotherapy and can accurately deliver fluids to the patient in precisely the correct quantities and at extended microfusion rates over time.

SUMMARY OF THE INVENTION

It is an object of the present invention to provide an apparatus for delivering fluids at a precisely controlled rate which comprises a fluid dispensing component having a fluid reservoir for containing the fluids to be delivered and a reservoir fill component which can be removably interconnected with the fluid dispensing component. More particularly, it is an object of the invention to provide such an apparatus in which the reservoir fill component can be used to controllably fill the reservoir of the dispensing component and in which the dispensing component can be used for the precise infusion of pharmaceutical fluids to an ambulatory patient at controlled rates.

It is another object of the invention to provide an apparatus of the aforementioned character which is highly reliable and easy-to-use by lay persons in a non-hospital environment.

Another object of the invention is to provide an apparatus which can be factory prefilled with a wide variety of medicinal fluids or one which can readily be filled in the field shortly prior to use using the novel reservoir fill component which can be removably interconnected to the lower surface of the base of the fluid dispenser.

Another object of the invention is to provide an apparatus as defined in the preceding paragraph in which the reservoir fill assembly is uniquely designed to accept a vial component of conventional construction which is factory filled with the medicinal fluid to be delivered to the patient.

A further object of the invention is to provide an accurate and highly reliable fluid delivery device which can be manufactured inexpensively in large volume by automated machinery.

Another object of the invention is to provide a device of the character described in which the dispenser component embodies a highly novel fluid flow indicator that provides a readily discernible visual indication of fluid flow status through the device.

Another object of the invention is to provide a device of the character described in which the dispenser component includes a novel infusion means, or delivery line assembly, which can be conveniently stored within a forward compartment of the housing of the dispenser.

Another object of the present invention is to provide an apparatus of the aforementioned character in which the aforementioned reservoir fill assembly comprises a container subassembly which includes either a conventional factory-prefilled vial or alternatively a container that can be filled in the field with wide variety of medicinal fluids.

Another object of the present invention is to provide a fill assembly of the type described in the preceding paragraph in which the container of the container subassembly is partially received within a novel adapter subassembly that can readily be removably interconnected with the fluid dispensing device.

Another object of the invention is to provide an apparatus as described in the preceding paragraphs which includes locking means for locking the container subassembly to the adapter subassembly following filling of the fluid reservoir of the fluid dispenser.

Another object of the invention is to provide a novel reservoir fill assembly for use with the fluid dispenser subassembly of the apparatus which is easy to use, is inexpensive to manufacture, and one which maintains the container in a substantially aseptic condition until time of use.

Other objects of the invention are set forth in U.S. Pat. No. 5,205,820 which is incorporated herein and still further objects will become more apparent from the discussion which follows.

By way of summary, the fluid delivery apparatus of the present form of the invention comprises two cooperating assemblies, namely a fluid dispenser and a reservoir fill assembly which can be removably coupled with the lower surface of the base of the fluid dispenser for filling the fluid reservoir of the fluid dispenser. The fluid dispenser, which readily lends itself to automated manufacture, is generally similar to that described in copending Ser. No. 08/718,686 and includes a base and a stored energy means comprising at least one distendable elastomeric membrane which cooperates with the base to form a fluid reservoir. In one form of the invention, the fluid dispenser includes a highly novel fluid flow indicator means which comprises a mechanical fluid flow indicator that provides a clear visual indication of normal fluid flow and absence of fluid flow from the fluid reservoir. In another form of the invention, the fluid dispenser includes a novel infusion apparatus which can be conveniently stored within a forward compartment of the housing of the fluid dispenser.

BRIEF DESCRIPTION OF THE DRAWINGS

FIG. 1 is a generally perspective, bottom view of one form of the fluid dispenser of the invention.

FIG. 2 is an enlarged bottom plan view of the device shown in FIG. 1.

FIG. 3 is a cross-sectional view taken along lines 3—3 of FIG. 2.

FIG. 4 is an enlarged side-elevational view of the device shown in FIG. 1, partly broken away to show internal construction.

FIG. 4A is a cross-sectional exploded view of the dispenser connector element and umbrella valve of the fluid dispenser which controls fluid flow toward the reservoir of the dispenser.

FIG. 4B is a view taken along lines 4B—4B of FIG. 4A.

FIG. 5 is a cross-sectional view of the removable cover which seals the inlet port of the fluid delivery apparatus.

FIG. 6 is a generally perspective view of the adapter portion of the reservoir fill assembly of the apparatus of the invention.

FIG. 18 is a generally perspective, exploded view of the down-stream portion of one form of the fluid dispensing apparatus of the invention showing the flow indicator means and a portion of the flow control means.

FIG. 19 is a generally perspective, exploded view of one form of the fluid flow control assembly illustrating its laminate construction.

FIG. 22 is a cross-sectional view taken along lines 22—22 of FIG. 20.

FIG. 23 is a cross-sectional view showing the indicator means of the invention in its starting configuration.

FIGS. 30 and 30A comprise, when taken together, an enlarged, cross-sectional view of an alternate form of the apparatus of the invention which includes a dual vial reservoir fill assembly.

FIG. 31A is a fragmentary top plan view of a portion of one of the pusher sleeves of the apparatus shown in FIG. 30A.

FIG. 31B is a fragmentary top plan view of a portion of the other pusher sleeve of the apparatus shown in FIG. 30A.

FIG. 32 is an enlarged, exploded, cross-sectional view of an alternate form of the dispenser connector and fill assembly connector of the invention.

FIG. 33A is an enlarged, exploded, cross-sectional view of an alternate form of fill assembly cannula construction usable with one of the vial subassemblies thereof.

FIG. 33B is an enlarged, cross-sectional view of the area identified in FIG. 30 by the numeral 33B.

FIG. 34 is an exploded, cross-sectional view of the reservoir fill assembly of this latest form of the invention.

FIG. 35 is an generally perspective view of one of the locking tabs of the locking means of this latest form of the invention.

FIG. 36 is a cross-sectional view taken along lines 36—36 of FIG. 34.

FIG. 37 is a view taken along lines 37—37 of FIG. 34.

FIG. 38 is a view taken along lines 38—38 of FIG. 34.

FIG. 39 is a cross-sectional view taken along lines 39—39 of FIG. 34.

FIG. 40 is a view taken along lines 40—40 of FIG. 34.

FIG. 48 is an enlarged, cross-sectional, exploded view of the coupler mechanism of this latest form of the invention.

FIG. 49 is an exploded, cross-sectional view of an alternate form of coupling mechanism for coupling together the dispenser component and the reservoir fill component.

FIG. 50 is an exploded cross-sectional view of still another form of coupling mechanism for coupling together the dispenser component and the reservoir fill component thereof.

FIG. 51 is a generally perspective, exploded view of the alternate form of reservoir fill assembly of the apparatus of the invention shown in FIG. 46.

FIG. 52 is a generally perspective, fragmentary view of the forward end of the reservoir fill assembly shown in FIG. 51 illustrating the construction of the closure caps of the assembly.

FIG. 53 is a cross-sectional view of yet another form of the reservoir fill assembly of the apparatus of the invention.

FIG. 54 is a cross-sectional view taken along lines 54—54 of FIG. 53.

FIG. 55 is a view taken along lines 55—55 of FIG. 53 partly broken away to show internal construction.

FIG. 56 is a cross-sectional view taken along lines 56—56 of FIG. 55.

FIG. 57 is a view taken along lines 57—57 of FIG. 56.

FIG. 58 is a cross-sectional view taken along lines 58—58 of FIG. 59

FIG. 59 is a view taken along lines 59—59 of FIG. 58.

FIG. 60 is an exploded, generally perspective, fragmentary view similar to FIG. 21 illustrating an alternate form of dispenser fluid flow control means.

FIG. 60A is an enlarged, cross-sectional view of a generally tubular shaped, elastomeric seal which, as shown in FIG. 60, is disposed proximate a rate control wafer which forms a part of the dispenser flow control means of this latest embodiment of the invention.

FIG. 60B is an enlarged, cross-sectional view of the elastomeric seal shown in FIG. 60A, but housing a novel rate control frit which forms a part of an alternate form of the dispenser flow control means of the invention.

FIG. 61 is an exploded, generally perspective, fragmentary view similar to FIG. 60 but further illustrating the alternate form of dispenser flow control means of this latter form of the invention.

FIG. 62 is an enlarged, cross-sectional view taken along lines 62—62 of FIG. 60 showing the flow control elements exploded from housing within which they are mounted.

FIG. 66 is a greatly enlarged, cross-sectional view of the connector fitting of the delivery line assembly which houses the rate control frit of the dispenser fluid flow control means of the invention.

FIG. 67 is an exploded, side-elevational view similar to FIG. 4 but showing an alternate form of dispenser component of the present invention and being partly broken away to illustrate alternate reservoir filling means comprising a luer fitting type connector for use in filling the reservoir of the dispenser component.

FIG. 68 is a view taken along lines 68—68 of FIG. 67 showing the fluid flow passageways of the connector.

FIG. 73 is a front view of the apparatus illustrated in FIG. 72 showing the delivery line assembly storage compartment of the dispenser in an open configuration.

FIG. 78 is an exploded, generally perspective front view of the support structure of the fluid delivery apparatus of the form of the invention shown in FIGS. 69 and 70.

FIG. 79 is an exploded, generally perspective, rear view of the components shown in FIG. 78.

DESCRIPTION OF THE INVENTION

Figure 7:
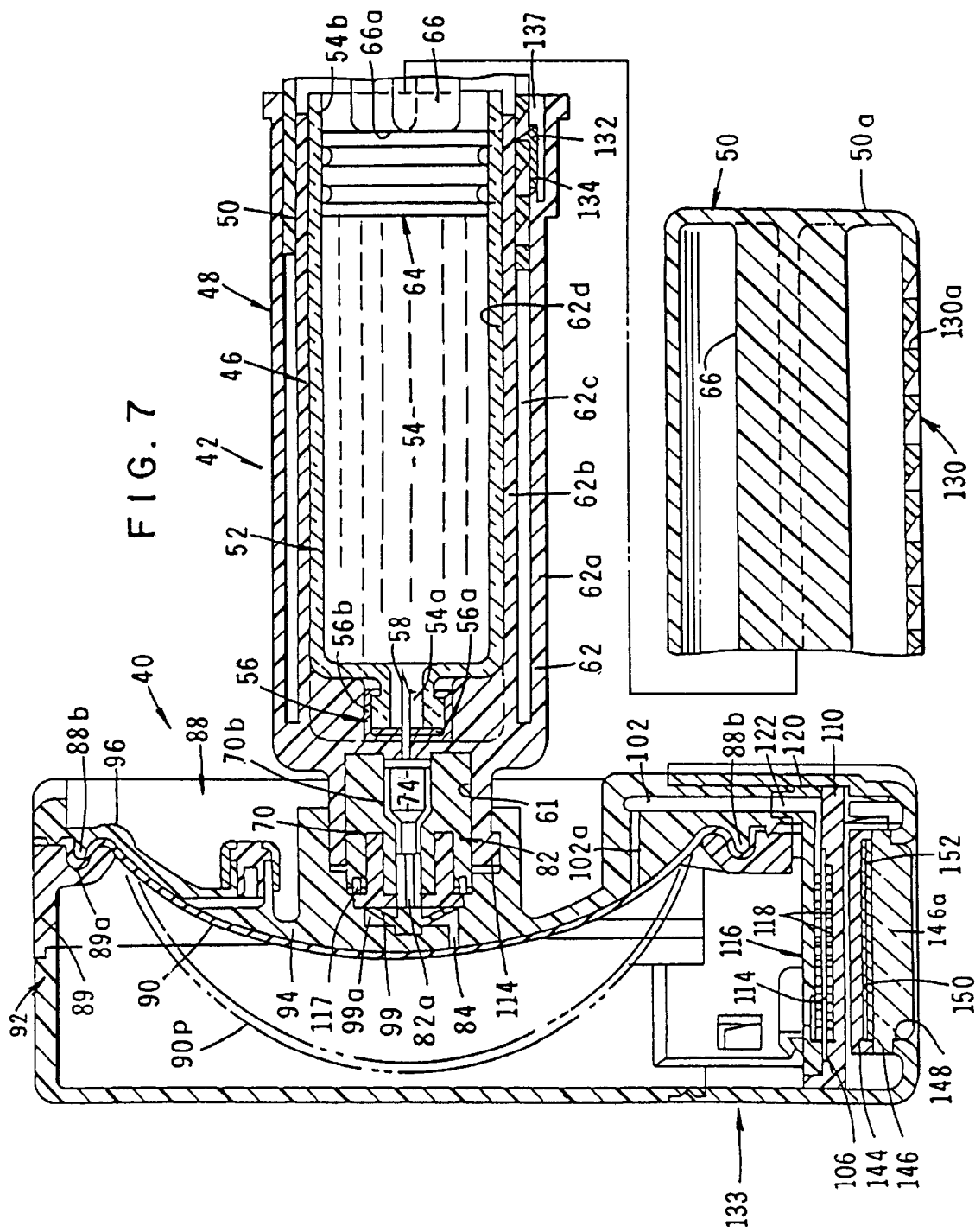
FIG. 7 is an enlarged, cross-sectional view of the fluid dispenser of the invention shown operably mated with one form of the reservoir fill assembly.
Figure 8:
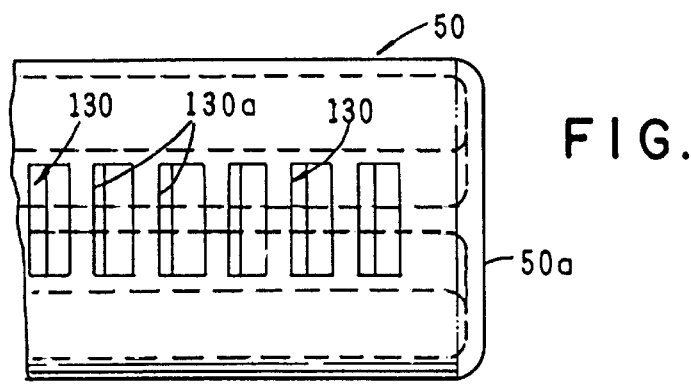
FIG. 8 is a fragmentary top plan view of a portion of the adapter sleeve of the reservoir fill assembly showing the locking teeth formed thereon.

Referring to the drawings and particularly to FIGS. 1 through 7, one form of the apparatus of this latest form of the present invention is there illustrated. As best seen in FIG. 7, the apparatus here comprises two major cooperating assemblies, namely a fluid dispensing apparatus or fluid dispenser 40 and a reservoir fill assembly 42 which can be operably coupled with fluid dispenser 40. As will be described in greater detail hereinafter, dispenser 40 is made up of three major cooperating subassemblies namely, a reservoir subassembly, a flow rate control subassembly, and a flow indicator subassembly.

Figures 16, 17:
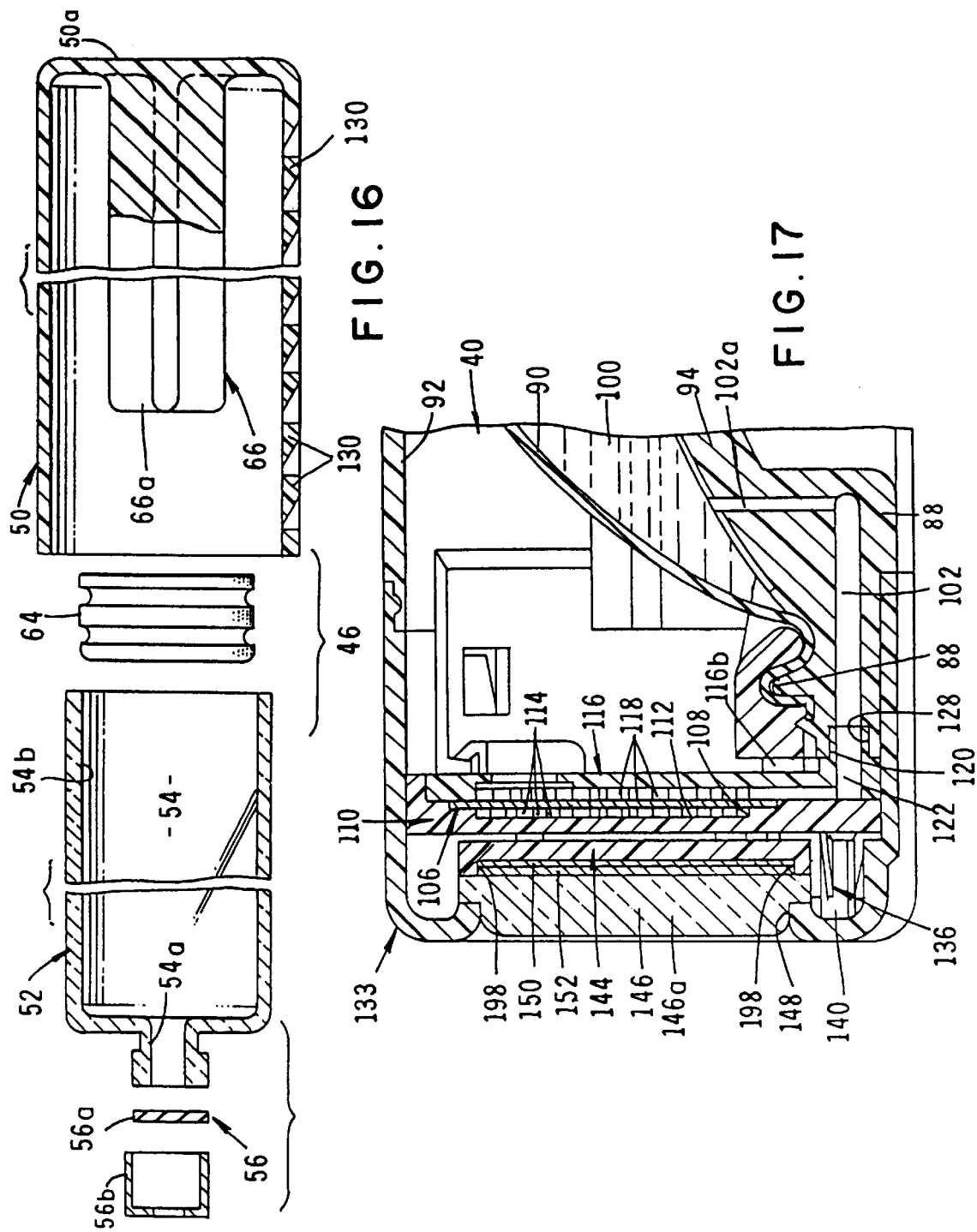
FIG. 16 is an enlarged, cross-sectional, exploded view of the rear portion of the reservoir fill assembly of the apparatus of the invention.
FIG. 17 is an enlarged, fragmentary, cross-sectional view of the forward portion of the dispensing unit illustrating the construction of one form of the flow indicator means and flow control means of the invention.

Turning particularly to FIGS. 9 through 16, the novel reservoir fill assembly 42 of the invention can be seen to also comprise three major components, namely a container subassembly 46 (FIG. 16), an adapter subassembly 48 (FIG. 9) and an adapter or pusher sleeve 50 (FIG. 16). Container subassembly 46 includes a container such as a vial 52 which contains the medicinal fluid with which the reservoir of the dispensing apparatus is to be filled. Adapter subassembly 48 functions to interconnect the fill assembly with the medicament dispenser in the manner presently to be described so that fluid can be transferred from container 52 to the reservoir of the dispenser component.

Figure 9:
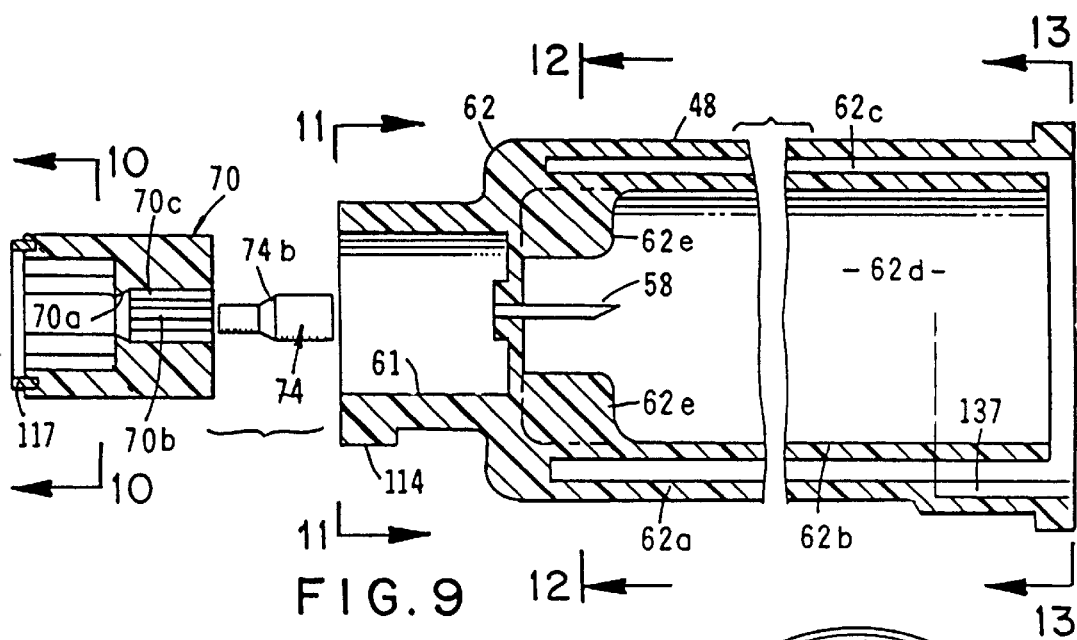
FIG. 9 is an enlarged, cross-sectional, exploded view of the adapter subassembly of the reservoir fill assembly.

As best seen in FIG. 16, container 52 includes a fluid chamber 54 having first and second open ends 54a and 54b. First open end 54a is sealably closed by closure means, here provided in the form of septum assembly 56 which includes a pierceable septum 56a and a clamping ring 56b for connecting the septum to the container proximate open end 54a. Septum 56a is pierceable by the cannula means or cannula 58 of the adapter subassembly 48. Septum 56a and cannula 58 form a part of the fill flow control means of the invention for controlling fluid flow toward the dispenser component 40. As shown in FIG. 9, cannula 58 is mounted centrally of an end wall 60 of body 62 of the adapter subassembly.

To expel fluid from fluid chamber 54 of the vial assembly and into cannula 58 of the adapter subassembly and thence into the fluid reservoir of the dispenser unit, displacement means are provided. This displacement means here comprises a plunger 64 which is telescopically movable within chamber 54 by pusher sleeve subassembly 50. To accomplish this movement, sleeve assembly 50 is provided with pusher means shown here as a pusher rod 66 which is integrally formed with end wall 50a of sleeve 50 (see also FIG. 7).

Referring particularly to FIGS. 7 and 9, it is to be noted that body 62 of adapter subassembly 48 uniquely includes outer and inner, generally cylindrically shaped walls 62a and 62b which define therebetween an elongated annular space 62c and within which sleeve component 50 is slidably received. As shown in FIG. 7, container assembly 46 is closely receivable within a chamber 62d formed internally of wall 62b of the adapter subassembly and can be urged forwardly of chamber 62d by inward telescopic movement of sleeve 50 into space 62c. More particularly, as indicated in FIG. 7, the inboard end 66a of pusher rod 66 engages plunger 64 and urges it inwardly of reservoir 54 as sleeve 50 is moved inwardly of annular space 62c.

Figure 10:
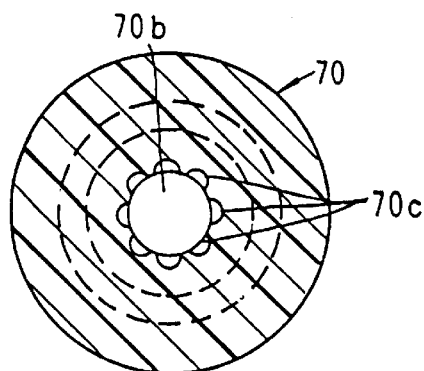
FIG. 10 is a cross-sectional view taken along lines 10—10 of FIG. 9.
Figure 11:
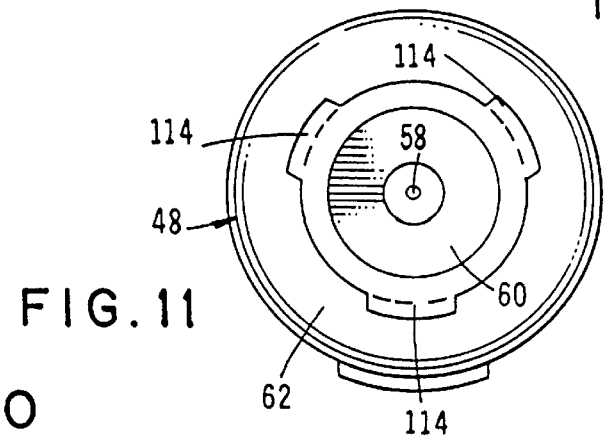
FIG. 11 is a view taken along lines 11—11 of FIG. 9.
Figure 12:
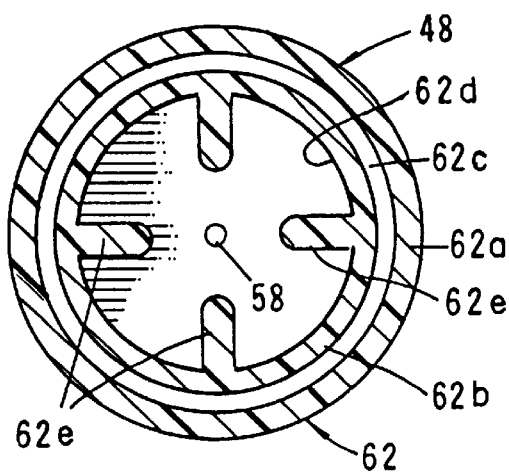
FIG. 12 is a cross-sectional view taken along lines 12—12 of FIG. 9.
Figure 13:
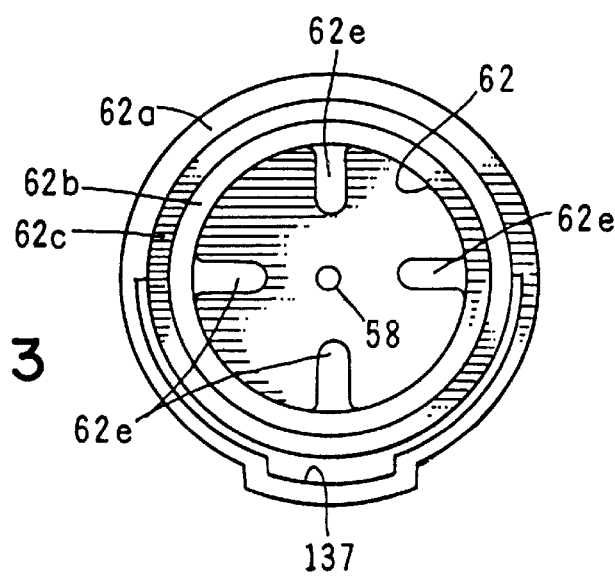
FIG. 13 is a view taken along lines 13—13 of FIG. 9.
Figure 14:
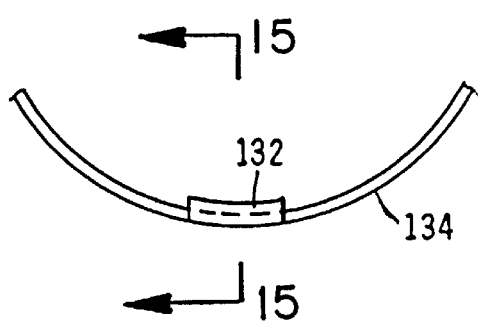
FIG. 14 is an end view of the locking tab portion of the locking means of the invention for locking the pusher sleeve subassembly of the reservoir fill assembly to the adapter component thereof.
Figure 15:
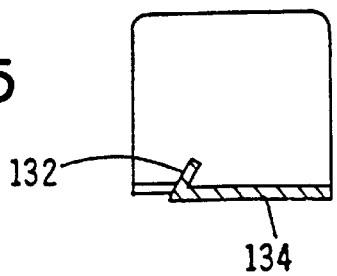
FIG. 15 is a cross-sectional view taken along lines 15—15 of FIG. 14.

During the initial mating of sleeve 50 with adapter subassembly 48, the resistance of the fluid within chamber 54 will resist movement of plunger 64 inwardly of reservoir 54 so as to cause the entire vial cartridge assembly to initially move inwardly of chamber 62d to a position wherein septum 56a is engaged by cannula 58 of the adapter subassembly. As shown in FIGS. 12 and 13 guide ribs 62e formed interiorly of chamber 62d, guide the neck portion of the vial toward cannula 58. A continued inward force on sleeve 50 will cause cannula 58 to pierce septum 56a in the manner shown in FIG. 7, thereby opening fluid communication between reservoir 54 of vial 52 and the internal fluid passageway of cannula 58. Once septum 56a has been pierced, pusher rod 66 will urge plunger 64 forwardly of reservoir 54 from a first location proximate open end 54b to a second location proximate end 54a. As plunger 64 moves forwardly of reservoir 54, fluid within the reservoir will be caused to flow into the central fluid passageway of cannula 58 and toward additional components of the flow control means of the invention which controls fluid flow toward the fluid dispenser component 40. These further flow control means include valve means comprising a support assembly of the character shown in FIG. 9 and generally designated by the numeral 70. Valve support assembly 70 is held within a counterbore 61 formed in body 62 and in close proximity with wall 60 of adapter subassembly 48 by any suitable means such as sonic welding. Member 70 includes a valve seat 70a and a centrally disposed fluid passageway 70b which is defined by a plurality of circumferentially spaced fluid flow grooves 70c (FIG. 10). Disposed within passageway 70b is a check valve 74 which also forms a part of the valve means for controlling fluid flow from cannula 58 toward the fluid reservoir of the dispenser assembly. Check valve 74 is designed to permit fluid flow toward dispenser 40 but blocks fluid flow in the opposite direction. As shown in FIG. 9, check valve 74, which is of conventional construction, includes a body portion 74a and a seat portion 74b which sealably engages seat 70a when valve 74 is in a closed position. The construction and operation of valve 74 is well understood by those skilled in the art and the manner of opening the valve during the filling step will presently be described.

Prior to use, the adapter subassembly component 48 of the reservoir fill assembly 42 is maintained in a protected and substantially sterile configuration by tear-away end caps 76 and 78 (see FIG. 6). As indicated in FIG. 6, tearaway end cap 76 is receivable over and closes the forward end of adapter subassembly 48, while tear-away end cap 78 is received over and closes the rearward open end portion of adapter subassembly 48. Similarly, as shown in FIGS. 4 and 5, a tear-away cap 80 is received over and closes the dispenser connector subassembly 82 and inlet 84 of the dispenser assembly 40. Cap 80 maintains the dispenser connector and fluid inlet passageway of the device in a closed and substantially sterile condition.

Turning again to FIGS. 1 through 4, the fluid dispenser assembly 40 of the apparatus of this form of the invention is similar in many respects to that described in Ser. No. 08/718,686 and includes a housing assembly comprising a base 88, a capture ring 89, a stored energy source, or distendable membrane 90 and a cover 92 for enclosing the stored energy source, the capture ring and the base. The base 88 includes an ullage defining protuberance 94 and a membrane capture portion 96. Disposed between base 88 and cover 92 is the membrane capture ring 89 which has a bottom opening 89a which receives protuberance 94 of base 88 (see FIG. 3).

Referring particularly to FIGS. 3, 4, and 7, base 88 comprises, in addition to the distendable member engaging protuberance, or ullage 94, the previously identified dispenser connector subassembly 82, to which the reservoir fill assembly 42 is interconnected in the manner shown in FIG. 7. Base 88 also includes an upstanding tongue 88b which extends about the perimeter of the base and is closely receivable within groove 89b formed in the capture ring 89 (FIG. 3). When the base 88 and the membrane capture ring 89 are assembled in the manner shown in FIG. 3, the periphery of distendable membrane 90 will be securely clamped within groove 89b by tongue 88b. After the parts are thus assembled, base 88 is bonded to capture ring 89 by any suitable means such as sonic bonding which also functions to simultaneously trim membrane 90. This done, cover 92 is mated with capture ring 89 in the manner shown in the drawings and is suitable bonded in place. Cover 92 can, if desired, be constructed from a substantially transparent plastic material which is impermeable to fluids, including gases.

During the reservoir filling step, the details of which will presently be described, fluid under pressure will flow into inlet passageway 84 of the fluid dispenser via an umbrella valve 99 and thence into a reservoir 100 which is formed between protuberance 94 and distendable membrane 90p which is shown in phantom lines in FIG. 7. As the fluid under pressure flows into the reservoir, it will cause membrane 90 to distend outwardly from protuberance 94 in the manner shown by the phantom lines in FIG. 7. While the stored energy means can be in the form of a single prestressed or unstressed isotropic, elastomeric distendable membrane, such as membrane 90, it can also be constructed as a laminate assemblage made up of a plurality of initially generally planar distendable elements of films. Such construction is described in Ser. No. 08/718,686, which application is incorporated herein by reference. During the infusion step, internal stresses formed in membrane 90 will cause it to move toward protuberance 94 and fluid within reservoir 100 will be uniformly and controllably forced outwardly through a passageway 102a and then through a passageway 102 formed in base 88 (FIG. 7) in a direction toward the fluid flow indicator means of the invention.

Turning to FIGS. 7, 17, 18 and 19, the important dispenser flow control means of the dispenser component of the present form of the invention is there shown. This means, which is disposed externally of reservoir 100, functions to control fluid flow outwardly of the device. In the embodiment of the invention shown in FIGS. 18 and 19, the dispenser flow control means 106, which includes a fluid flow rate control means, is closely received within a cavity 108 formed in a support means, shown here as a membrane support structure 110. The downstream wall 112 of cavity 108 is provided with fluid distribution means comprising a multiplicity of circumferentially spaced, manifolding stand-off elements 114 against which assembly 106 is held in engagement by a disc-like member 116 (FIG. 21) which is receivable within recess 108 in the manner shown in FIG. 17. Member 116 is provided with fluid collection means shown here as a multiplicity of circumferentially spaced, manifolding stand-offs 118 (FIG. 21) which engage assembly 106 when member 116 is in position within cavity 108 (see FIG. 17). More particularly, when member 116 is in place within cavity 108, the fluid flow control means is bonded at its circumference to member 110 and securely positioned between stand-offs 114 and 118 which cooperate to define a multiplicity of concentric and radial extending fluid passageways, which function to direct flow through the fluid flow control means. A vent patch 111 vents to atmosphere any air trapped within the fluid passageways (FIG. 21).

As best seen in FIG. 19, the flow control means here comprises a laminate construction made up of layers 106a, 106b, 106c, 106d, 106e, and 106f. More particularly, layer 106a comprises first filter for initially filtering the fluid, while layer 106b comprises a second filter for providing a second, more refined, filtering of the fluid. Layer 106c is here shown as a first flow rate control membrane for controlling flow at a first rate. Layer 106e is a second flow rate control membrane for controlling flow at a second rate. Disposed intermediate rate control membranes or layers 106c and 106e is a distribution means or porous distribution layer for distributing the fluid flowing through membrane 106c across the surface of membrane 106e. Layer 106f comprises a porous support member for supporting membrane 106e. Reference should be made to copending Ser. No. 08/718,686 for a more detailed description of the operation of the flow control means and for a discussion of the materials suitable for constructing various components of the flow control means.

Figure 21:
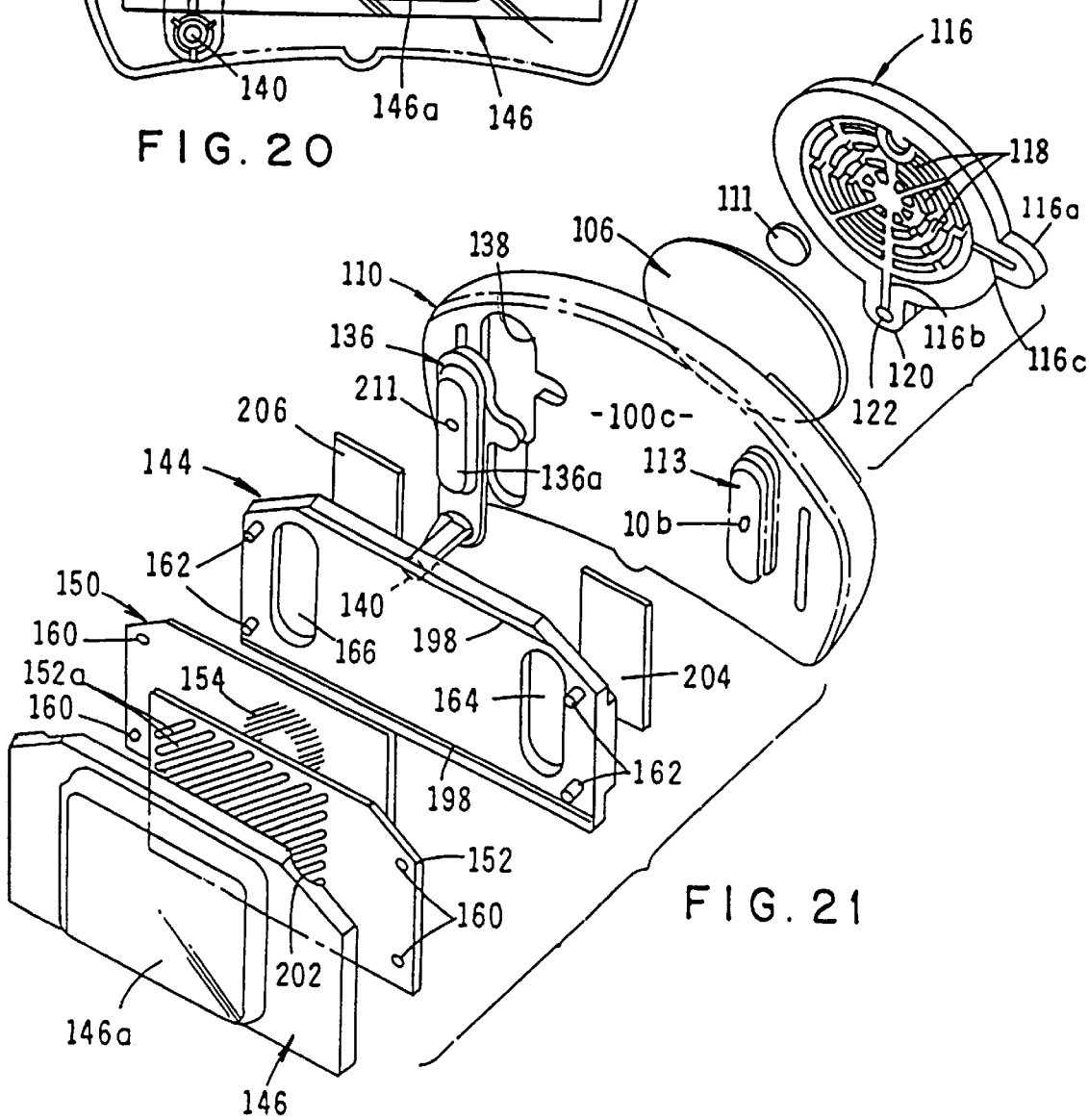
FIG. 21 is a generally perspective exploded view of one form of forward housing portion of the apparatus of the invention showing the flow indicator means and a portion of the flow control means.

As best seen in FIG. 21, member 116 includes a downwardly extending fluid inlet leg or segment 120 which is provided with a fluid passageway 122. Passageway 122 is adapted to communicate with cavity 108 when member 116 is mated with support structure 110. Formed on either side of the central portion of the support structure 110, are wing-like protuberances 124 that are received within spaced-apart, arcuate-shaped cavities (not shown) formed in the base 88. Also formed in base 88 is a socket 128 which closely receives the inboard end of segment 120 (FIG. 17). Located proximate the upper edge of support structure 110 are spaced-apart capture grooves 132, which attach an indicator cover 133 to structure 110. Indicator cover 133, is, in turn, connected to cover 92 by any suitable means in the manner best seen in FIG. 17. Copending Ser. No. 08/718,686 provides further details concerning the construction of indicator cover 133 and its attachment to cover 92.

Figure 20:
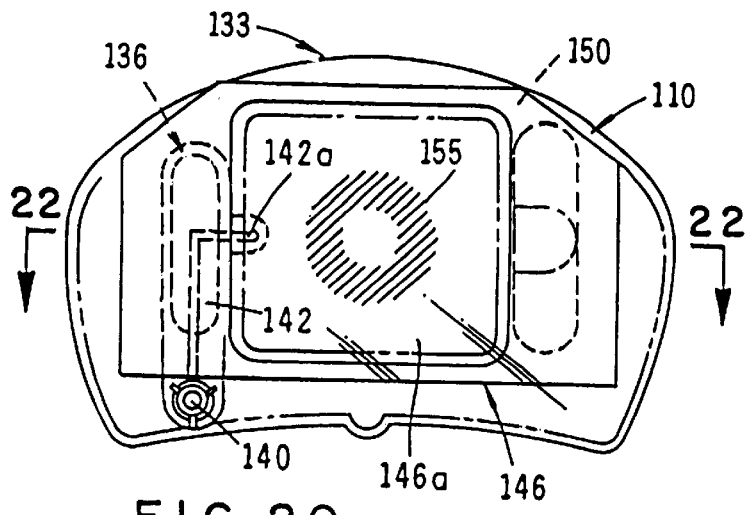
FIG. 20 is a front view of the housing portion of the flow indicator means of the invention.

As shown in FIG. 17, when the fluid flow control subassembly is mated with the reservoir assembly, fluid inlet passageway 122 of member 116 is placed in fluid communication with reservoir 100 via passageways 102 and 102a. With this construction, when fluid is forced into passageway 102a by the stored energy means, the fluid will flow into passageway 102, then into passageway 122 of member 116, and finally into chamber 108 formed in member 110 via the fluid passageway 116b. As the fluid under pressure flows into the upstream portion of chamber 108 behind flow control assembly 106, it will be distributed by stand-offs 118 so that it will uniformly flow through assembly 106 and toward the fluid outlet port of the flow control subassembly. As best seen in FIG. 21, the outlet port here comprises a uniquely shaped assembly 136 which is receivable in a cavity 138 formed in the back or downstream wall 100c of substrate 110. Assembly 136 includes a fluid outlet 140 and an internal chamber 142 having an actuator fill port 142a (FIG. 20), the purpose of which will presently be described.

Considering next the very important flow indicator means of the invention. This novel means visually distinguishes among three conditions of operation, namely normal fluid flow, fluid flow blockage or occlusion, and reservoir empty. Turning to FIG. 18, the flow indicator means here comprises an indicator base or platform 144 and a support or lens plate 146. As shown in FIG. 17, platform 144 and plate 146 are housed within indicator cover 133. As seen in FIG. 21, plate 146 has a viewing lens portion 146a which indexes with an opening 148 provided in indicator cover 133.

Figure 24:
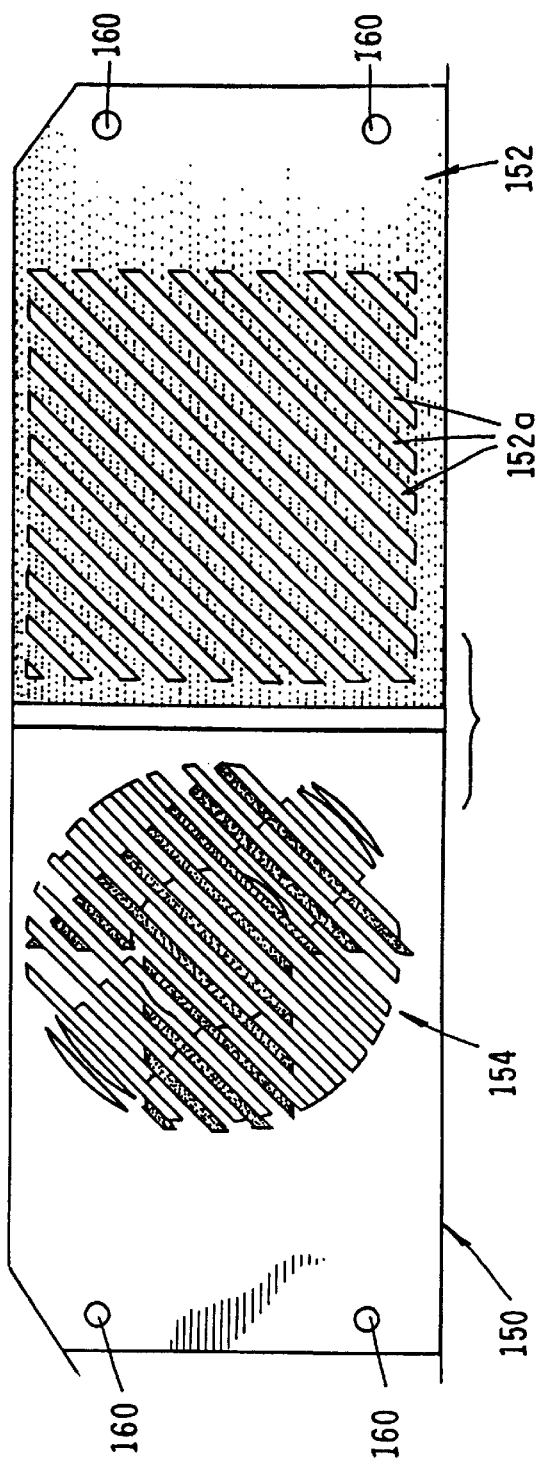
FIG. 24 is an enlarged plan view of the indicia carrying thin films of the flow indicator means of the apparatus of the invention.

Disposed between platform 144 and lens plate 146 are first and second indicia-carrying means shown here as thin films. These films, which are identified in FIGS. 18 and 21 as 150 and 152, are in intimate contact and are constructed from a substantially transparent, flexible polymer material such as mylar. The downstream surface of the inferior or first film 150 is printed with three integrated symbols 154 (FIG. 24), namely a blue circle 155 (FIG. 25), a green arrow 157 (FIG. 27), and a red X 159 (FIG. 29), each consisting of diagonal strips of color printed in an alternating pattern (blue, green, red, blue, green red, and so on). The superior or second film 152 serves as a "mask" over the inferior film 150 and is printed with a pattern of diagonal alternating clear and opaque strips 152a that occur in a 1:2 ratio. The printed ratio of the superior "mask" allows only one colored symbol to appear at a time when viewed through viewing lens 146a in plate 146. The inferior and superior films are provided at their opposite ends with apertures 160 which receive retention pins 162 provided on platform 144 (FIG. 21) which permit attachment of the film to platform 144 in a manner such that the non-patterned portion of both the superior and inferior films are maintained in index. With this construction, each thin film is able to move in opposing directions parallel to the film plane with its range of motion limited to one axis in the film plane by edge guides 198 provided on platform 144 (FIG. 21). As the films move, the visible symbol pattern changes due to the transverse displacement of the patterns imprinted thereon.

Figure 26:
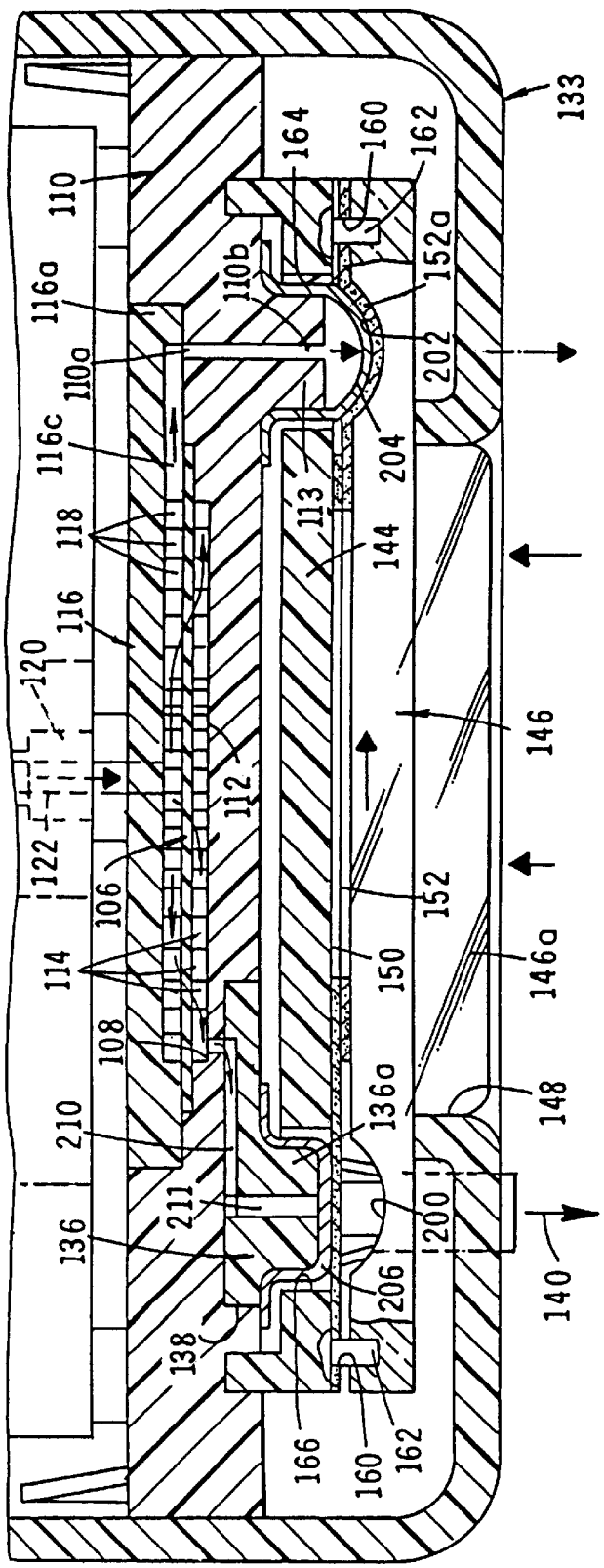
FIG. 26 is a cross-sectional view similar to FIG. 23 but showing the indicator means as it appears when fluid is flowing through the apparatus in a normal fashion.

Referring particularly to FIGS. 18, 23, and 26, it can be seen that support plate 146 is provided with transversely spaced, channel-like depressions 200 and 202 which index with slots 166 and 164 formed in platform 144 respectively when the components are assembled in the manner shown in the drawings. Aligned with the upstream side of slots 164 and 166 are mechanical actuator means, here provided as mechanical actuators or elastomeric elements 204 and 206. More particularly, the first actuator element 204 aligns with slot 164 and the second actuator element 206 aligns with slot 166.

Figure 27:
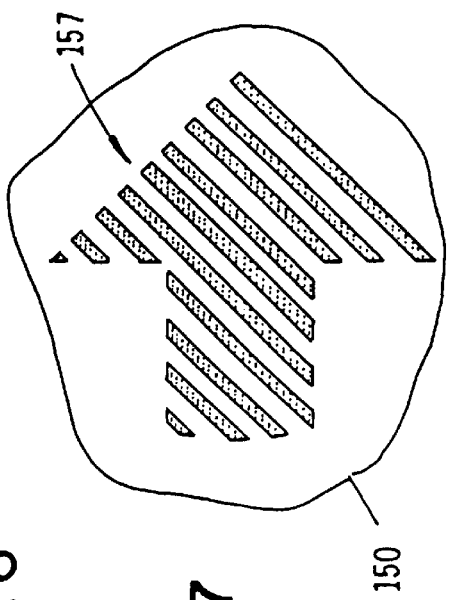
FIG. 27 is a fragmentary plan view of the symbol that is viewable by the user when the apparatus is in the configuration shown in FIG. 26.

In a manner presently to be described, the mechanical actuator means are deflected from their initial configuration whenever there is sufficient fluid pressure present within the fluid flow path to cause their outward deflection toward thin films 150 and 152. During operation the first mechanical actuator element 204 is deflected by fluid pressure of reservoir 100. More particularly, when there is sufficient fluid pressure in the fluid reservoir and fluid is being delivered by the stored energy means of the device, the first mechanical actuator means is deflected outwardly so as to urge the non-patterned portion 152a of indicator film 152 into expansion channel 202 (FIG. 26). As the film arches into channel 202, the printed portion of the film is transversely displaced a specific distance. This film displacement re-aligns the printed symbol patterns on the inferior film 150 with the mask pattern on the superior film 152 and results in a change of the symbol (in this case an arrow as shown in FIG. 27) that is visible through the support plate view aperture 146a.

Figure 28:
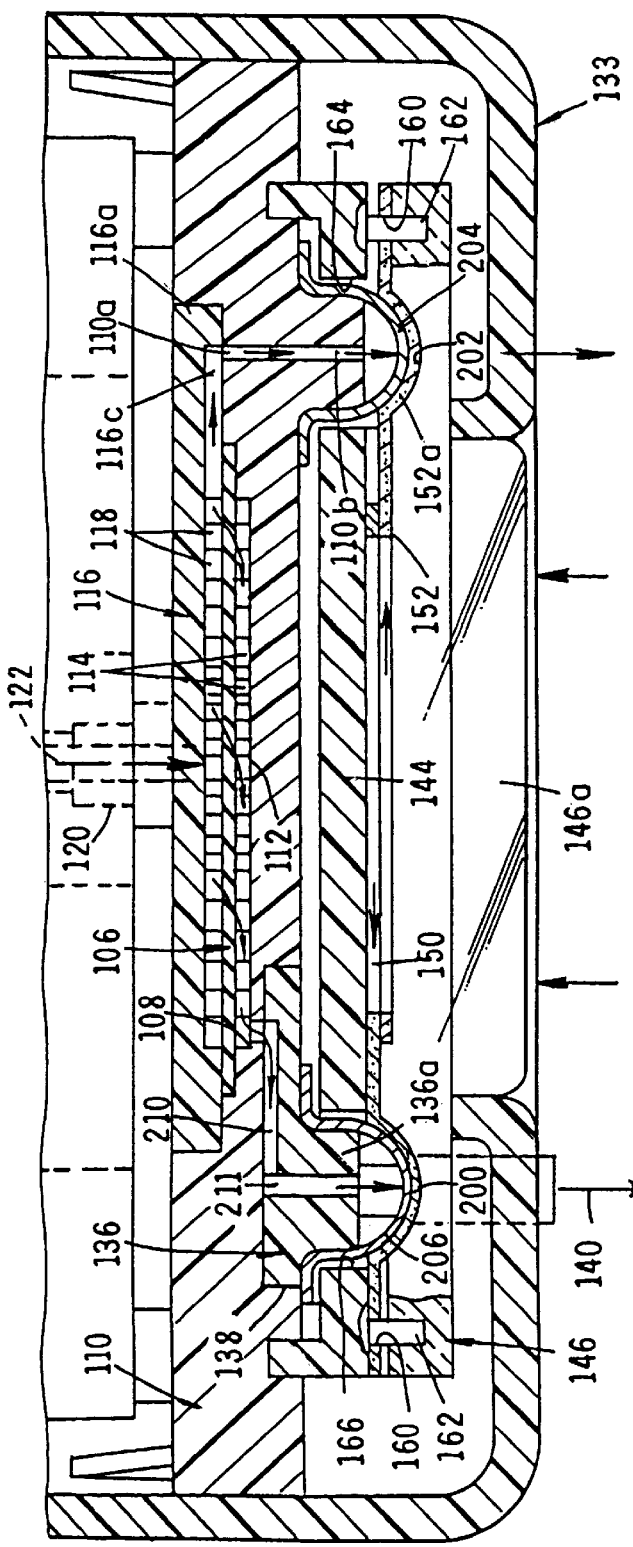
FIG. 28 is a cross-sectional view similar to FIG. 23 but showing the indicator means as it appears when there is a blockage downstream of the indicator means that prevents normal fluid flow.
Figure 29:
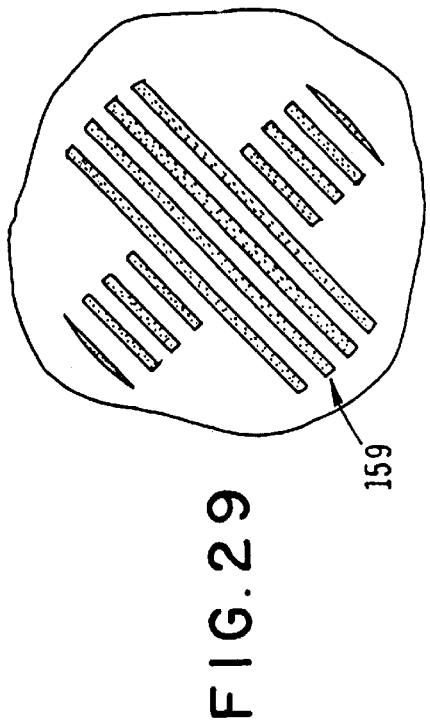
FIG. 29 is a fragmentary plan view of the symbol that is viewable by the user when the apparatus is in the configuration shown in FIG. 28.

As can be observed by referring to FIGS. 28 and 29, both the first and second mechanical elastomeric actuator elements 204 and 206 are inflated and deflected outwardly toward their respective extension channels when the device is filled and primed but not in a state of delivery or when there is a buildup of fluid pressure during delivery that is caused by blockage of the delivery line downstream from second mechanical actuator element 206. While element 204 can be deflected by normal line pressure, element 206 is deflected only by pressure buildup resulting from the downstream blockage. When both mechanical actuators are deflected outwardly in the manner shown in FIG. 28, both the superior and inferior films are displaced transversely to a second position revealing a second symbol, as for example, an X as viewed through the viewing aperture of the support plate (see FIGS. 28 and 29).

Figure 25:
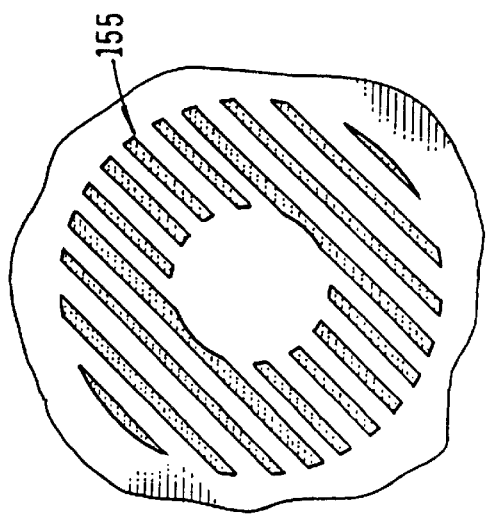
FIG. 25 is a fragmentary plan view of the symbol that is viewable by the user when the apparatus is in the configuration shown in FIG. 23.

A third alignment of symbol patterns as shown in FIGS. 23 and 25 is visible when the device is in an unfilled state or when the delivery line is open, the reservoir is empty and fluid delivery to the patient has been completed. In this case, there is no fluid pressure in the line on either the upstream or downstream side of the flow control means and thus both the first and second mechanical actuator elements are in a non-deflected position. In this condition, the inferior and superior films are not transversely displaced and thus exhibit a third combination of patterns resulting in a third symbol as, for example, a circle being visible through the viewing aperture of the support plate (see FIG. 25). Actuating elements 204 and 206 can be precisely tailored to deflect under various pressures thereby permitting great apparatus versatility.

In considering the method of operation of the device and the manner in which fluid flow though the device, reference should be made particularly to FIGS. 7 and 17. During the filling step, the fluid to be dispensed is introduced into reservoir 100 using the reservoir fill assembly 42. More particularly, fluid from container 52 will flow past the valve means of assembly 42, past umbrella valve 99 which is housed in an outlet port 99a and into reservoir 100 via inlet passageway 84. After filling and during the fluid dispensing step, the prestressed membrane 90 will tend to return toward a less distended configuration causing fluid within the reservoir to flow outwardly of reservoir 100, into passageway 102a and then into passageway 102. The fluid under pressure will next flow into passageway 122 of the inlet port of disc-shaped member 116. A portion of the fluid entering cavity or chamber 108 can by pass the fluid flow control assembly 106 and flow directly toward an ear-shaped extension 116a (FIG. 21) provided on member 116 via flow passageways 116b and 116c (see also FIG. 22). From passageway 116c, the fluid will flow under pressure into a passageway 110a formed in substrate 110 and toward passageway outlet 110b (FIG. 26). It is to be noted that passageway 110a extends through a protuberance 113 formed on substrate 110. This construction permits the fluid flowing into ear-shaped protuberance 116a to flow through passageway 110a and impinge directly upon flow indicator element 204 which sealably engages the protuberance, causing it to deform outwardly in a manner to force portion 152a of indicator film 152 to arch into expansion channel 202 (FIG. 26). This, in turn, will cause transverse displacement of indicator film 152 in the manner previously described.

As indicated in FIG. 28, fluid flowing through passageway 122 of disc-shaped member 116 will also be distributed over the upstream face of the flow control assembly 106 by the fluid distribution means, or protuberance 118 and will pass through the membrane at a predetermined controlled rate. The fluid flowing through the flow control means will be collected by the fluid collection means or protuberances 114 and then will flow into a passageway 210 (FIG. 28). The fluid will then flow outwardly of the device through fluid outlet 140 to which an appropriate infusion line can be connected. It is to be observed that a portion of the fluid flowing into outlet port assembly 136 is free to flow through passageway 211 provided in a protruding portion 136a thereof. If there is a blockage which prevents continued free fluid flow outwardly of the device through outlet 140 fluid, under pressure, will impinge upon indicator element 206 causing it to deflect outwardly in the manner shown in FIG. 28. This outward deflection of element 206 will urge a portion of indicator film 150 into receiving channel 200 of the lens plate causing transverse movement of film 150 so as to reposition film 150 relative to film 152. Should fluid flow into passageway 211 cease, indicator element 206 will return to its at rest position as will film 150. Similarly, if fluid flow from the reservoir ceases, film 152 will also return to its at rest position thereby once again causing the "O" symbol to be viewable through the viewing lens.

At the time of use of the apparatus of the invention, and with the adapter assembly 48 in the sealed condition shown in FIG. 6, closure cap 76 is first removed from the assembly. This done, the assembly can be mated with the dispenser apparatus 40 in the manner shown in FIG. 7 and lockably interconnected therewith by connector means which here comprises a bayonet type connector arrangement of the character best seen in FIGS. 2, 9, and 11. More particularly, as shown in FIG. 2, the connector boss on base 88 of the dispenser unit 40 is provided with a dispenser connector comprising a plurality of circumferentially spaced-apart tab receiving slots 88a. Similarly, the inboard end of the adapter subassembly 48 is provided with an adapter connector comprising a plurality of circumferentially spaced apart locking ears 114 (FIGS. 9 and 11) which are adapted to be received within slots 88a. With this construction, after locking ears 114 have been received within slots 88a, rotation of adapter subassembly 48 relative to the dispensing means will bring ears 114 into locking engagement with the dispenser unit thereby operably interconnecting the reservoir fill assembly with the dispenser unit 40. To enable smooth rotation of the adapter subassembly relative to the dispenser unit, an antilock elastomeric ring 117 is formed on the front face of member 70 (FIG. 9).

During mating of the adapter assembly 48 with the dispenser unit 40, a generally cross-shaped extension 82a provided on connector subassembly 82 functions as a valve operating means to move valve 74 of the valve means away from seat 70a. During mating, elastomeric ring 117 sealably engages connector subassembly 82 to form a substantially leak-tight seal.

With adapter subassembly 48 suitably mated with the dispenser apparatus 40, cap 78 is removed from the inboard end of adapter assembly 48 (FIG. 6) and the first end of vial assembly 46 is inserted into chamber 62d of adapter subassembly 48. With the vial cartridge assembly inserted into chamber 62d sleeve 50 is then mated with adapter assembly 48 in the manner shown in FIG. 7 by inserting the leading edge of the pusher sleeve into annular space 62c. A forward movement of the pusher sleeve into annular space 62c will cause pusher rod 66 to move into pressural engagement with plunger 64. As previously mentioned, the fluid within chamber 54 of the vial assembly will resist inward movement of plunger 64 causing the entire vial assembly to move forwardly within chamber 62d to the position where cannula 58 of the adapter subassembly interengages pierceable septum 56a of the container assembly. As previously mentioned, cannula 58 and septum 56a comprise a part of the flow control means of the invention. A continued inward force on the pusher sleeve 50 will cause hollow cannula 58 to pierce septum 56a thereby opening fluid communication between chamber 54 of vial 52 and passageway 70b of valve support assembly 70. Exertion of a continued inward pressure on pusher sleeve 50 will cause plunger 64 to move forwardly of vial chamber 54 causing the fluid contained within chamber 54 to flow into hollow cannula 58 and past check valve 74 of the flow control means of the invention. Because valve member 74 of the adapter subassembly has been moved away from seat 70a by extension 82a, fluid will flow into bypass flow channels 70c formed in member 70. The fluid under pressure will next flow into a chamber 99a formed in base 88. Disposed within chamber 99a is an umbrella valve 99 which also forms a part of the flow control means of the invention and is of a conventional construction well known to those skilled in the art. Umbrella valve 99 permits fluid flow toward passageway 84 but blocks flow in the opposite direction. As the fluid under pressure flows through inlet passageway 84, the stored energy means, or member 90 will be further distended causing additional internal stresses to be built up within the member, which stresses tend to return the member toward its less stressed starting configuration. With reservoir 100 thusly filled, valve member 99 will prevent fluid flow in a direction toward the reservoir fill assembly 42.

Turning particularly to FIGS. 7, 8, 14 and 15, it is to be noted that pusher sleeve 50 is provided with a plurality of longitudinally spaced, upstanding teeth 130 (FIG. 8) which form a part of the locking means of the invention for locking sleeve 50 to the adapter assembly after filling of reservoir 100 has been accomplished. As sleeve 50 is inserted into annular space 62c, teeth 130 will slide under an inwardly extending tab 132 provided on a locking clip 134 which also forms a part of the locking means and which is carried within a relief 136 formed in adapter assembly 48 in the manner shown in FIG. 9. When sleeve 50 is fully inserted into annular space 62c, tab 132 will lockably engage rearward most tooth 130a (FIG. 8) preventing withdrawal of the sleeve from space 62c.

Following the filling step, the adapter assembly 48 can be counterrotated in a manner to be disconnected from the dispenser unit 40 and the closure cap 80 once again placed over subassembly 82 to maintain the subassembly in a protected substantially sterile condition.

At any time after the reservoir filling step, the fluid contained within reservoir 100 can be delivered to the patient by affixing the dispenser unit to the patient using suitable interconnection means. With the unit affixed to the patient, opening of the infusion line will permit the stored energy means or member 90 to move toward its first, less distended configuration thereby controllably urging fluid flow outwardly of the device via outlet portion 140.

As previously mentioned, various fluids can be dispensed from reservoir 100 including, by way of example, beneficial agents such as medicaments of various types, drugs, pharmaceuticals, hormones, antibodies, biologically active materials, elements, chemical compounds, or any other suitable materials used in diagnostic cures, medication, treatment or preventing of diseases, or maintenance of the good health of the patient.

Figure 41:
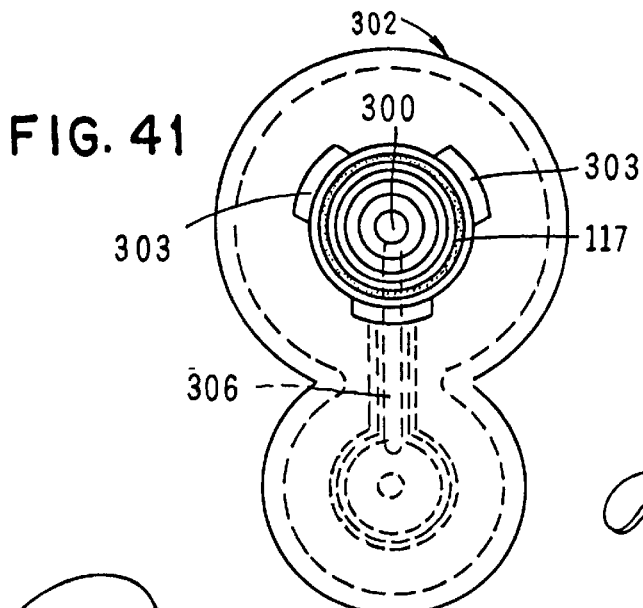
FIG. 41 is a view taken along lines 41—41 of FIG. 34.

Referring next to FIGS. 30 through 41, alternate embodiments of the dispensing apparatus of the invention are there shown. As before, the apparatus comprises a fluid dispenser and a cooperating reservoir fill assembly. The alternate embodiments shown in FIGS. 30 and 41 are similar in many respects to the embodiments in FIGS. 1 through 12 and like numbers are used in these latter drawings to identify like components. In FIG. 30, one form of alternate embodiment is shown fully assembled with the reservoir fill component operably connected to the fluid dispenser component. The fluid dispenser component, which is identified in FIG. 30 by the numeral 40, is identical in construction and operation to the dispenser component previously described in connection with FIGS. 1 through 29.

The major difference between the apparatus of this latest form of the invention and that shown in FIGS. 1 through 29 resides in the fact that the reservoir fill assembly, which is generally designated by the numeral 242, comprises multiple container assemblies 244 and 246 which are receivable within a differently configured adapter assembly 250 (FIG. 30). Referring particularly to FIGS. 30, 30A, 34, and 36, it is to be noted that body 252 of adapter subassembly 250 includes an outer wall 254 and radially spaced apart inner, generally cylindrically shaped walls 256 and 258 (FIGS. 34 and 36).

Walls 254 and 256 define therebetween an elongated annular space 260 within which a first sleeve component 262 is telescopically received (FIG. 30A). Similarly, walls 254 and 258 define therebetween an elongated annular space 264 within which a second sleeve component 266 is received. As shown in FIG. 30, container assembly 244 is closely receivable with a chamber 268 formed internally of wall 256 of the adapter subassembly and can be urged forwardly of chamber 268 by inward telescopic movement of sleeve 262 into space 260. As was the case in the earlier described embodiment, the inboard end 270a of pusher rod 270 engages a first plunger 272 and urges it inwardly of a container reservoir 274 as sleeve 262 is moved inwardly of annular space 260 (FIG. 30A). In a similar fashion, container assembly 246 is closely receivable within a chamber 276 formed internally of wall 258 and can be urged forwardly of chamber 276 by inward telescopic movement of sleeve 266 into space 264. During mating of the second container assembly with the adapter assembly, the inboard end 280a of a pusher rod 280 engages a second plunger 282 and urges it inwardly of a container reservoir 283 as sleeve 266 is moved inwardly of annular space 264 (FIG. 30A).

During the initial mating of sleeves 262 and 266 with adapter subassembly 250, the resistance of the fluid within the containers of the container assemblies or vial cartridges will resist movement of plungers 272 and 282 inwardly of their respective reservoirs so as to cause the vial cartridges to initially move inwardly of their respective chambers to a position wherein a septum 244a of container assembly 244 is engaged by a first cannula 286 of the adapter subassembly and a septum 246a of container assembly 246 is engaged by a second cannula 288 of the adapter subassembly (see also FIG. 33B). As shown in FIG. 36, guide ribs 290 formed interiorly of chamber 268, guide the neck portion of vial assembly 244 toward cannula 286. A continued inward force on sleeves 262 and 266 will cause cannulas 286 and 288 to pierce their respective septums 244a and 246a in the manner shown in FIG. 30, thereby opening fluid communication between the reservoirs of the vial assemblies 244 and 246 and the internal fluid passageway of cannulas 286 and 288.

Once each of the septums has been pierced, the pusher rods of the pusher sleeves 262 and 266 will urge plungers 272 and 282 forwardly of their respective reservoirs causing the fluid within the reservoirs to flow into the central fluid passageways of cannulas 286 and 288 and, via generally "X" shaped passageway 287 and 289 (FIG. 37), toward valve support chambers 294 and 296 formed in body 252 (FIG. 34). Disposed within chamber 294 is a first umbrella valve 298 which is of conventional construction. Umbrella valve 298 permits fluid flow from chamber 294 toward a fluid passageway 300 which is formed in a cover member 302 which is connected to adapter body 252 by any suitable means to form the construction shown in FIG. 30. However, valve 298 is constructed so as to block fluid flow in an opposite direction. Disposed within chamber 296 is a second umbrella valve 304 which permits fluid flow toward a fluid passageway 306 formed in cover 302 but blocks fluid flow in the opposite direction (see FIG. 30). As before, umbrella valves 298 and 304 comprise portions of the flow control means of the invention.

Formed within passageway 300 which is in communication with passageway 306 is a valve seat 300a and a plurality of circumferentially spaced fluid flow grooves 300b (FIGS. 34, 39, and 40). Disposed within passageway 300 is a valve means shown here as a check valve 310 for permitting fluid flow from cannula 286 and fluid passageway 300 toward the fluid reservoir of the dispenser assembly but blocking fluid flow in the opposite direction. Located between check valve 310 and umbrella valve 298 is a valve retainer member 311 which maintains the umbrella valve in position (see also FIG. 38). As shown in FIG. 34, check valve 310, which is of conventional construction, includes a body portion 310a and a seat portion 310b which sealably engages seat 300a when valve 310 is in a closed position. Valve 310 also forms a part of the flow control means of the invention for controlling the flow of fluid toward the dispenser component.

Figure 42:
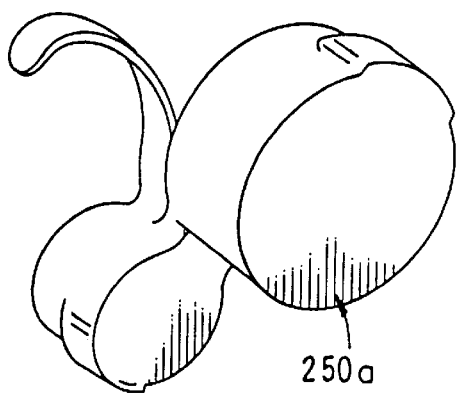
FIG. 42 is a generally perspective view of the closure cap embodiment of the present component of the invention for sealably closing the adapter component of the reservoir fill assembly of the invention shown in FIG. 30A.

It is to be understood that container assemblies 244 and 246 can be filled with various fluids including diluents as well as a wide variety of beneficial agents. Accordingly, following interconnection of the fill assembly with the dispenser component in the manner previously described, the multi-vial reservoir fill assembly of this latest form of the invention can advantageously be used to sequentially fill, or partially fill, the reservoir of the fluid dispenser with fluids contained within the container assemblies for sequential delivery to the patient. Alternatively, the fill assembly can be used to simultaneously fill the fluid dispenser with the fluids contained within container assemblies 244 and 246 thereby creating a fluid mixture which can be delivered to the patient overtime. Referring to FIGS. 34 and 41, it is to be noted that cover 302 is provided with locking tabs 303 which mate in bayonet locking fashion with slots 88a formed in the base of the dispenser component. Prior to use of the adapter subassembly, the open ends thereof are closed by a tear-away cap 250a of the character shown in FIG. 42.

Turning particularly to FIGS. 31A, 31B and 35, it is to be noted that pusher sleeves 262 and 266 are provided with a plurality of longitudinally spaced, upstanding teeth 312 which form a part of the locking means of the invention for locking sleeves 262 and 266 to the adapter assembly after the filling of the reservoir of the fluid dispenser. As the sleeves are inserted into annular spaces 260 and 264, teeth 312 will slide under an inwardly extending tab 314a provided on a pair of locking clips 314 which are of the character shown in FIGS. 30A and 35 and which also form a part of the locking means of the invention. Clips 314 are carried within reliefs 316 and 318 formed in the adapter assembly in the manner shown in FIG. 30A. When the two sleeves are fully inserted into their respective annular spaces, tabs 314a will lockably engage rearward most tooth 312a on the sleeves thereby preventing withdrawal of the sleeves from the annular spacer.

As before, following the filling step, the adapter assembly 250 can be disconnected from the dispenser unit 40 and the closure cap 80 is once again placed over subassembly 82 to maintain the subassembly in a protected substantially sterile condition.

Turning to FIG. 32, an alternate form of coupler mechanism of the invention is there illustrated. The primary difference between this latest form of the invention and those previously described herein resides in the fact that the cover 302a of the adapter assembly of the reservoir fill component is provided with a slit septum 318 in place of the valve means or valve 310. With this construction, in order to enable mating of the reservoir fill assembly with the dispenser unit, the dispenser unit is provided with a blunt end cannula 320 which is adapted to pierce slit septum 318.

Referring next to FIG. 33A, still another form of reservoir fill assembly of the invention is there illustrated. This fill assembly is identical in construction and operation to that shown in FIGS. 34 through 40 save that septum 244a of the container subassembly 244 has been replaced by a slit septum 320 and piercing cannula 286 has been replaced by a blunt end cannula 322. Use of the blunt end cannula 322 and the slit septum 320 in connection with the transfer of fluid from larger container assembly 244 somewhat simplifies the manufacture of the cover member and reduces the cost thereof.

Figure 43:
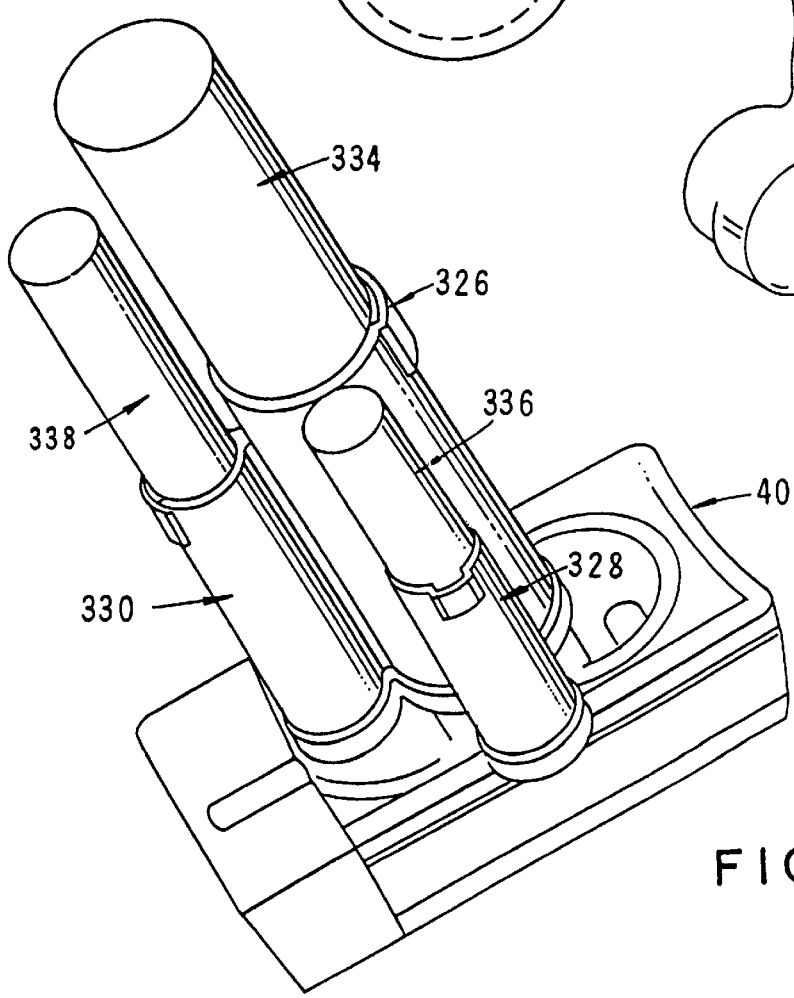
FIG. 43 is a generally perspective view of another embodiment of the fluid delivery apparatus of the invention.
Figures 44, 45:
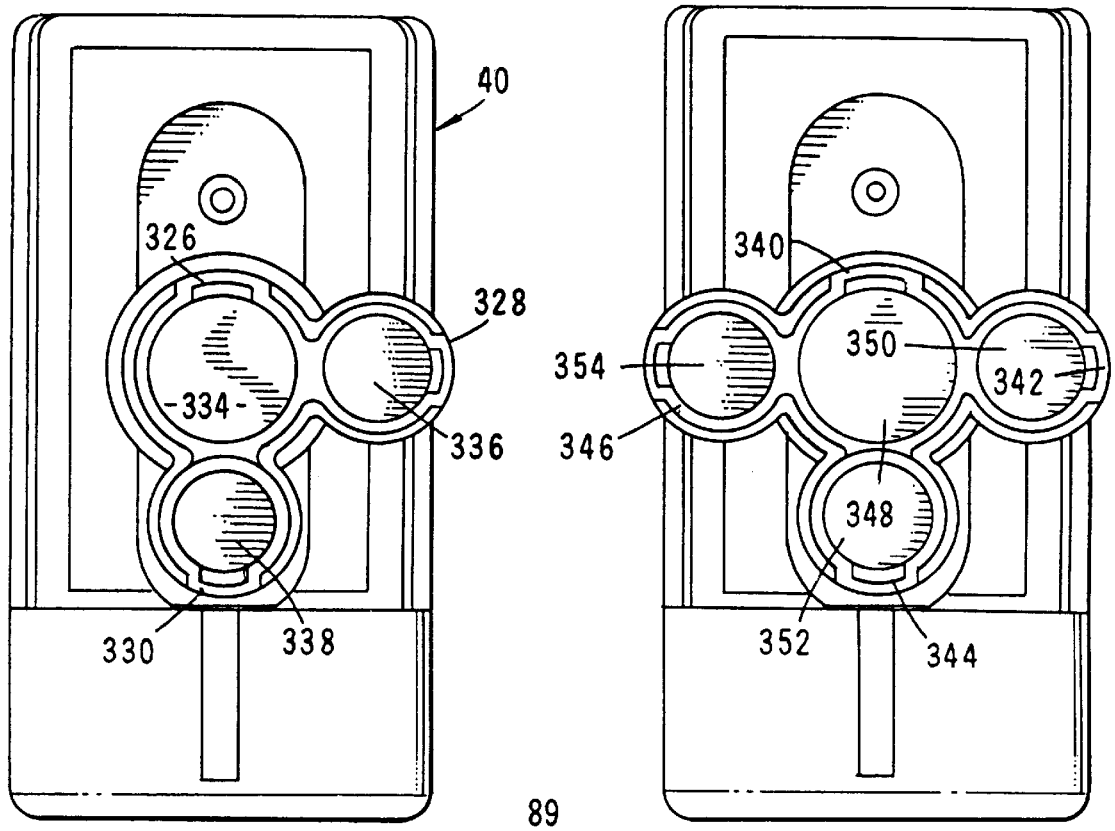
FIG. 44 is a bottom plan view of the embodiment of the invention shown in FIG. 43.
FIG. 45 is a bottom plan view of still another form of the apparatus of the invention.
Figure 47:
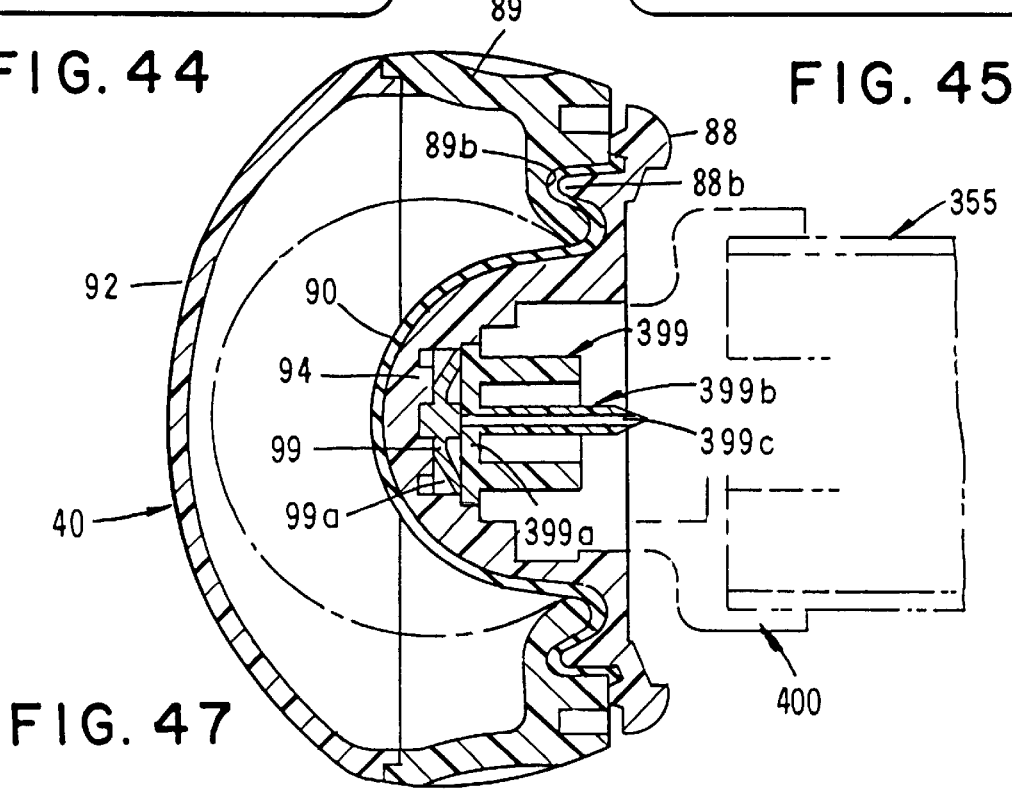
FIG. 47 is a cross-sectional view taken along lines 47—47 of FIG. 46.

Turning next to FIGS. 43, 44 and 45, additional alternate forms of the fluid delivery apparatus are there shown. More particularly, FIGS. 43 and 44 show a reservoir fill assembly which has the capability of filling the fluid reservoir of the fluid dispenser 40 with fluid from three separate container assemblies. As best seen in FIGS. 43 and 44, one form of this latest embodiment of the invention includes first, second and third circumferentially spaced adapter components 326, 328 and 330, each of which contains a separate container assembly. These adapter components are similar in construction and operation to those previously described herein and are adopted to slidably receive pusher sleeves 334, 336 and 338 respectively which are also of similar construction and operation to those previously described.

FIG. 45 illustrates a reservoir fill assembly which has the capability of filling the fluid reservoir of the fluid dispenser with fluids from four container assemblies which assemblies are housed within circumferentially spaced adapter components 340, 342, 344, and 346 and are operated by pusher sleeves 348, 350, 352 and 354 respectively. Once again, these container assemblies, adapter components, and pusher sleeves are of similar construction and operation to those previously described herein.

Figure 46:
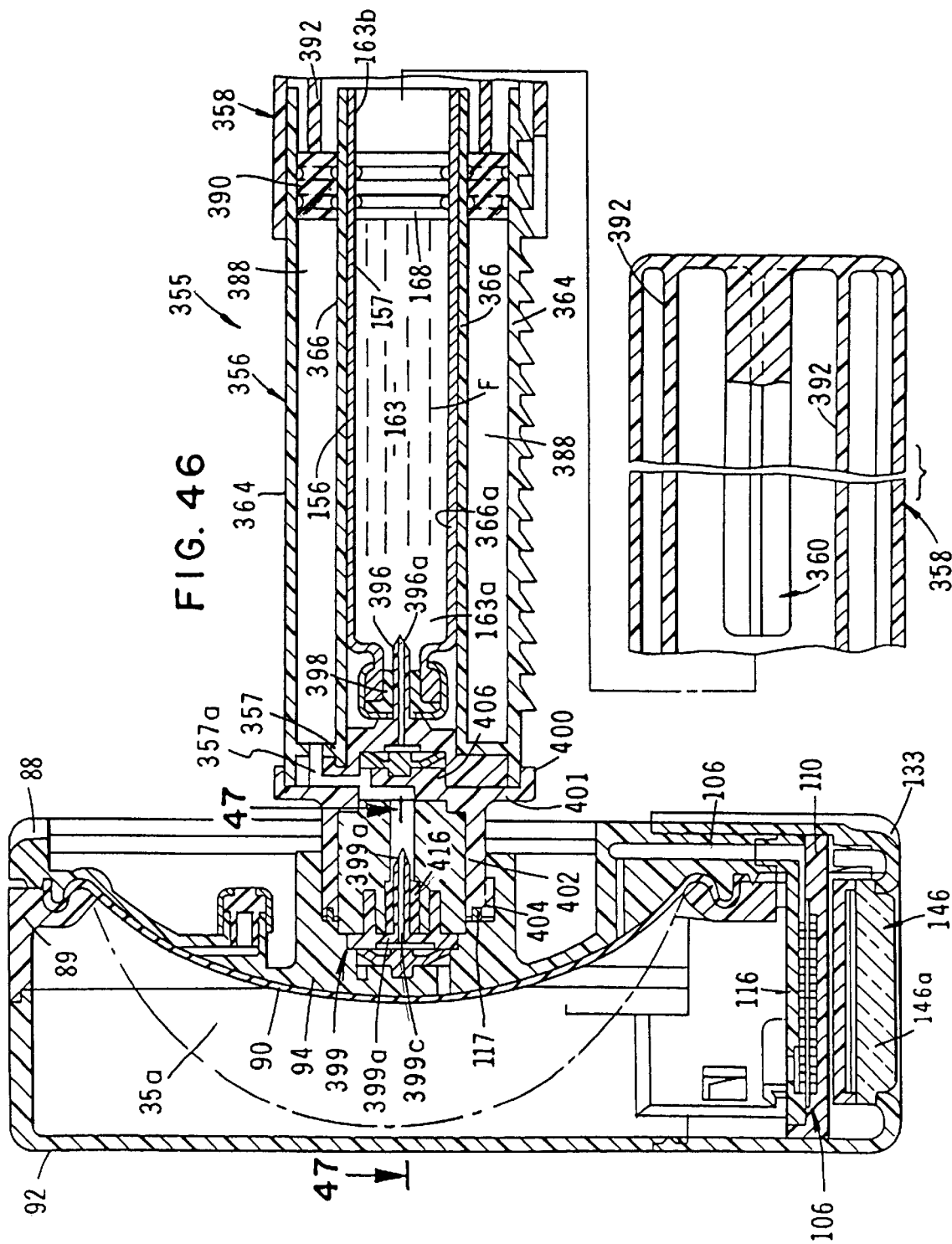
FIG. 46 is a cross-sectional view of another form of the fluid dispenser of the invention showing the dispenser component operably mated with an alternate form of reservoir fill assembly.

Turning next to FIG. 46, another embodiment of the present invention is there shown. In this latest embodiment, the fluid dispenser component is quite similar to that previously described as is the fill assembly. Accordingly, where appropriate, like members are used to designate like components. Once again, this latest embodiment of the reservoir fill assembly, which is generally designated by the numeral 355 comprises three major components, namely a container subassembly 156 which is substantially identical to that previously described, an adapter subassembly 356 which is of slightly different construction from that previously described, and an adapter or pusher sleeve 358 which is also similar to that previously described. As before, container subassembly 156 includes a container such as a vial 157 which contains the medicinal fluid "F" with which the reservoir of the dispensing apparatus is to be filled. As in the earlier described embodiments, the adapter subassembly 356 functions to interconnect the reservoir fill assembly with the fluid dispenser 40 in a manner such that fluid can be transferred from container 157 to the reservoir of the fluid dispenser here generally designated by the numeral 359. This fluid transfer is accomplished by urging sleeve 358 forwardly over the adapter subassembly in the manner indicated in FIG. 46. More particularly, to expel fluid from fluid chamber 163 of container 157 and into reservoir of the dispenser component, a plunger 168 is telescopically movable within chamber 163 by pusher sleeve subassembly 358 which includes pusher means shown here as a pusher rod 360 which, as before, is integrally formed with end wall of the sleeve.

It is to be noted that adapter subassembly 356 of this latest embodiment of the invention includes an outer, generally cylindrically shaped wall 364 and an inner, generally cylindrically shaped wall 366 which define therebetween an elongated annular space 388 within which an annular shaped sealing ring 390 is moved longitudinally by an inner wall 392 of pusher sleeve 358. Annular space 388 comprises a diluent reservoir for containing a suitable diluent. Container assembly 156 is closely receivable within a chamber 366a formed internally of wall 366 of the adapter subassembly and can be urged forwardly of chamber 366a by inward movement of sleeve 358 relative to adapter assembly 356.

Following interconnection of the reservoir fill assembly with the dispenser unit, in the manner shown in FIG. 46, a continued exertion of an inward force on sleeve 358 will cause cannula 396 of the adapter subassembly 356 to pierce septum 398 of the container subassembly in the manner shown in FIGS. 46. This action opens fluid communication between reservoir 163 of vial 157 and the internal fluid passageway 396a of cannula 396. Once septum 398 has been pierced, pusher rod 360 will urge plunger 168 forwardly of reservoir 163 from a first location proximate open end 163b to a second location proximate end 163a. As plunger 168 moves forwardly of reservoir 163, fluid within the reservoir will be caused to flow into cannula passageway 396a for delivery toward the reservoir of the fluid dispenser via a hollow cannula assembly 399 (FIG. 48). During the reservoir filling step the medicinal agent carried within reservoir 163 of vial 157 will be delivered to the reservoir of the dispenser component as will the diluent contained within space 388 with the diluent being intermixed with the medicinal agent as the fluid flows into the dispenser reservoir.

A cover member 400 is connected to wall 364 of the adapter body by any suitable means such as sonic bonding. Cover 400 includes a flanged plate portion 401 and a generally cylindrically shaped extension 402 integrally formed with plate 401. Formed proximate the outboard end of extension 402 are connector means shown here as circumferentially spaced locking tabs 404. Plate 401 of cover 400 includes a generally circular shaped internal recess 406 which receives a cannula support plate 408 of cannula assembly 399 which plate supports cannula 396 (FIGS. 59 and 58). Wall 357 of adapter 355 is provided with a passageway 357a which functions to permit the flow of diluent from space 388 toward cannula 399b (FIG. 46).

Prior to use, the adapter assembly can be appropriately sealed by a tear-away cap. Following removal of this cap, the reservoir fill assembly can be lockably mated with the fluid dispenser in the manner previously described by inserting tabs 404 into the openings provided in the dispenser base of the fluid dispenser.

As shown in FIG. 46, the fluid dispenser of this latest form of the delivery apparatus is quite similar to that shown in FIGS. 1 through 7. However in this latest fluid dispenser construction, the extension 82a of dispenser connector 82 has been replaced with hollow cannula assembly 399 which includes a cannula support plate 399a and a cannula 399b having a fluid passageway 399c. Similarly, valve member 58 has been replaced by a slit septum 416 which is readily pierceable by cannula 399b.

It is to be understood that the same type of coupling mechanism depicted in FIGS. 1 through 7 can be used in the dispenser embodiment shown in FIG. 46. For example, as shown in FIG. 50 where like numbers are used to identify like components, the same type of dispenser connector 82 with extension 82a could be used in conjunction with a valve member such as valve member 74 shown in FIGS. 7 and 50.

Additionally, as shown in FIG. 49 where like numbers are used to identify like components, the dispenser connector could be provided with a slit septum 420 and the fill reservoir connector could be provided with a cannula assembly 422 which comprises a cannula support 422a and a blunt end hollow cannula 422b. A tear-away cover 423 is here used to protect cannula 422b.

Referring to FIGS. 51 through 59, another embodiment of the present invention is there shown. In this latest embodiment, the fluid dispenser component is very similar to that shown in FIG. 46 as is the fill assembly. Accordingly, where appropriate, like members are used to designate like components. The fill assembly of this latest form of the invention, which is generally designated by the numeral 355a comprises three major components, namely a container subassembly 156 which is substantially identical to that previously described, and an adapter subassembly 356a which is of a slightly different construction from that previously described, and an adapter or pusher sleeve 358a which is also similar to that shown in FIG. 46. As before, container subassembly 156 includes a container such as a vial 157 which contains the medicinal fluid "F" with which the reservoir of the dispensing apparatus is to be filled. As in the earlier described embodiments, the adapter subassembly 356a functions to interconnect the reservoir fill assembly with the fluid dispenser in a manner such that fluid can be transferred from container 157 to the reservoir of the fluid dispenser 359. This fluid transfer is accomplished by urging sleeve 358a forwardly over the adapter subassembly in the manner indicated in FIG. 53. More particularly, to expel fluid from fluid chamber 163 of container 157 and into the reservoir of the dispenser component, a plunger 168 is telescopically movable within chamber 163 by pusher sleeve subassembly 358a which includes pusher means shown here as a pusher rod 360a which, as before, is integrally formed with the end wall of the sleeve.

Referring particularly to FIGS. 51, 53, and 54, it is to be noted that adapter subassembly 356a of this last embodiment of the invention includes an outer, generally elliptical shaped wall 364a and an inner, generally cylindrically shaped wall 366 which define therebetween an elongated annular-like space 388a within which an elliptically shaped sealing ring 390a is moved longitudinally by an inner wall of pusher sleeve 358a. Container assembly 156 is closely receivable within a chamber 366a formed internally of wall 366 of the adapter subassembly and can be urged forwardly of chamber 366a by inward movement of sleeve 358a relative to adapter assembly 356a.

Following interconnection of the reservoir fill assembly with the dispenser unit, a continued exertion of an inward force on sleeve 358a will cause cannula 396 of the adapter subassembly 356a to pierce septum 398 of the container subassembly in the manner shown in FIG. 53 (see also FIGS. 58 and 59). This action opens fluid communication between reservoir 163 of vial 157 and the internal fluid passageway 396a of cannula 396. Once septum 398 has been pierced, pusher rod 360a will urge plunger 168 forwardly of reservoir 163 from a first location proximate open end 163b to a second location proximate end 163a. As plunger 168 moves forwardly of reservoir 163, fluid within the reservoir will be caused to flow into cannula passageway 396a for delivery toward the reservoir of the fluid dispenser via a hollow cannula assembly 399. During this reservoir filling step, as ring 390a moves forwardly of space 388a, the diluent contained within space 388a will be urged to flow toward the hollow cannula of the dispenser component and will be intermixed with the medicinal fluid contained within vial 157.

As best seen in FIGS. 51, 52, 53 and 55, a cover member 400a is connected to wall 364a of the adapter body by any suitable means such as sonic bonding. Cover 400a includes a flanged plate portion 401a and a generally cylindrically shaped extension 402a integrally formed with plate 401a. Formed proximate the outboard end of extension 402a are connector means shown here as circumferentially spaced locking tabs 404a. Plate 401a of cover 400a includes a generally circular shaped internal recess 406a which receives a cannula support plate 408a of cannula assembly 399 which plate supports cannula 396 (FIGS. 56 and 58). Plate 408a is provided with a fluid passageway 403 which indexes with a passageway 405a formed in wall 405 of adapter 356a. Passageways 403 and 405a permit flow of the diluent contained within space 388a toward the dispenser component due to the urging of ring 390a.

Prior to use, the adapter assembly is sealed by a peel-away seal 410 and a tear-away cap 412 (FIG. 52). Following removal of seal 410 and cap 412, the reservoir fill assembly can be lockably mated with the fluid dispenser in the manner previously described by inserting tabs 404a into the openings provided in the dispenser base of the fluid dispenser.

Turning to FIGS. 60 through 63, an alternate form of the dispenser component with alternate dispenser flow control means is there shown. As before, these alternate dispenser flow control means function to control fluid flow outwardly of the device. In the embodiment of the invention shown in FIGS. 60, 60A, 61, and 62, the dispenser flow control means comprises a first flow control means 450 and a second back-up flow control means 452. First flow control means 450 includes a fluid flow rate control wafer 450a, which is closely received within a cavity 454 formed in a support means, shown here as a membrane support structure 456. Support structure 456 is similar in many respects to the earlier described structure 110 (FIG. 18) but the fluid distribution means which comprises a multiplicity of circumferentially spaced, manifolding stand-off elements 114 has been replaced by cavities 454 and 458. Wafer 450a is held in position within cavity 454 by a tube-like, elastomeric member 440 (FIGS. 60 and 60A) which is receivable within a recess 462 formed in a boss 464 provided on a disc-like member 466 (FIG. 60). Member 466 is similar in many respects to member 116 which is shown in FIG. 21.

However, the manifolding stand-offs 118 provided on member 116 have been replaced in member 466 with boss 464 which is provided with cavity 462 (see FIG. 60). When member 466 is in place within cavity 458 of structure 456, wafer 450a is securely positioned between elastomeric sleeve 440 and the bottom wall of cavity 454. As before, a vent patch 111 vents to atmosphere any air trapped within the fluid passageways of the device via a vent "V".

As best seen in FIGS. 60 and 61, first flow control means 450 comprises the rate control wafer 450a which has a single laser drilled aperture 451 which controls fluid flow toward an assembly 136, which assembly is identical to that previously described and shown in FIG. 21. Because of the similarity of this latest embodiment of the invention to that shown in FIGS. 18 through 23, like numbers have been used in FIGS. 60 through 62 to identify like components. Laser drilled wafer 450 can be constructed of metal, ceramic or like material and functions to precisely control fluid flow toward assembly 136 at a very precise rate. The second, or back-up flow control means 452, here comprises an assemblage made up of first and second filters 470 and 472 and a flow rate control porous frit 474 disposed intermediate filters 470 and 472. Once again, reference should be made to co-pending Ser. No. 08/718,686 for a more detailed discussion of the various materials suitable for constructing various components of this alternate dispenser flow control means of the invention as described in the preceding paragraphs.

As best seen in FIG. 60, member 466 includes a downwardly extending fluid inlet leg or segment 478 which is provided with a fluid passageway 122. As previously discussed, passageway 122 is adapted to communicate with reservoir 100 of the dispenser via passageway 102 and 102a which member 466 is mated with support structure 110.

With this constriction, when fluid is forced into passageway 102a by the stored energy means, the fluid will flow into passageway 102, then into passageway 122 of member 466 and finally into chamber 462 formed in boss 464. The fluid under pressure will then flow through rate control wafer 450a and toward the fluid outlet port of the flow control subassembly. As before, the outlet port comprises the uniquely shaped assembly 136 which is receivable in a cavity 138 formed in the back or downstream wall 456a of a substrate 456. Assembly 136 includes a fluid outlet 140 and an internal chamber 142.

Fluid flowing from chamber 142 toward outlet 140 via passageway 479a (FIGS. 61 and 62) will flow through the second flow control means or filters 470 and 472 and porous member or frit 474. With the novel construction thus described, should the first flow control means 450 for any reason fail to operate properly, the second back-up flow control means 452 will properly and precisely control fluid flow outwardly of the device via outlet port 140.

Figure 63:
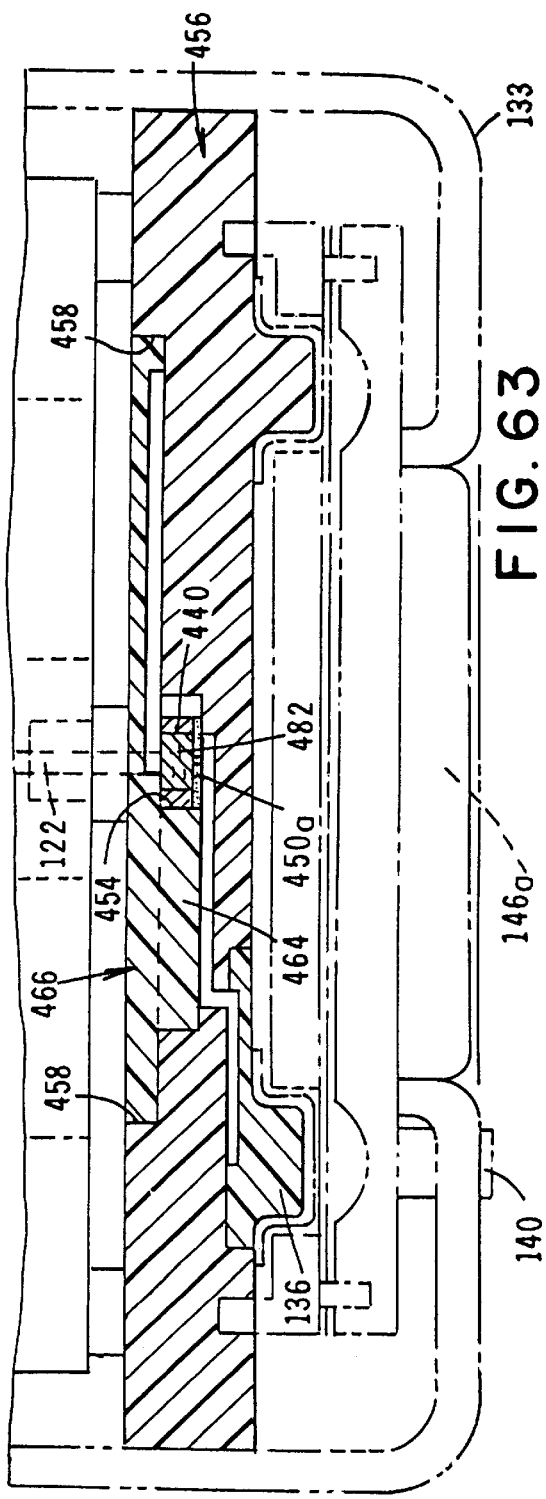
FIG. 63 is a greatly enlarged, fragmentary, cross-sectional view similar to FIG. 23 further illustrating the alternate form of flow control means of the invention shown in FIGS. 60 and 60B.

FIGS. 60B and 63 show still another alternate form of dispenser flow control means of the invention. This alternate flow control means is identical to that described in connection with FIGS. 60, 60A, 61 and 62 save that a porous rate control frit 482 is provided internally of elastomeric sleeve 440. Frit 482 cooperates with apertured wafer 450a to precisely control the rate of fluid flow toward chamber 142 of insert 136.

Figure 64:
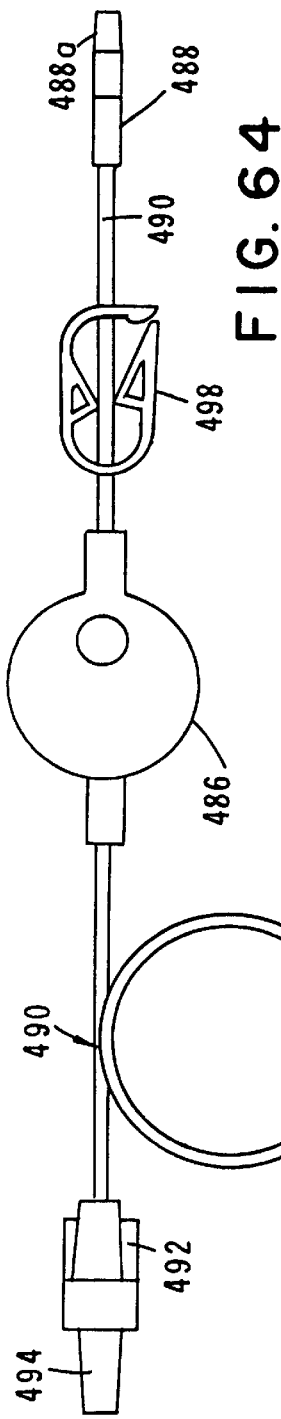
FIG. 64 is a side-elevational view of one form of the infusion means or delivery line assembly of the apparatus of the invention for delivering fluid from the fluid dispenser to the patient.
Figure 65:
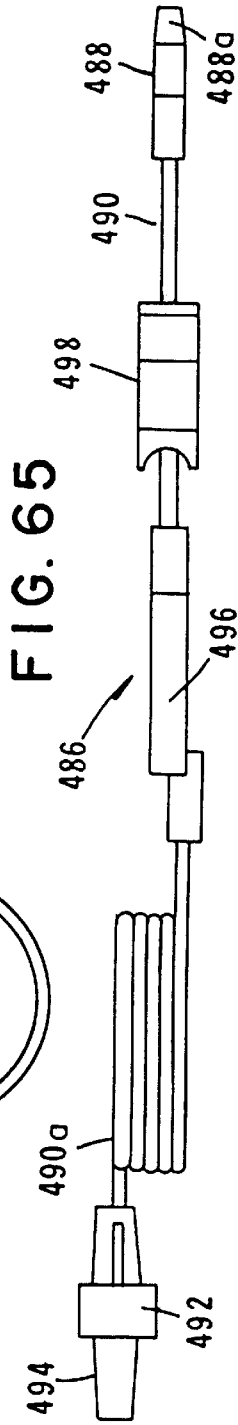
FIG. 65 is a top view of the delivery line assembly shown in FIG. 64.

Referring to FIGS. 64, 65, and 66, one form of infusion means of the apparatus of the invention for delivering fluid from the dispenser component to the patient is there illustrated and generally designated by the numeral 486. This infusion means, or delivery line assembly, includes a connector fitting 488 which functions to interconnect the delivery line assembly with outlet 140 of the dispenser component of the apparatus of the invention. Connector 488 is of a character well known to those skilled in the art and has a tapered connector surface 488a or the character shown in FIG. 66 to enable the connector to be press fit into the outlet of the dispenser component. A long length of tubing 490 interconnects connector 488 with a luer fitting 492 which is of a conventional construction and which receives a luer cap 494. Intermediate the ends of length of tubing 490 is a coiled section 490a (See FIG. 6). Also disposed intermediate the ends of length of tubing 490 is a gas vent and filter 496 which is also of a conventional construction well known to those skilled in the art and readily commercially available from various sources. Disposed between connector 488 and gas vent and filter 496 is a tubing clamp 498 which is also of a character well known to those skilled in the art and functions to block fluid flow through tubing 490.

Disposed within connector 488 is still another form of dispenser flow control means of the present invention. This flow control means is similar to that shown in FIG. 60B and comprises an elastomeric sealing sleeve which is disposed within a cavity 502 formed within the body portion of connector member 488. Positioned within elastomeric sleeve 500 is the latest form of flow rate control means which here comprises first and second filters 504 and 506 and a porous rate control frit 508 disposed therebetween.

It is to be understood that the infusion means or delivery line assembly shown in FIGS. 64, 65, and 66 can be used with any embodiment of the fluid dispenser component of the invention shown in the drawings and previously described herein. Accordingly, use of this novel infusion means can provide secondary flow control to the flow control offered by the flow control means embodied in any specific embodiment of the invention previously described herein.

Turning to FIGS. 67 and 68, still another form of the fluid dispenser component of the apparatus of the present invention is there illustrated. This device is similar in most respects to the device shown in FIGS. 1 through 29 and like numerals are used in FIGS. 67 and 68 to identify like components. The major difference between this latest form of the dispenser component of the invention and that shown in FIG. 4 resides in the provision of the secondary means for filling the reservoir of the device. This secondary filling means comprises a luer connector 510 which is interconnected with the base of the dispenser component in the manner shown in FIG. 67. Disposed between luer connector 510 and a passageway 512 leading to the fluid reservoir of the device is valve means shown here as a conventional umbrella valve 514. A cover 516 is used to close the inlet end 510a of luer connector 510. As shown in FIG. 68, luer connector 510 is provided with inlet flow passageways 518 which are disposed in the crossing relationship shown in FIG. 68. This construction permits fluid flowing into inlet port 510a to flow through passageways 518 into a chamber 520 which houses umbrella valve 514 and then into the reservoir of the unit via passageway 512. As before umbrella valve 514 functions to permit fluid flow toward the reservoir but effectively blocks fluid flow in the opposite direction.

Referring to FIGS. 69 through 81, yet another embodiment of the present invention is there shown. In this latest embodiment, which is generally designated by the numeral 530, the fluid dispenser component is, once again, very similar to those previously described herein. Accordingly, where appropriate, like members are used in FIGS. 69 through 81 to designate like components. The reservoir fill assembly of this latest form of the invention, which is generally designated in the drawings by the numeral 42 is identical to that shown in FIGS. 7 through 16 and is as previously described herein in connection with those figure drawings.

The fluid dispenser component of this latest form of the invention, while being of similar configuration to that shown in FIGS. 1 through 7, does not include the flow indicator means shown in FIGS. 1 through 7. Rather, this latest form of the dispenser component includes a somewhat different infusion means, and importantly includes novel storage means for storing the infusion means designated in FIG. 69 by the numeral 531.

Figure 69:
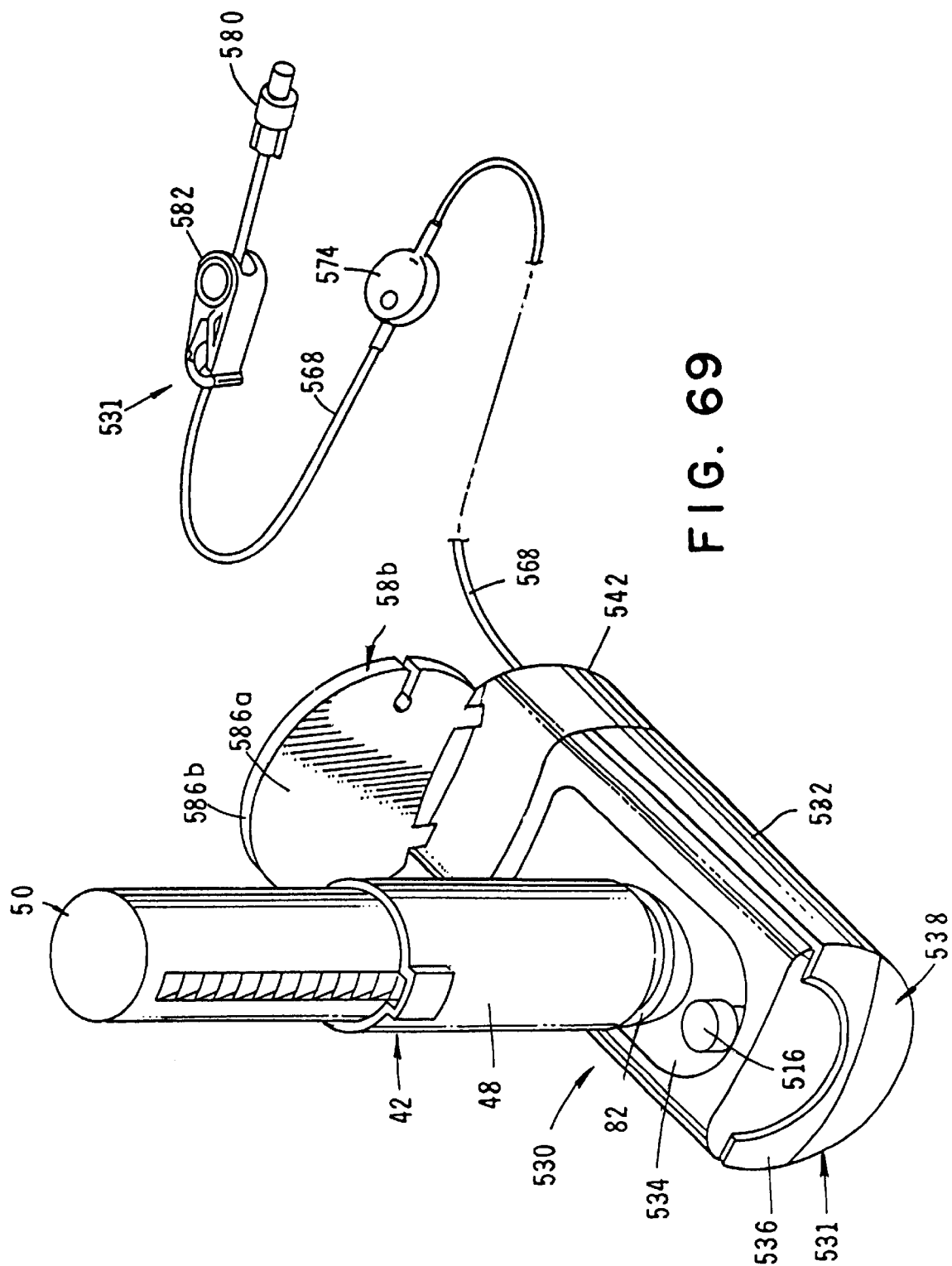
FIG. 69 is a generally perspective bottom view of still another form of the apparatus of the invention having a delivery line assembly stored within a forward compartment of the dispenser housing.
Figure 70:
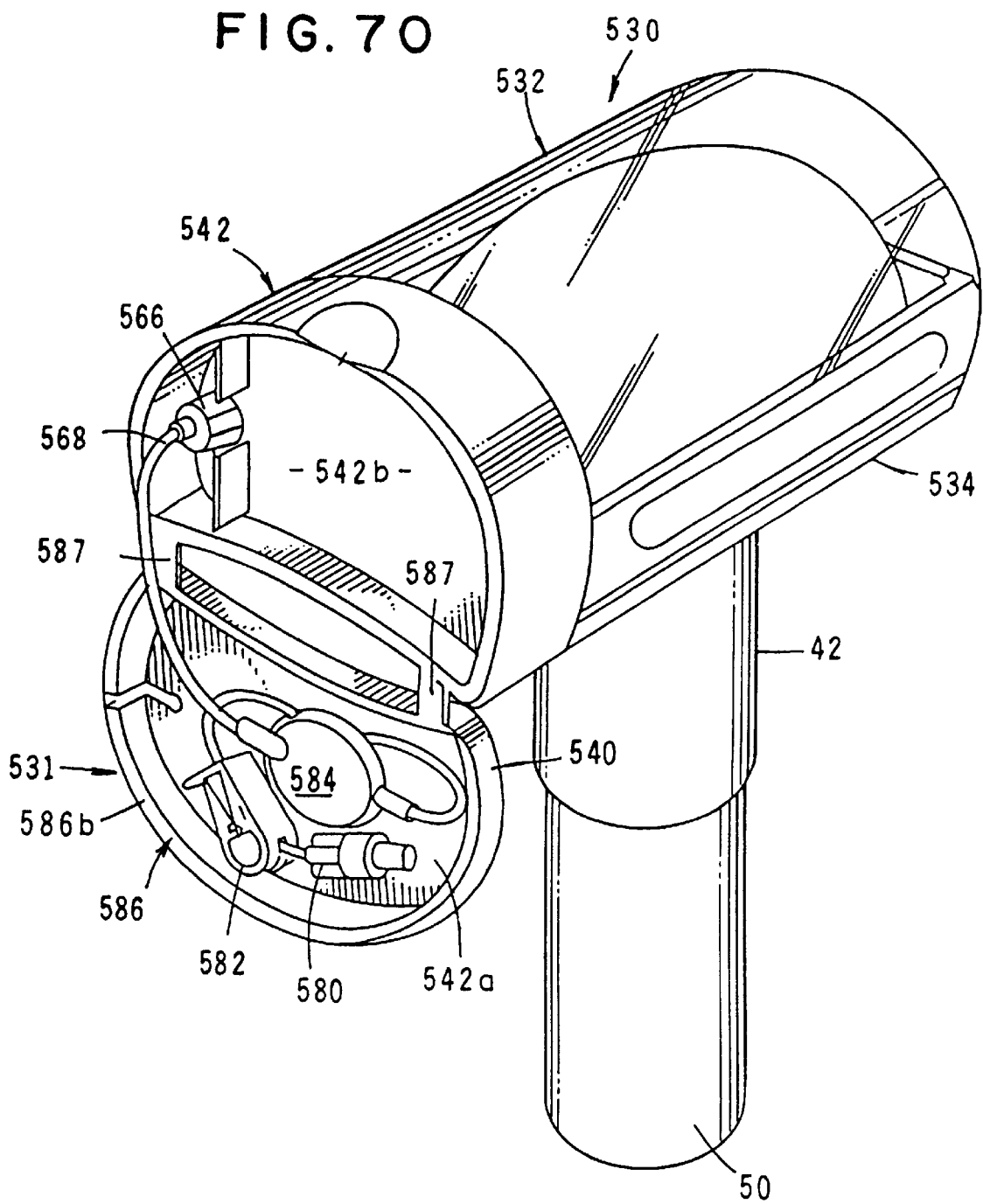
FIG. 70 is a generally perspective top view of the form of the invention illustrated in FIG. 69 better illustrating the configuration of the delivery line assembly and storage compartment of the dispenser.
Figure 71:
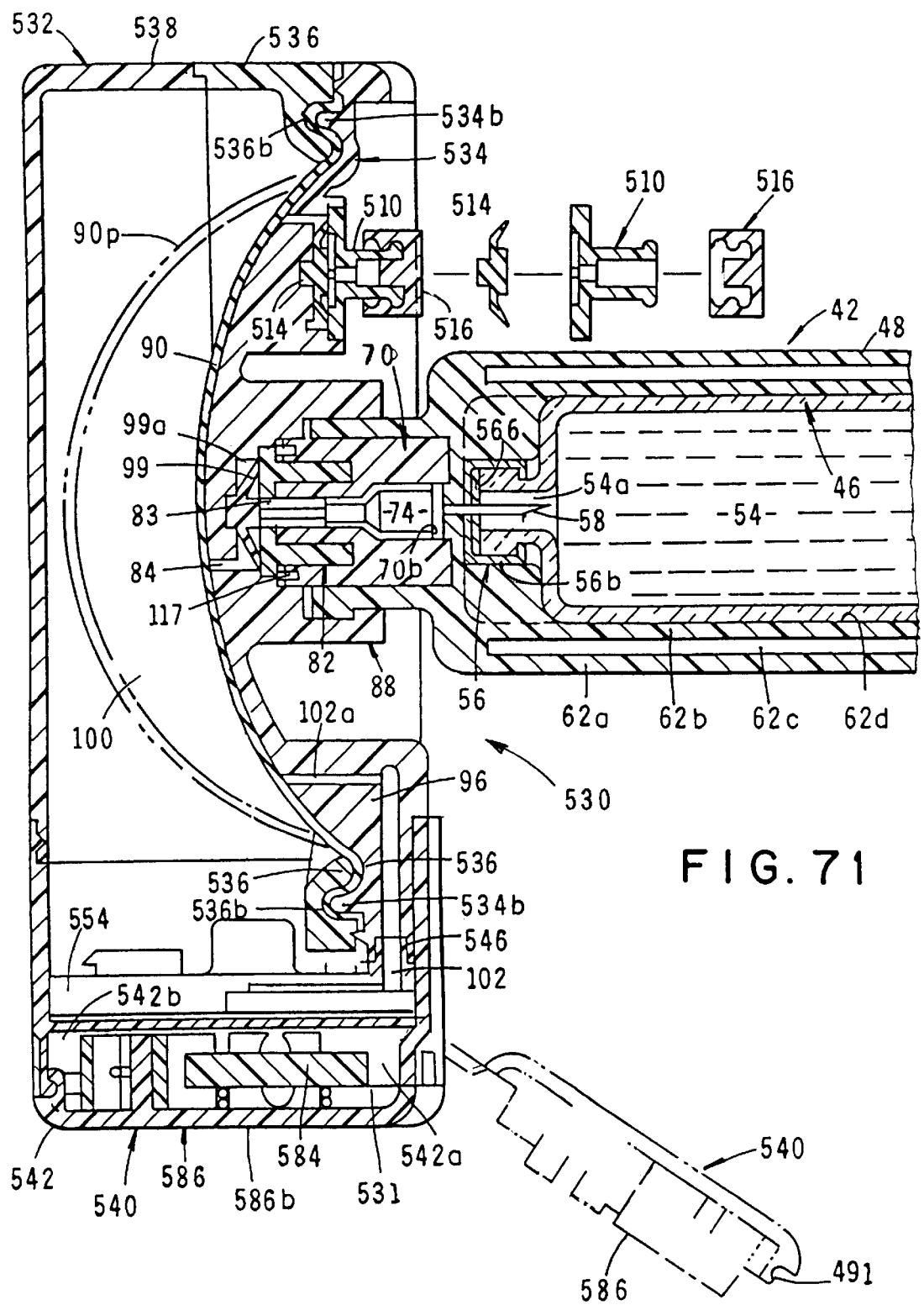
FIG. 71 is a greatly enlarged, cross-sectional view of the apparatus illustrated in FIG. 69 showing the manner of interconnection of the alternate form of dispenser component with the reservoir fill assembly.

Turning particularly to FIGS. 69, 70, and 71, the fluid dispenser assembly of the apparatus of this latest form of the invention, which is designated as 532, includes a housing assembly comprising a base 534, a capture ring 536, a stored energy source, or distendable membrane 90 (FIG. 71) and a cover 538 for enclosing the stored energy source, the capture ring and the base. As shown in FIG. 71, the base 534 includes an ullage defining protuberance 94 and a membrane capture portion 96. Disposed between base 534 and cover 538 is the membrane capture ring 536 which has a bottom opening 536a which receives protuberance 94 of base 534.

Referring particularly to FIGS. 69 and 71, base 534 comprises, in addition to the distendable member engaging protuberance, or ullage 94, the previously identified dispenser connector subassembly 82, to which the reservoir fill assembly 42 is interconnected in the manner shown in FIG. 71. Base 534 also includes an upstanding tongue 534b which extends about the perimeter of the base and is closely receivable within a groove 536b formed in the capture ring 536 (FIG. 71). When the base and the membrane capture ring are assembled in the manner shown in FIG. 71, the periphery of distendable membrane 90 will be securely clamped within groove 536b by tongue 534b. After the parts are thus assembled, base 534 is bonded to capture ring 536 by any suitable means such as sonic bonding which also functions to simultaneously trim membrane 90.

During the reservoir filling step, which is as was previously described in connection with the earlier embodiments, fluid under pressure will flow into inlet passageway 84 of the fluid dispenser via an umbrella valve 99 and thence into a reservoir 100 which is formed between protuberance 94 and distendable membrane 90p which is shown in phantom lines in FIG. 71. Umbrella valve 99 forms a part of the fill flow control means of the invention. As the fluid under pressure flows into the reservoir, it will cause membrane 90 to distend outwardly from protuberance 94 in the manner shown by the phantom lines in FIG. 71.

As previously stated, an important feature of this latest embodiment is the provision of the novel storage means provided proximate the forward end of the housing of the dispenser component. This storage means, which as shown in FIGS. 70, and 71 and is generally designated therein by the numeral 540. This important storage means comprises a part of the cover means of the invention which includes a portion of cover 538.

Figure 72:
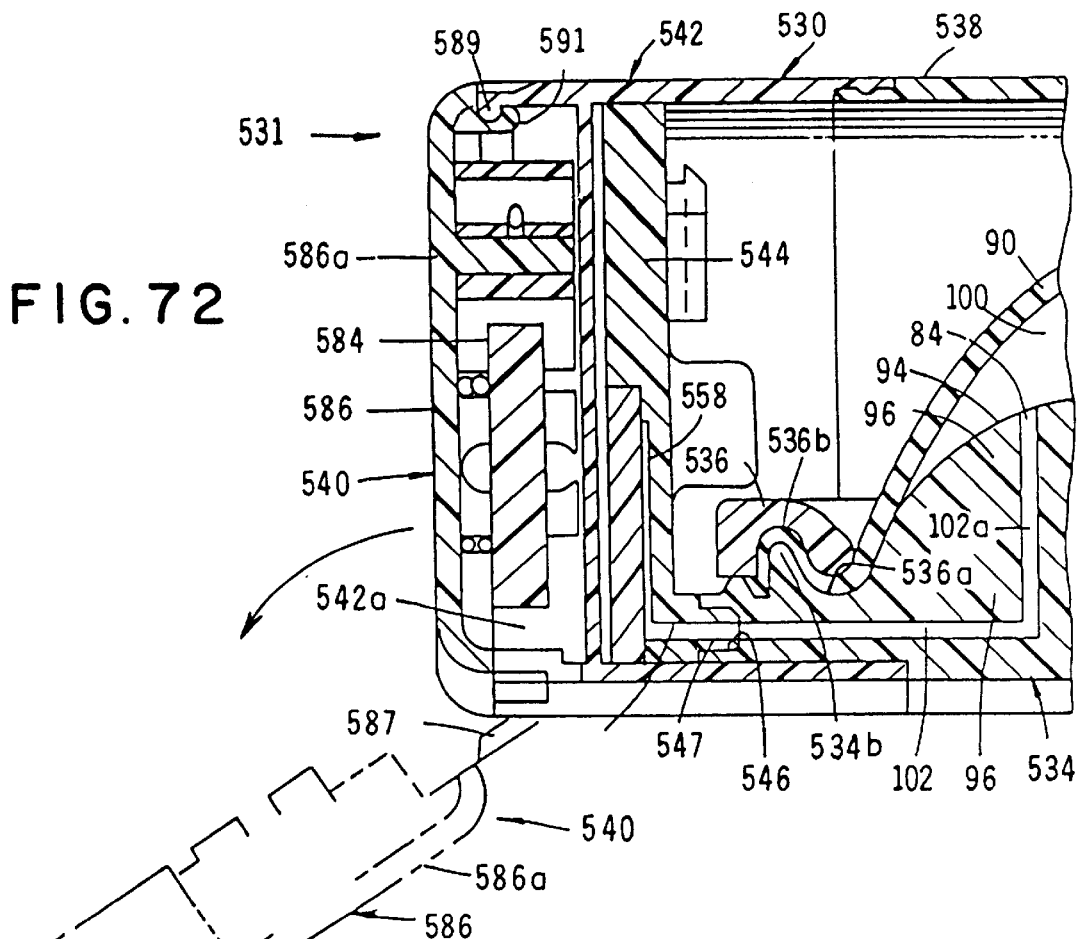
FIG. 72 is an enlarged, fragmentary, cross-sectional view of the forward portion of the form of the dispenser component shown in FIG. 69.

The cover means also includes a housing assembly 542 (FIG. 72) which is interconnected with cover 538 and base 534. Housing assembly 542 functions to close the forward or delivery end of the dispenser component. As best seen in FIG. 72, housing assembly 542 includes a first or forward compartment 542a and a second, or rearward compartment 542b. Rearward compartment 542b houses a support structure 544, the construction of which is illustrated in FIGS. 78 and 79. As there shown, support structure 544 includes an outwardly extending, generally cylindrically shaped, fluid inlet element 546 within which is provided a fluid passageway 548 (FIG. 79). When support structure 544 is mated with base assembly 534, passageway 548 will communicate with reservoir 100 via passageways 102 and 102a (see also FIG. 7). As before, base assembly 534 has a centrally disposed, socket-like recess 547 that closely receives inlet element 546 when structure 544 is mated with base assembly 534 in the manner shown in the drawings.

Figure 74:
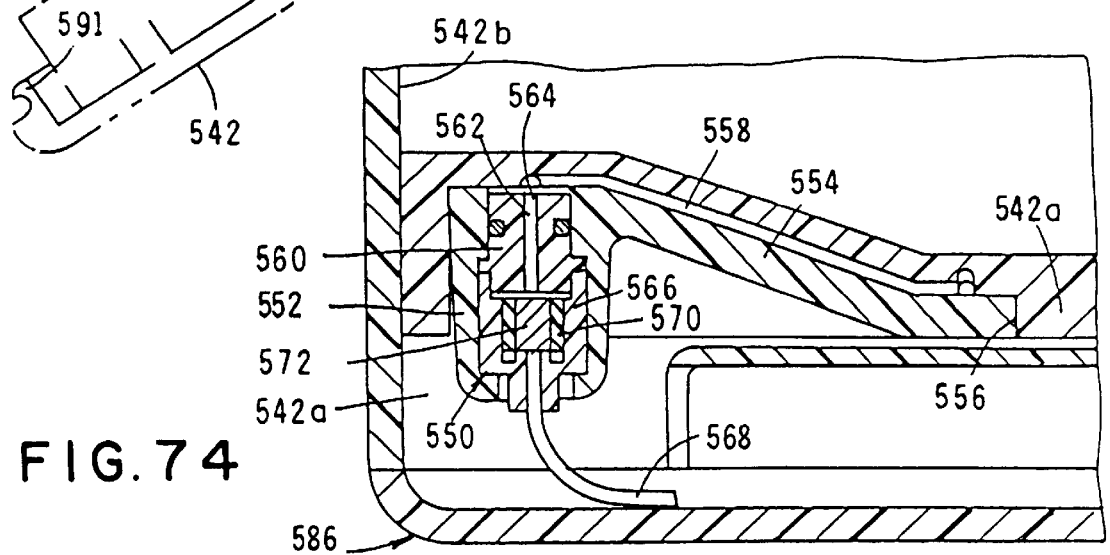
FIG. 74 is a cross-sectional view taken along lines 74—74 of FIG. 73.
Figure 75:
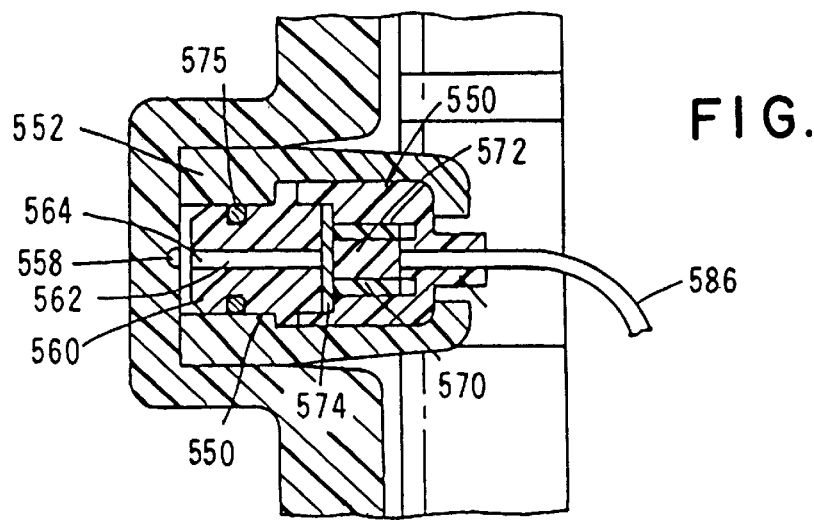
FIG. 75 is a cross-sectional view taken along lines 75—75 of FIG. 73.

The flow control means of this latest form of the invention for controlling the rate of fluid flow of fluid from the device here comprises a novel dispenser flow control assembly 550 of the character shown in FIG. 74 and 75. This dispenser flow control means includes a rate control assembly which is mounted within a socket like portion 552 formed in an insert 554 which is received within cavity 556 formed in the forward wall 544a of support structure 544 (see FIG. 78). Insert 554, in cooperation with a fluid passageway 558 formed in support structure 544, functions to provide a fluid flow path between reservoir 100 and the flow control assembly 550. More particularly, assembly 550 here comprises a quick disconnect housing 560 which has a central fluid passageway 562 having an inlet 564 which communicates with passageway 558 in the manner shown in the drawings.

Figure 76:
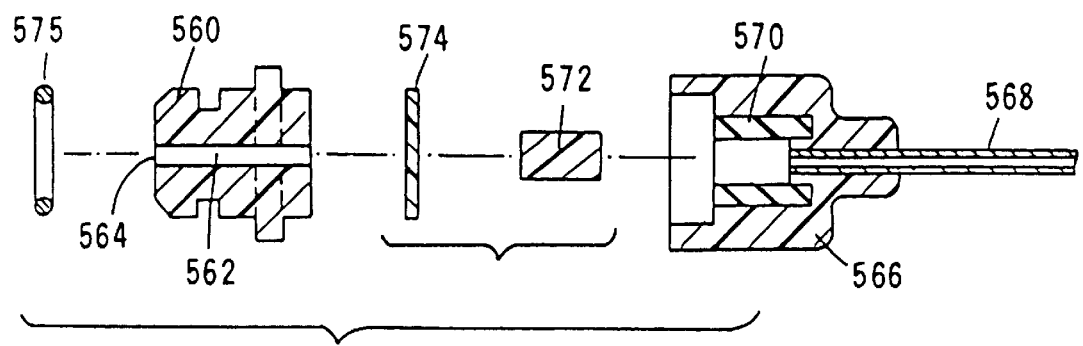
FIG. 76 is an enlarged, exploded, cross-sectional view of the dispenser flow control means of this latest form of the invention.
Figure 77:
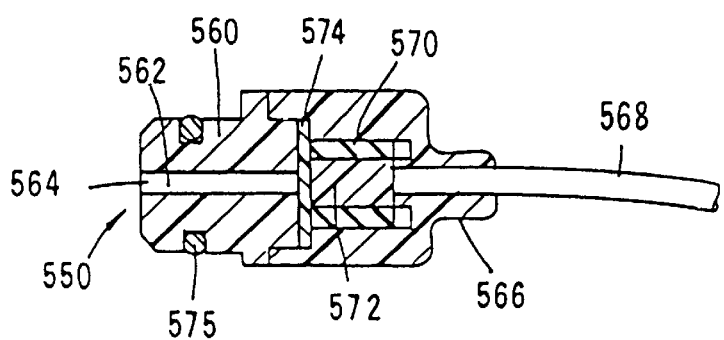
FIG. 77 is a view of the dispenser flow control means illustrated in FIG. 76 showing the flow control means in an assembled configuration.

Interconnected with quick disconnect housing 560 is a delivery line housing 566 to which a delivery line 568 is sealably connected (FIGS. 76 and 77). Disposed within housing 566 is an elastomeric compression ring 570 which sealably receives the dispenser flow rate control means of this form of the invention, which means here comprises a generally cylindrically shaped rate control frit 572. Also forming a part of the dispenser flow control means of this latest embodiment is filter means, here shown as a filter element 574 which is disposed between frit 572 and quick disconnect housing 560 (FIG. 76).

When insert 554 is in position within cavity 556 in the manner shown in FIG. 72, quick connect socket portion 552 extends into forward chamber 542a of the storage means. With this construction, the flow control means can be placed in fluid communication with the fluid reservoir of the dispenser by inserting quick disconnect housing 560 into socket portion 552 and then turning it in a conventional fashion to securely lock it in position. To prevent leakage of fluid between housing 560 and socket portion 552 and elastomeric O-ring 575 is provided in housing 560 (FIGS. 76 and 77).

Connected to the flow control means is the fluid delivery or infusion means of the invention. This latter means, which comprises delivery line assembly 531, is uniquely removably stowed within first or forward compartment 542a of the storage means. As best seen in FIGS. 69 and 70, the infusion means here comprises a luer assembly 580 and a line clamp 582 both of which are of conventional construction. Previously identified delivery line 568 is interconnected with luer assembly 580 in the manner shown in FIG. 73. Disposed between the flow control means and luer assembly 580 is a vent means shown here as a conventional gas vent assembly 584 for venting gases trapped within the system to atmosphere.

Forward compartment 542a is formed within an access door 586 which is connected to that portion of the rearward portion of housing 542 which defines rearward compartment 542b, by hinge means here shown as a part of living hinge elements 587. With this arrangement, door 586 can be pivoted relative to base 534 from the closed position shown by the solid lines in FIG. 72 to the open position show by the phantom lines in FIG. 72. Door 586, which forms a part of the storage means, includes a front face 586a which in cooperation with an interconnected circumscribing wall 586b, forms forward compartment 542a (FIGS. 72 and 73). Latching means, shown here as comprising an arcuate protuberance 589 formed on housing 542, and an arcuate locking tab 591 formed on door 586, cooperate to latchably maintain the door in a normally closed condition (FIG. 72). With this novel arrangement, the infusion means of the invention can remain securely stowed within compartment 542a until time of use.

Figure 80:
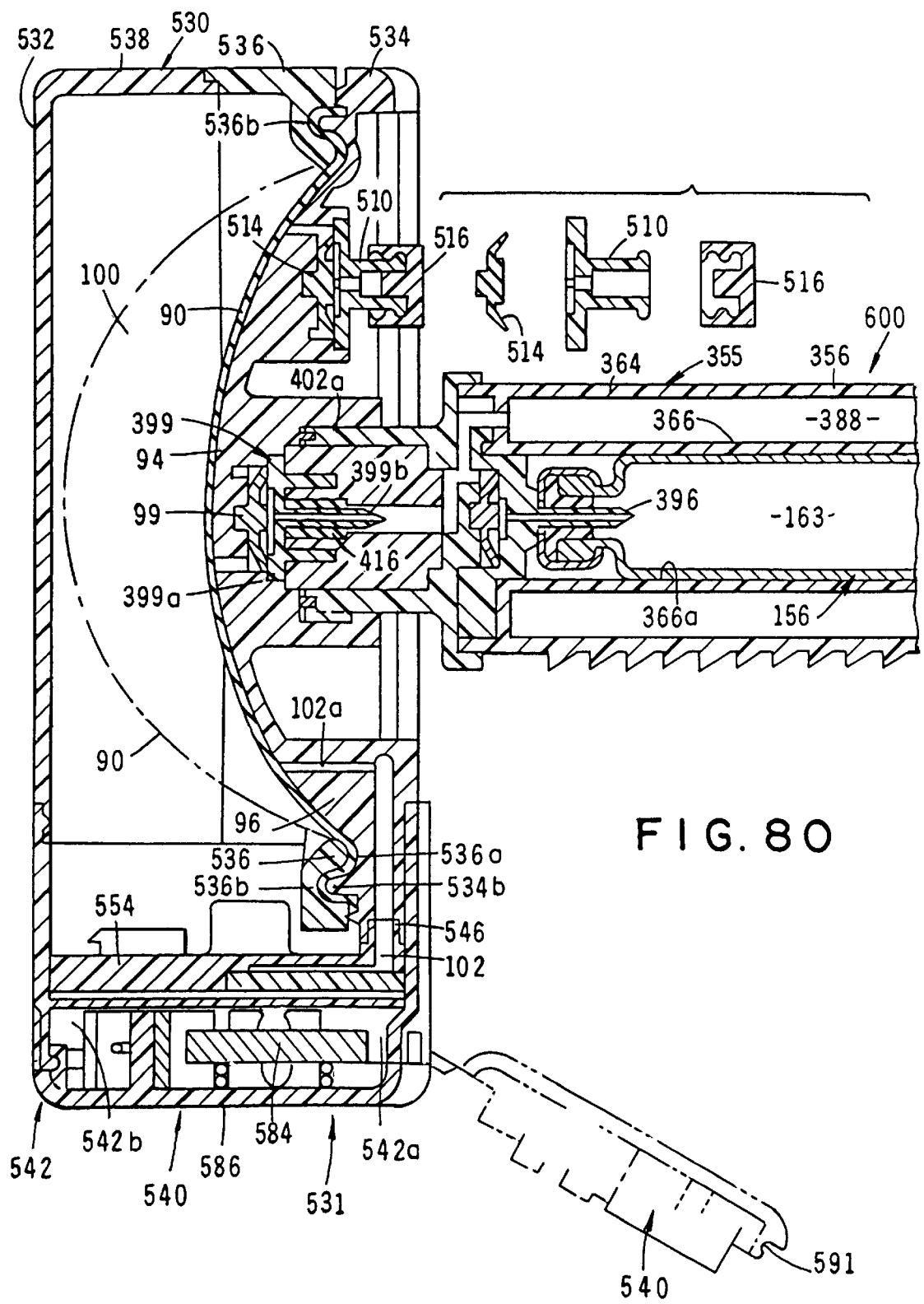
FIG. 80 is an enlarged, side-elevational, cross-sectional view similar to FIG. 71 but showing still another form of the apparatus of the invention.
Figure 80A:
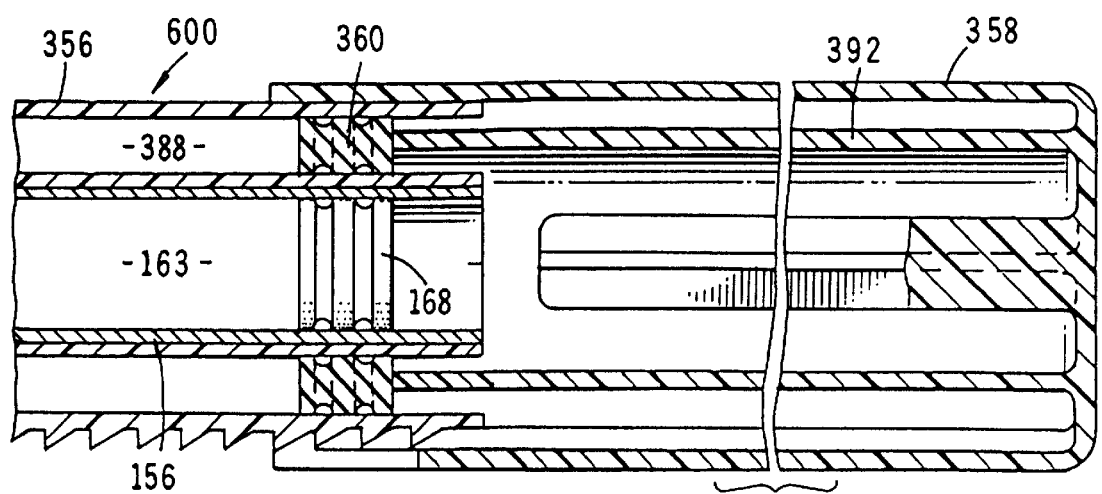
Figure 81:
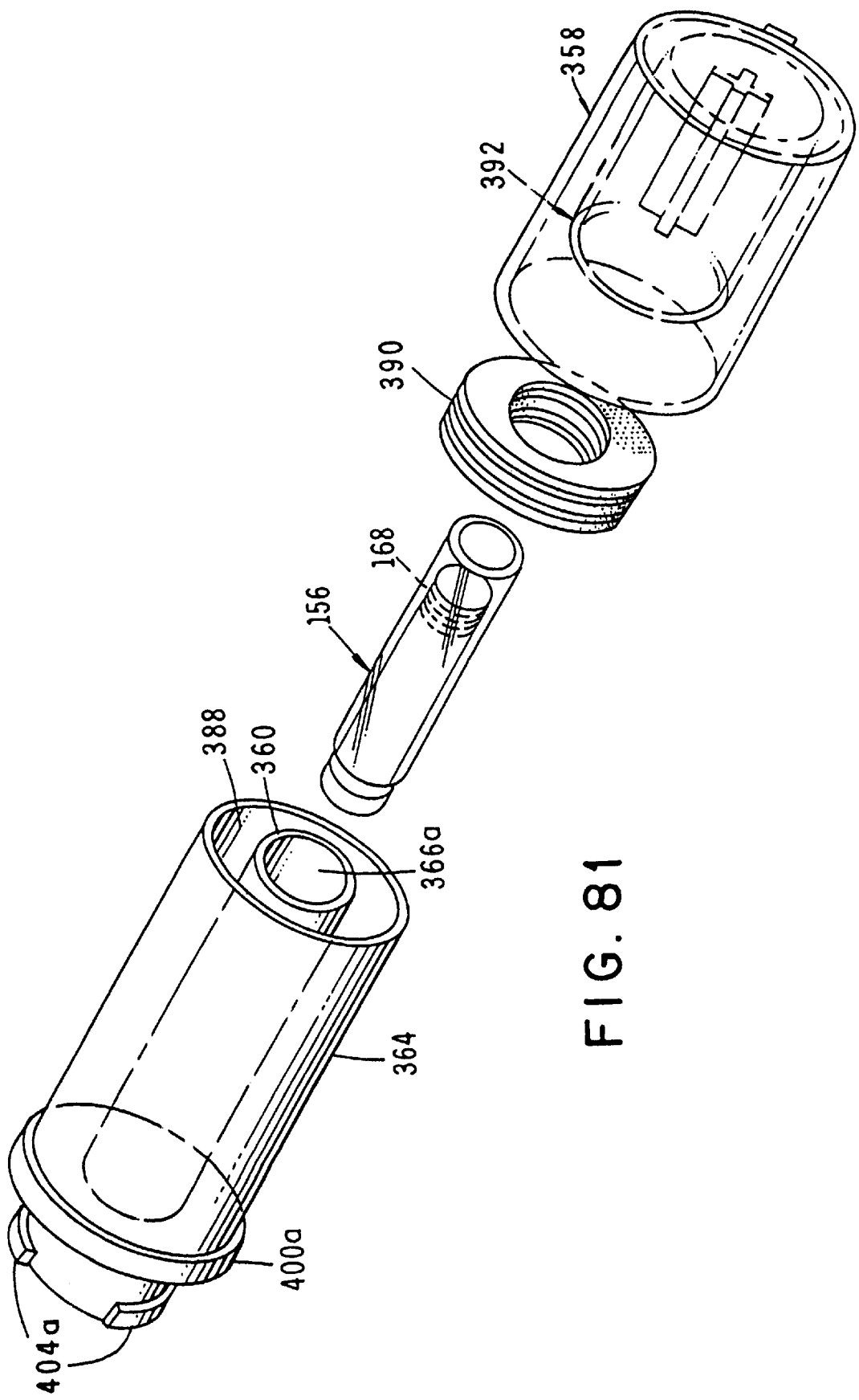
FIG. 81 is a generally perspective, exploded view of the reservoir fill assembly of the apparatus illustrated in FIG. 80.

Turning next to FIGS. 80 and 81, still another form of the apparatus of the invention is there shown and generally identified by a numeral 600. This form of the apparatus is quite similar to that illustrated in FIGS. 45 and 46 and like numbers are used to identify like components.

As shown in FIG. 80, in this latest embodiment, the fluid dispenser component is quite similar to that shown in FIGS. 69 through 71. Similarly, this latest embodiment of the reservoir fill assembly is identical to that shown in 46 and therefore is generally designated by the numeral 355. As before the reservoir fill assembly comprises three major components, namely a container subassembly 156, an adapter subassembly 356, and an adapter or pusher sleeve 358. The reservoir fill assembly 355 operates in the same manner as previously described herein in connection with the FIG. 46 and couples with the dispenser component in precisely the same manner.

It is to be noted that, as before, the adapter subassembly 356 of this latest embodiment of the invention includes an outer, generally cylindrically shaped wall 364, and an inner, generally cylindrically shaped wall 366, which define therebetween an elongated annular space 388 within which an annular shaped sealing ring 390 is moved longitudinally by an inner wall 392 of pusher sleeve 358. As in the earlier described embodiment, annular space 388 comprises a diluent reservoir. Container assembly 156 is closely receivable within a chamber 366a formed internally of wall 366 of the adapter subassembly and can be urged forwardly of chamber 366a by inward sliding movement of sleeve 358 relative to adapter assembly 356.

As shown in FIG. 80, the fluid dispenser of this latest form of the delivery apparatus is very similar to that shown in FIGS. 68 through 71. However, in this latest construction, as was the case in the embodiment shown in FIG. 46, the extension 82a of dispenser connector 82 has been replaced with hollow cannula assembly 399 which includes a cannula support plate 399a and a cannula 399b having a fluid passageway of the character previously described in connection with the embodiment of FIG. 46. Similarly, valve member 58 has been replaced by a slit septum 416 which is readily pierceable by cannula 399b. (See also FIG. 46 and the discussion relating thereto.)

It is to be understood that the same type of coupling mechanism depicted in FIGS. 1 through 7 can be used in the dispenser embodiment shown in FIG. 80.

Additionally, as shown in FIG. 49, the dispenser connector could be provided with a slit septum 420 and the fill reservoir connector could be provided with a cannula assembly 422 which comprises a cannula support 422a and a blunt end hollow cannula 422b.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:
1. A reservoir fill assembly for use in filling the fluid reservoir of a fluid dispenser for dispensing fluid to a patient, said reservoir fill assembly comprising:
 (a) a container subassembly including a container having a fluid chamber and a plunger movable relative to said fluid chamber from a first location to a second, spaced-apart location;
 (b) an adapter subassembly comprising a hollow housing having a fluid outlet, an outer wall and an inner wall defining therebetween a generally annular shaped passageway for containing a fluid, said inner wall having a first open end for telescopically receiving at least a part of said container of said container subassembly and a second end, said hollow housing further including connector means for connecting said adapter subassembly with the fluid dispenser; and
 (c) an adapter sleeve mateable with said adapter subassembly including means for engagement with said plunger of said container subassembly to move said plunger between said first and second locations and further including a generally ring shaped member sealably received within said annular shaped passageway for urging fluid contained within said passageway outwardly thereof toward said fluid outlet of said hollow housing.

2. A reservoir fill assembly as defined in claim 1 in which said inner wall is generally circular in cross section and in which said outer wall is generally elliptical in cross section.

3. A reservoir fill assembly as defined in claim 1 in which said container of said container subassembly includes a pierceable septum and in which said hollow housing of said adapter subassembly includes a hollow cannula for piercing said septum.

4. A reservoir fill assembly as defined in claim 1 in which said adapter subassembly includes valve means for controlling fluid flow toward said fluid outlet.

5. A reservoir fill assembly as defined in claim 1 in which the fluid dispenser includes a septum and in which said adapter subassembly includes a second hollow cannula for piercing a septum of the fluid dispenser.

6. A reservoir fill assembly as defined in claim 1 in which the fluid dispenser includes a hollow cannula and in which said adapter subassembly includes a septum pierceable by the hollow cannula of the fluid dispenser.

7. A reservoir fill assembly as defined in claim 6 in which said septum of said adapter subassembly comprises a slit septum.

8. A reservoir fill assembly for use in filling the fluid reservoir of a fluid dispenser for dispensing fluid to a patient, said reservoir fill assembly comprising:
 (a) a container subassembly including first and second containers each having a fluid chamber and a plunger movable relative to said fluid chamber from a first location to a second, spaced-apart location;
 (b) an adapter subassembly comprising a hollow housing having a fluid outlet, an outer wall and further including:
  (i) a first inner wall defining, in conjunction with said outer wall, a first generally annular-shaped passageway, said first inner wall having a first open end for telescopically receiving at least a portion of said first container of said container subassembly; and (ii) a second inner wall defining in conjunction with said outer wall a second generally annular shaped passageway, said second inner wall having a first open end for telescopically receiving at least a portion of said second container of said container subassembly;

(c) an adapter sleeve mateable with said adapter subassembly including first means for engagement with said plunger of said first container of said container subassembly to move said plunger between said first and second locations and further including second means for engagement with said plunger of said second container of said container subassembly to move said plunger between said first and second locations.

9. A reservoir fill assembly as defined in claim 8 in which said adapter subassembly further includes connector means for connecting said reservoir fill assembly to the fluid dispenser.

10. A reservoir fill assembly as defined in claim 8 in which said first container includes a septum, in which said second container includes a septum and in which said adapter subassembly includes a first hollow cannula for piercing said septum of said first container and further includes a second hollow cannula for piercing said septum of said second container.

11. A reservoir fill assembly as defined in claim 8 further including locking means for locking said adapter sleeve to said adapter subassembly.

12. A reservoir fill assembly as defined in claim 8 in which said adapter subassembly further includes fill flow control means for controlling the flow of fluid toward said fluid outlet of said hollow housing.

13. A reservoir fill assembly as defined in claim 12 in which said fill flow control means comprises a valve.

14. A reservoir fill assembly as defined in claim 13 in which said valve comprises an umbrella valve.

15. A reservoir fill assembly as defined in claim 13 further including a closure cap interconnectable with said adapter subassembly to close said first open ends of said first and second inner walls.

* * * * *